United States Patent
Xu et al.

(10) Patent No.: US 9,683,990 B2
(45) Date of Patent: Jun. 20, 2017

(54) COMPOSITION COMPRISING AN ANGIOPOIETIN-4 FRAGMENT

(75) Inventors: Yin Xu, Philadelphia, PA (US); Qin Yu, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/562,213

(22) Filed: Jul. 30, 2012

(65) Prior Publication Data
US 2013/0059771 A1    Mar. 7, 2013

Related U.S. Application Data

(63) Continuation of application No. 10/558,539, filed as application No. PCT/US2004/016808 on May 28, 2004, now Pat. No. 8,232,247.

(60) Provisional application No. 60/473,998, filed on May 29, 2003, provisional application No. 60/479,802, filed on Jun. 19, 2003.

(51) Int. Cl.
| | |
|---|---|
| *A61K 38/00* | (2006.01) |
| *G01N 33/50* | (2006.01) |
| *C12Q 1/48* | (2006.01) |
| *G01N 33/566* | (2006.01) |
| *G01N 33/574* | (2006.01) |
| *G01N 33/68* | (2006.01) |
| *A61K 38/18* | (2006.01) |
| *A61K 48/00* | (2006.01) |

(52) U.S. Cl.
CPC ..... *G01N 33/5064* (2013.01); *A61K 38/1891* (2013.01); *C12Q 1/485* (2013.01); *G01N 33/566* (2013.01); *G01N 33/574* (2013.01); *G01N 33/6893* (2013.01); *A61K 48/00* (2013.01); *G01N 2333/515* (2013.01); *G01N 2800/042* (2013.01); *G01N 2800/102* (2013.01); *G01N 2800/2871* (2013.01); *G01N 2800/323* (2013.01); *G01N 2800/325* (2013.01)

(58) Field of Classification Search
None
See application file for complete search history.

(56) References Cited

U.S. PATENT DOCUMENTS

| | | | | |
|---|---|---|---|---|
| 6,825,008 | B2 * | 11/2004 | Davis et al. | 435/69.1 |
| 8,232,247 | B2 * | 7/2012 | Xu et al. | 514/13.3 |
| 2005/0106099 | A1 * | 5/2005 | Davis et al. | 424/1.49 |

OTHER PUBLICATIONS

Gale et al. (Genes & Development, vol. 13, pp. 1055-1066,1999).*
Griffloe, et al., Angiogenesis: Potentials for Pharmacologic Intervention in the Treatment of Cancer, Cardiovascular Diseases, and Chronic Inflammation, Pharmcol. Reviews, 2000;52(2):237-68.
Yu, et al., Angiopoietin-2 is implicated in the regulation of tumor angiogenesis, Am J Pathol. Feb. 2001;158(2):563-70.
Fearon, et al., Angiopoietins, growth factors, and vascular morphology in early arthritis, J Rheumatol. Feb. 2003;30(2):260-8.
Olsen, et al., Angiopoietin-4 inhibits angiogenesis and reduces interstitial fluid pressure, Neoplasia. May 2006;8(5):364-72.
Lip, et al., Plasma vascular endothelial growth factor, angiopoietin-2, and soluble angiopoietin receptor tie-2 in diabetic retinopathy: effects of laser photocoagulation and angiotensin receptor blockade, Br J Ophthalmol. Dec. 2004;88(12):1543-6.
Nishimura, et al., Angiopoietin-3, a novel member of the angiopoietin family, FEBS Lett. Apr. 9, 1999;448(2-3):254-6.
Caine, et al., Plasma angiopoietin-1, angiopoietin-2 and Tie-2 in breast and prostate cancer: a comparison with VEGF and Flt-1, Eur J Clin Invest. Oct. 2003;33(10):883-90.
Maisonpierre, et al., Angiopoietin-2, a natural antagonist for Tie2 that disrupts in vivo angiogenesis, Science. Jul. 4, 1997;277(5322):55-60.
Shahrara, et al., Differential expression of the angiogenic Tie receptor family in arthritic and normal synovial tissue, Arthritis Res. 2002;4(3):201-8.
Watkins, Cardiovascular disease, hypertension, and lipids, BMJ. Apr. 19, 2003;326(7394):874-6.
Lee, et al., Biological characterization of angiopoietin-3 and angiopoietin-4, FASEB J. Aug. 2004;18(11):1200-8.

* cited by examiner

*Primary Examiner* — Hope Robinson
(74) *Attorney, Agent, or Firm* — Pepper Hamilton LLP

(57) ABSTRACT

The present invention relates to Angiopoietin-3 (Ang-3) and Angiopoietin-4 (Ang-4). The present invention also relates to methods of modulating an activity of Ang-3 or Ang-4. The present invention further relates to methods of treating cancer, diabetes, and arthritis.

4 Claims, 18 Drawing Sheets

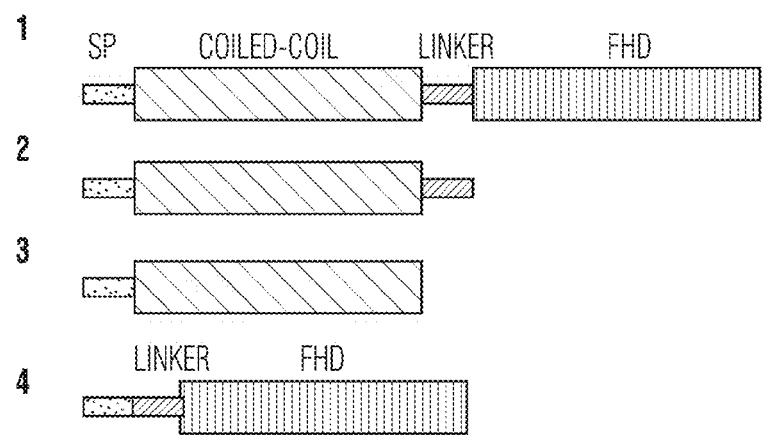
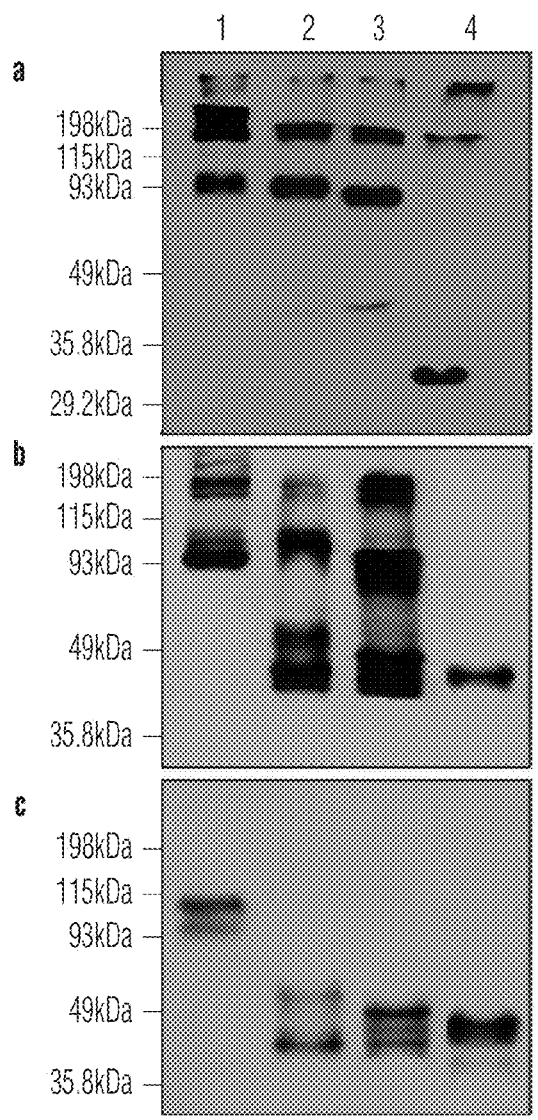
FIG. 4A
FIG. 4B

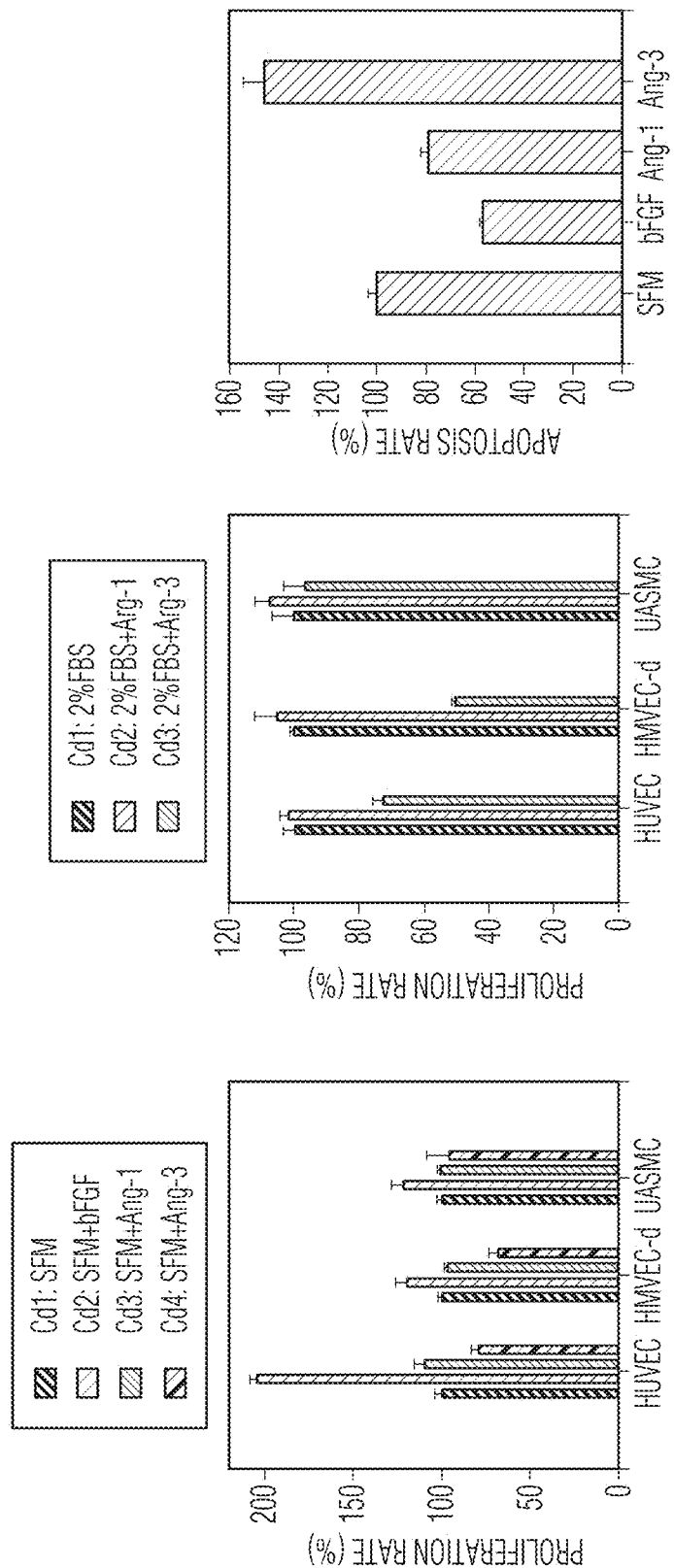

SEQUENCE LISTING

<160> NUMBER OF SEQ ID NOS: 13

<210> SEQ ID NO 1
<211> LENGTH: 1530
<212> TYPE: DNA
<213> ORGANISM: Mus musculus

<400> SEQUENCE: 1

```
atgctctgcc agccagctat gctactagat ggcctcctcc tgctggccac catggctgca      60
gcccagcaca gagggccaga agccggtggg caccgccaga ttcaccaggt ccggcgtggc     120
cagtgcagct acacctttgt ggtgccggag cctgatatct gccagctggc gccgacagcg     180
gcgcctgagg ctttgggggg ctccaatagc ctccagaggg acttgcctgc ctcgaggctg     240
cacctaacag actggcgagc ccagagggcc agcgggccc agcgtgtgag ccagctggag     300
aagatactag agaataacac tcagtggctg ctgaagctgg agcagtccat caaggtgaac     360
ttgaggtcac acctggtgca ggcccagcag gacacaatcc agaaccagac aactaccatg     420
ctggcactgg gtgccaacct catgaaccag accaaagctc agacccacaa gctgactgct     480
gtggaggcac aggtcctaaa ccagacattg cacatgaaga cccaaatgct ggagaactca     540
ctgtccacca acaagctgga gcggcagatg ctgatgcaga gccgagagct gcagcggctg     600
cagggtcgca acagggccct ggagaccagg ctgcaggcac tggaagcaca acatcaggcc     660
cagcttaaca gcctccaaga gaagagggaa caactgcaca gtctcctggg ccatcagacc     720
gggaccctgg ctaacctgaa gcacaatctg cacgctctca gcagcaattc cagctccctg     780
cagcagcagc agcagcaact gacggagttt gtacagcgcc tggtacggat tgtagcccag     840
gaccagcatc cggtttcctt aaagacacct aagccagtgt tccaggactg tgcagagatc     900
aagcgctccg gggttaatac cagcggtgtc tataccatct atgagaccaa catgacaaag     960
cctctcaagg tgttctgtga catggagact gatggaggtg gctggaccct catccagcac    1020
cgggaggatg gaagcgtaaa tttccagagg acctgggaag aatacaaaga gggttttggt    1080
aatgtggcca gagagcactg gctgggcaat gaggctgtgc accgcctcac cagcagaacg    1140
gcctacttgc tacgcgtgga actgcatgac tgggaaggcc gccagacctc catccagtat    1200
gagaacttcc agctgggcag cgagaggcag cggtacagcc tctctgtgaa tgacagcagc    1260
agttcagcag ggcgcaagaa cagcctggct cctcagggca ccaagttcag caccaaagac    1320
atggacaatg ataactgcat gtgtaaatgt gctcagatgc tgtctggagg tggtggttt    1380 gatgcctgtg gcctctccaa cctcaatggc atctactatt cagttcatca gcacttgcac    1440
aagatcaatg gcatccgctg gcactacttc cgaggcccca gctactcact gcacggcaca    1500
cgcatgatgc tgaggccaat gggtgcctga                                     1530
```

<210> SEQ ID NO 2
<211> LENGTH: 509
<212> TYPE: PRT
<213> ORGANISM: Mus musculus

<400> SEQUENCE: 2

```
Met Leu Cys Gln Pro Ala Met Leu Leu Asp Gly Leu Leu Leu Leu Ala
1               5                   10                  15

Thr Met Ala Ala Ala Gln His Arg Gly Pro Glu Ala Gly Gly His Arg
```

```
            20                  25                  30
Gln Ile His Gln Val Arg Arg Gly Gln Cys Ser Tyr Thr Phe Val Val
            35                  40                  45
Pro Glu Pro Asp Ile Cys Gln Leu Ala Pro Thr Ala Ala Pro Glu Ala
50                  55                  60
Leu Gly Gly Ser Asn Ser Leu Gln Arg Asp Leu Pro Ala Ser Arg Leu
65                  70                  75                  80
His Leu Thr Asp Trp Arg Ala Gln Arg Ala Gln Arg Ala Gln Arg Val
                85                  90                  95
Ser Gln Leu Glu Lys Ile Leu Glu Asn Asn Thr Gln Trp Leu Leu Lys
            100                 105                 110
Leu Glu Gln Ser Ile Lys Val Asn Leu Arg Ser His Leu Val Gln Ala
            115                 120                 125
Gln Gln Asp Thr Ile Gln Asn Gln Thr Thr Met Leu Ala Leu Gly
            130                 135                 140
Ala Asn Leu Met Asn Gln Thr Lys Ala Gln Thr His Lys Leu Thr Ala
145                 150                 155                 160
Val Glu Ala Gln Val Leu Asn Gln Thr Leu His Met Lys Thr Gln Met
                165                 170                 175
Leu Glu Asn Ser Leu Ser Thr Asn Lys Leu Glu Arg Gln Met Leu Met
            180                 185                 190
Gln Ser Arg Glu Leu Gln Arg Leu Gln Gly Arg Asn Arg Ala Leu Glu
            195                 200                 205
Thr Arg Leu Gln Ala Leu Glu Ala Gln His Gln Ala Gln Leu Asn Ser
            210                 215                 220
Leu Gln Glu Lys Arg Glu Gln Leu His Ser Leu Leu Gly His Gln Thr
225                 230                 235                 240
Gly Thr Leu Ala Asn Leu Lys His Asn Leu His Ala Leu Ser Ser Asn
                245                 250                 255
Ser Ser Ser Leu Gln Gln Gln Gln Gln Leu Thr Glu Phe Val Gln
            260                 265                 270
Arg Leu Val Arg Ile Val Ala Gln Asp Gln His Pro Val Ser Leu Lys
            275                 280                 285
Thr Pro Lys Pro Val Phe Gln Asp Cys Ala Glu Ile Lys Arg Ser Gly
            290                 295                 300
Val Asn Thr Ser Gly Val Tyr Thr Ile Tyr Glu Thr Asn Met Thr Lys
305                 310                 315                 320
Pro Leu Lys Val Phe Cys Asp Met Glu Thr Asp Gly Gly Trp Thr
                325                 330                 335
Leu Ile Gln His Arg Glu Asp Gly Ser Val Asn Phe Gln Arg Thr Trp
            340                 345                 350
Glu Glu Tyr Lys Glu Gly Phe Gly Asn Val Ala Arg Glu His Trp Leu
            355                 360                 365
Gly Asn Glu Ala Val His Arg Leu Thr Ser Arg Thr Ala Tyr Leu Leu
            370                 375                 380
Arg Val Glu Leu His Asp Trp Glu Gly Arg Gln Thr Ser Ile Gln Tyr
385                 390                 395                 400
Glu Asn Phe Gln Leu Gly Ser Glu Arg Gln Tyr Ser Leu Ser Val
                405                 410                 415
Asn Asp Ser Ser Ser Ala Gly Arg Lys Asn Ser Leu Ala Pro Gln
            420                 425                 430
Gly Thr Lys Phe Ser Thr Lys Asp Met Asp Asn Asp Asn Cys Met Cys
            435                 440                 445
```

Lys Cys Ala Gln Met Leu Ser Gly Gly Trp Trp Phe Asp Ala Cys Gly
        450                 455                 460

Leu Ser Asn Leu Asn Gly Ile Tyr Tyr Ser Val His Gln His Leu His
465                 470                 475                 480

Lys Ile Asn Gly Ile Arg Trp His Tyr Phe Arg Gly Pro Ser Tyr Ser
                485                 490                 495

Leu His Gly Thr Arg Met Met Leu Arg Pro Met Gly Ala
            500                 505

<210> SEQ ID NO 3
<211> LENGTH: 1512
<212> TYPE: DNA
<213> ORGANISM: Homo sapiens

<400> SEQUENCE: 3

| | |
|---|---|
| atgctctccc agctagccat gctgcagggc agcctcctcc ttgtggttgc caccatgtct | 60 |
| gtggctcaac agacaaggca ggaggcggat aggggctgcg agacacttgt agtccagcac | 120 |
| ggccactgta gctacacctt cttgctgccc aagtctgagc cctgccctcc ggggcctgag | 180 |
| gtctccaggg actccaacac cctccagaga gaatcactgg ccaacccact gcacctgggg | 240 |
| aagttgccca cccagcaggt gaaacagctg gagcaggcac tgcagaacaa cacgcagtgg | 300 |
| ctgaagaagc tagagagggc catcaagacg atcttgaggt cgaagctgga gcaggtccag | 360 |
| cagcaaatgg cccagaatca gacggccccc atgctagagc tgggcaccag cctcctgaac | 420 |
| cagaccactg cccagatccg caagctgacc gacatggagg ctcagctcct gaaccagaca | 480 |
| tcaagaatgg atgcccagat gccagagacc tttctgtcca ccaacaagct ggagaaccag | 540 |
| ctgctgctac agaggcagaa gctccagcag cttcagggcc aaaacagcgc gctcgagaag | 600 |
| cggttgcagg ccctggagac caagcagcag gaggagctgg ccagcatcct cagcaagaag | 660 |
| gcgaagctgc tgaacacgct gagccgccag agcgccgccc tcaccaacat cgagcgcggc | 720 |
| ctgcgcggtg tcaggcacaa ctccagcctc ctgcaggacc agcagcacag cctgcgccag | 780 |
| ctgctggtgt tgttgcggca cctggtgcaa gaaagggcta acgcctcggc cccggccttc | 840 |
| ataatggcag tgagcaggt gttccaggac tgtgcagaga tccagcgctc tggggccagt | 900 |
| gccagtggtg tctacaccat ccaggtgtcc aatgcaacga agcccaggaa ggtgttctgt | 960 |
| gacctgcaga gcagtggagg caggtggacc ctcatccagc gccgtgagaa tggcaccgtg | 1020 |
| aattttcagc ggaactggaa ggattacaaa cagggcttcg agacccagc tggggagcac | 1080 |
| tggctgggca atgaagtggt gcaccagctc accagaaggg cagcctactc tctgcgtgtg | 1140 |
| gagctgcaag actgggaagg ccacgaggcc tatgcccagt acgaacattt ccacctgggc | 1200 |
| agtgagaacc agctatacag gctttctgtg gtcgggtaca cgcggctcagc agggcgccag | 1260 |
| agcagcctgg tcctgcagaa caccagcttt agcacccttg actcagacaa cgaccactgt | 1320 |
| ctctgcaagt gtgcccaagt gatgtctgga gggtggtggt ttgacgcctg tggcctgtca | 1380 |
| aacctcaacg gcgtctacta ccacgctccc gacaacaagt acaagatgga cggcatccgc | 1440 |
| tggcactact tcaagggccc cagctactca ctgcgtgcct ctcgcatgat gatacggcct | 1500 |
| ttggacatct aa | 1512 |

<210> SEQ ID NO 4
<211> LENGTH: 334
<212> TYPE: PRT
<213> ORGANISM: Homo sapiens

<400> SEQUENCE: 4

Met Leu Ser Gln Leu Ala Met Leu Gln Gly Ser Leu Leu Val Val
1               5                   10                  15

Ala Thr Met Ser Val Ala Gln Gln Thr Arg Gln Glu Ala Asp Arg Gly
            20                  25                  30

Cys Glu Thr Leu Val Val Gln His Gly His Cys Ser Tyr Thr Phe Leu
            35                  40                  45

Leu Pro Lys Ser Glu Pro Cys Pro Pro Gly Pro Glu Val Ser Arg Asp
        50                  55                  60

Ser Asn Thr Leu Gln Arg Glu Ser Leu Ala Asn Pro Leu His Leu Gly
65                  70                  75                  80

Lys Leu Pro Thr Gln Gln Val Lys Gln Leu Glu Gln Ala Leu Gln Asn
                85                  90                  95

Asn Thr Gln Trp Leu Lys Lys Leu Glu Arg Ala Ile Lys Thr Ile Leu
            100                 105                 110

Arg Ser Lys Leu Glu Gln Val Gln Gln Met Ala Gln Asn Gln Thr
        115                 120                 125

Ala Pro Met Leu Glu Leu Gly Thr Ser Leu Leu Asn Gln Thr Thr Ala
        130                 135                 140

Gln Ile Arg Lys Leu Thr Asp Met Glu Ala Gln Leu Leu Asn Gln Thr
145                 150                 155                 160

Ser Arg Met Asp Ala Gln Met Pro Glu Thr Phe Leu Ser Thr Asn Lys
                165                 170                 175

Leu Glu Asn Gln Leu Leu Leu Gln Arg Gln Lys Leu Gln Gln Leu Gln
            180                 185                 190

Gly Gln Asn Ser Ala Leu Glu Lys Arg Leu Gln Ala Leu Glu Thr Lys
        195                 200                 205

Gln Gln Glu Glu Leu Ala Ser Ile Leu Ser Lys Lys Ala Lys Leu Leu
    210                 215                 220

Asn Thr Leu Ser Arg Gln Ser Ala Ala Leu Thr Asn Ile Glu Arg Gly
225                 230                 235                 240

Leu Arg Gly Val Arg His Asn Ser Ser Leu Leu Gln Asp Gln His
                245                 250                 255

Ser Leu Arg Gln Leu Leu Val Leu Leu Arg His Leu Val Gln Glu Arg
            260                 265                 270

Ala Asn Ala Ser Ala Pro Ala Phe Ile Met Ala Gly Glu Gln Val Phe
        275                 280                 285

Gln Asp Cys Ala Glu Ile Gln Arg Ser Gly Ala Ser Ala Ser Gly Val
    290                 295                 300

Tyr Thr Ile Gln Val Ser Asn Ala Thr Lys Pro Arg Lys Val Phe Cys
305                 310                 315                 320

Asp Leu Gln Ser Ser Gly Gly Arg Trp Thr Leu Ile Gln Arg
                325                 330

<210> SEQ ID NO 5
<211> LENGTH: 102
<212> TYPE: PRT
<213> ORGANISM: Mus musculus

<400> SEQUENCE: 5

Met Leu Cys Gln Pro Ala Met Leu Leu Asp Gly Leu Leu Leu Leu Ala
1               5                   10                  15

Thr Met Ala Ala Ala Gln His Arg Gly Pro Glu Ala Gly Gly His Arg
            20                  25                  30

```
Gln Ile His Gln Val Arg Arg Gly Gln Cys Ser Tyr Thr Phe Val Val
            35                  40                  45

Pro Glu Pro Asp Ile Cys Gln Leu Ala Pro Thr Ala Ala Pro Glu Ala
50                  55                  60

Leu Gly Gly Ser Asn Ser Leu Gln Arg Asp Leu Pro Ala Ser Arg Leu
65                  70                  75                  80

His Leu Thr Asp Trp Arg Ala Gln Arg Ala Gln Arg Ala Gln Arg Val
            85                  90                  95

Ser Gln Leu Glu Lys Ile
            100

<210> SEQ ID NO 6
<211> LENGTH: 263
<212> TYPE: PRT
<213> ORGANISM: Homo sapiens

<400> SEQUENCE: 6

Met Leu Ser Gln Leu Ala Met Leu Gln Gly Ser Leu Leu Val Val
1               5                   10                  15

Ala Thr Met Ser Val Ala Gln Gln Thr Arg Gln Glu Ala Asp Arg Gly
                20                  25                  30

Cys Glu Thr Leu Val Val Gln His Gly His Cys Ser Tyr Thr Phe Leu
            35                  40                  45

Leu Pro Lys Ser Glu Pro Cys Pro Pro Gly Pro Glu Val Ser Arg Asp
50                  55                  60

Ser Asn Thr Leu Gln Arg Glu Ser Leu Ala Asn Pro Leu His Leu Gly
65                  70                  75                  80

Lys Leu Pro Thr Gln Gln Val Lys Gln Leu Glu Gln Ala Leu Gln Asn
            85                  90                  95

Asn Thr Gln Trp Leu Lys Lys Leu Glu Arg Ala Ile Lys Thr Ile Leu
                100                 105                 110

Arg Ser Lys Leu Glu Gln Val Gln Gln Met Ala Gln Asn Gln Thr
            115                 120                 125

Ala Pro Met Leu Glu Leu Gly Thr Ser Leu Leu Asn Gln Thr Thr Ala
130                 135                 140

Gln Ile Arg Lys Leu Thr Asp Met Glu Ala Gln Leu Leu Asn Gln Thr
145                 150                 155                 160

Ser Arg Met Asp Ala Gln Met Pro Glu Thr Phe Leu Ser Thr Asn Lys
                165                 170                 175

Leu Glu Asn Gln Leu Leu Leu Gln Arg Gln Lys Leu Gln Gln Leu Gln
            180                 185                 190

Gly Gln Asn Ser Ala Leu Glu Lys Arg Leu Gln Ala Leu Glu Thr Lys
        195                 200                 205

Gln Gln Glu Glu Leu Ala Ser Ile Leu Ser Lys Lys Ala Lys Leu Leu
210                 215                 220

Asn Thr Leu Ser Arg Gln Ser Ala Ala Leu Thr Asn Ile Glu Arg Gly
225                 230                 235                 240

Leu Arg Gly Val Arg His Asn Ser Ser Leu Leu Gln Asp Gln His
                245                 250                 255

Ser Leu Arg Gln Leu Leu Val
            260

<210> SEQ ID NO 7
<211> LENGTH: 816
<212> TYPE: DNA
<213> ORGANISM: Mus musculus
```

<400> SEQUENCE: 7

```
atgctctgcc agccagctat gctactagat ggcctcctcc tgctggccac catggctgca      60
gcccagcaca gagggccaga agccggtggg caccgccaga ttcaccaggt ccggcgtggc     120
cagtgcagct acacctttgt ggtgccggag cctgatatct gccagctggc gccgacagcg     180
gcgcctgagg ctttgggggg ctccaatagc ctccagaggg acttgcctgc ctcgaggctg     240
cacctaacag actggcgagc cagagggcc cagcgggccc agcgtgtgag ccagctggag      300
aagatactag agaataacac tcagtggctg ctgaagctgg agcagtccat caaggtgaac     360
ttgaggtcac acctggtgca ggcccagcag gacacaatcc agaaccagac aactaccatg     420
ctggcactgg gtgccaacct catgaaccag accaaagctc agacccacaa gctgactgct     480
gtggaggcac aggtcctaaa ccagacattg cacatgaaga cccaaatgct ggagaactca     540
ctgtccacca acaagctgga gcggcagatg ctgatgcaga gccgagagct gcagcggctg     600
cagggtcgca cagggccct ggagaccagg ctgcaggcac tggaagcaca acatcaggcc      660
cagcttaaca gcctccaaga agagggaa caactgcaca gtctcctggg ccatcagacc       720
gggacccctgg ctaacctgaa gcacaatctg cacgctctca gcagcaattc cagctccctg    780
cagcagcagc agcagcaact gacggagttt gtacag                                816
```

<210> SEQ ID NO 8
<211> LENGTH: 789
<212> TYPE: DNA
<213> ORGANISM: Homo sapiens

<400> SEQUENCE: 8

```
atgctctccc agctagccat gctgcagggc agcctcctcc ttgtggttgc caccatgtct      60
gtggctcaac agacaaggca ggaggcggat aggggctgcg agacacttgt agtccagcac     120
ggccactgta gctacacctt cttgctgccc aagtctgagc cctgccctcc ggggcctgag     180
gtctccaggg actccaacac cctccagaga gaatcactgg ccaacccact gcacctgggg    240
aagttgccca cccagcaggt gaaacagctg gagcaggcac tgcagaacaa cacgcagtgg     300
ctgaagaagc tagagagggc catcaagacg atcttgaggt cgaagctgga gcaggtccag     360
cagcaaatgg cccagaatca gacggccccc atgctagagc tgggcaccag cctcctgaac     420
cagaccactg cccagatccg caagctgacc gacatggagg ctcagctcct gaaccagaca     480
tcaagaatgg atgcccagat gccagagacc tttctgtcca ccaacaagct ggagaaccag     540
ctgctgctac agaggcagaa gctccagcag cttcagggcc aaaacagcgc gctcgagaag     600
cggttgcagg ccctggagac caagcagcag gaggagctgg ccagcatcct cagcaagaag    660
gcgaagctgc tgaacacgct gagccgccag agcgccgccc tcaccaacat cgagcgcggc     720
ctgcgcggtg tcaggcacaa ctccagcctc ctgcaggacc agcagcacag cctgcgccag     780
ctgctggtg                                                             789
```

<210> SEQ ID NO 9
<211> LENGTH: 293
<212> TYPE: PRT
<213> ORGANISM: Mus musculus

<400> SEQUENCE: 9

```
Met Leu Cys Gln Pro Ala Met Leu Leu Asp Gly Leu Leu Leu Leu Ala
1               5                   10                  15

Thr Met Ala Ala Ala Gln His Arg Gly Pro Glu Ala Gly Gly His Arg
```

```
                    20                  25                  30
Gln Ile His Gln Val Arg Arg Gly Gln Cys Ser Tyr Thr Phe Val Val
            35                  40                  45

Pro Glu Pro Asp Ile Cys Gln Leu Ala Pro Thr Ala Ala Pro Glu Ala
 50                  55                  60

Leu Gly Gly Ser Asn Ser Leu Gln Arg Asp Leu Pro Ala Ser Arg Leu
 65                  70                  75                  80

His Leu Thr Asp Trp Arg Ala Gln Arg Ala Gln Arg Ala Gln Arg Val
                    85                  90                  95

Ser Gln Leu Glu Lys Ile Leu Glu Asn Asn Thr Gln Trp Leu Leu Lys
            100                 105                 110

Leu Glu Gln Ser Ile Lys Val Asn Leu Arg Ser His Leu Val Gln Ala
            115                 120                 125

Gln Gln Asp Thr Ile Gln Asn Gln Thr Thr Met Leu Ala Leu Gly
            130                 135                 140

Ala Asn Leu Met Asn Gln Thr Lys Ala Gln Thr His Lys Leu Thr Ala
145                 150                 155                 160

Val Glu Ala Gln Val Leu Asn Gln Thr Leu His Met Lys Thr Gln Met
                    165                 170                 175

Leu Glu Asn Ser Leu Ser Thr Asn Lys Leu Glu Arg Gln Met Leu Met
                    180                 185                 190

Gln Ser Arg Glu Leu Gln Arg Leu Gln Gly Arg Asn Arg Ala Leu Glu
            195                 200                 205

Thr Arg Leu Gln Ala Leu Glu Ala Gln His Gln Ala Gln Leu Asn Ser
            210                 215                 220

Leu Gln Glu Lys Arg Glu Gln Leu His Ser Leu Gly His Gln Thr
225                 230                 235                 240

Gly Thr Leu Ala Asn Leu Lys His Asn Leu His Ala Leu Ser Ser Asn
                    245                 250                 255

Ser Ser Ser Leu Gln Gln Gln Gln Gln Leu Thr Glu Phe Val Gln
                    260                 265                 270

Arg Leu Val Arg Ile Val Ala Gln Asp Gln His Pro Val Ser Leu Lys
            275                 280                 285

Thr Pro Lys Pro Val
            290

<210> SEQ ID NO 10
<211> LENGTH: 287
<212> TYPE: PRT
<213> ORGANISM: Homo sapiens

<400> SEQUENCE: 10

Met Leu Ser Gln Leu Ala Met Leu Gln Gly Ser Leu Leu Val Val
 1               5                  10                  15

Ala Thr Met Ser Val Ala Gln Gln Thr Arg Gln Glu Ala Asp Arg Gly
                    20                  25                  30

Cys Glu Thr Leu Val Val Gln His Gly His Cys Ser Tyr Thr Phe Leu
            35                  40                  45

Leu Pro Lys Ser Glu Pro Cys Pro Pro Gly Pro Glu Val Ser Arg Asp
            50                  55                  60

Ser Asn Thr Leu Gln Arg Glu Ser Leu Ala Asn Pro Leu His Leu Gly
 65                  70                  75                  80

Lys Leu Pro Thr Gln Gln Val Lys Gln Leu Glu Gln Ala Leu Gln Asn
                    85                  90                  95
```

```
Asn Thr Gln Trp Leu Lys Lys Leu Glu Arg Ala Ile Lys Thr Ile Leu
            100                 105                 110
Arg Ser Lys Leu Glu Gln Val Gln Gln Met Ala Gln Asn Gln Thr
        115                 120                 125
Ala Pro Met Leu Glu Leu Gly Thr Ser Leu Leu Asn Gln Thr Thr Ala
    130                 135                 140
Gln Ile Arg Lys Leu Thr Asp Met Glu Ala Gln Leu Leu Asn Gln Thr
145                 150                 155                 160
Ser Arg Met Asp Ala Gln Met Pro Glu Thr Phe Leu Ser Thr Asn Lys
                165                 170                 175
Leu Glu Asn Gln Leu Leu Leu Gln Arg Gln Lys Leu Gln Gln Leu Gln
            180                 185                 190
Gly Gln Asn Ser Ala Leu Glu Lys Arg Leu Gln Ala Leu Glu Thr Lys
        195                 200                 205
Gln Gln Glu Glu Leu Ala Ser Ile Leu Ser Lys Lys Ala Lys Leu Leu
    210                 215                 220
Asn Thr Leu Ser Arg Gln Ser Ala Ala Leu Thr Asn Ile Glu Arg Gly
225                 230                 235                 240
Leu Arg Gly Val Arg His Asn Ser Ser Leu Leu Gln Asp Gln His
                245                 250                 255
Ser Leu Arg Gln Leu Leu Val Leu Leu Arg His Leu Val Gln Glu Arg
            260                 265                 270
Ala Asn Ala Ser Ala Pro Ala Phe Ile Met Ala Gly Glu Gln Val
        275                 280                 285

<210> SEQ ID NO 11
<211> LENGTH: 879
<212> TYPE: DNA
<213> ORGANISM: Mus musculus

<400> SEQUENCE: 11
atgctctgcc agccagctat gctactagat ggcctcctcc tgctggccac catggctgca      60
gcccagcaca gagggccaga agccggtggg caccgccaga ttcaccaggt ccggcgtggc     120
cagtgcagct acacctttgt ggtgccggag cctgatatct gccagctggc gcgacagcg      180 gcgcctgagg cttttggggg ctccaatagc ctccagaggg acttgcctgc ctcgaggctg     240
cacctaacag actggcgagc ccagagggcc cagcgggccc agcgtgtgag ccagctggag     300
aagatactag agaataacac tcagtggctg ctgaagctgg agcagtccat caaggtgaac     360
ttgaggtcac acctggtgca ggcccagcag gacacaatcc agaaccagac aactaccatg     420
ctggcactgg gtgccaacct catgaaccag accaaagctc agacccacaa gctgactgct     480
gtggaggcac aggtcctaaa ccagacattg cacatgaaga cccaaatgct ggagaactca     540
ctgtccacca caagctgga gcggcagatg ctgatgcaga gccgagagct gcagcggctg     600
cagggtcgca cagggccct ggagaccagg ctgcaggcac tggaagcaca acatcaggcc     660
cagcttaaca gcctccaaga gaagagggaa caactgcaca gtctcctggg ccatcagacc     720
gggaccctgg ctaacctgaa gcacaatctg cacgctctca gcagcaattc cagctccctg     780
cagcagcagc agcagcaact gacggagttt gtacagcgcc tggtacggat tgtagcccag     840
gaccagcatc cggtttcctt aaagacacct aagccagtg                            879

<210> SEQ ID NO 12
<211> LENGTH: 861
<212> TYPE: DNA
<213> ORGANISM: Homo sapiens
```

<400> SEQUENCE: 12

```
atgctctccc agctagccat gctgcagggc agcctcctcc ttgtggttgc caccatgtct    60
gtggctcaac agacaaggca ggaggcggat aggggctgcg agacacttgt agtccagcac   120
ggccactgta gctacacctt cttgctgccc aagtctgagc cctgccctcc ggggcctgag   180
gtctccaggg actccaacac cctccagaga gaatcactgg ccaacccact gcacctgggg   240
aagttgccca cccagcaggt gaaacagctg gagcaggcac tgcagaacaa cacgcagtgg   300
ctgaagaagc tagagagggc catcaagacg atcttgaggt cgaagctgga gcaggtccag   360
cagcaaatgg cccagaatca gacggccccc atgctagagc tgggcaccag cctcctgaac   420
cagaccactg cccagatccg caagctgacc gacatggagg ctcagctcct gaaccagaca   480
tcaagaatgg atgcccagat gccagagacc tttctgtcca ccaacaagct ggagaaccag   540
ctgctgctac agaggcagaa gctccagcag cttcagggcc aaaacagcgc gctcgagaag   600
cggttgcagg ccctggagac caagcagcag gaggagctgg ccagcatcct cagcaagaag   660
gcgaagctgc tgaacacgct gagccgccag agcgccgccc tcaccaacat cgagcgcggc   720
ctgcgcggtg tcaggcacaa ctccagcctc ctgcaggacc agcagcacag cctgcgccag   780
ctgctggtgt tgttgcggca cctggtgcaa gaaagggcta acgcctcggc cccggccttc   840
ataatggcag gtgagcaggt g                                             861
```

<210> SEQ ID NO 13
<211> LENGTH: 503
<212> TYPE: PRT
<213> ORGANISM: Homo sapiens

<400> SEQUENCE: 13

```
Met Leu Ser Gln Leu Ala Met Leu Gln Gly Ser Leu Leu Val Val
1               5                   10                  15

Ala Thr Met Ser Val Ala Gln Gln Thr Arg Gln Glu Ala Asp Arg Gly
            20                  25                  30

Cys Glu Thr Leu Val Val Gln His Gly His Cys Ser Tyr Thr Phe Leu
        35                  40                  45

Leu Pro Lys Ser Glu Pro Cys Pro Pro Gly Pro Glu Val Ser Arg Asp
    50                  55                  60

Ser Asn Thr Leu Gln Arg Glu Ser Leu Ala Asn Pro Leu His Leu Gly
65                  70                  75                  80

Lys Leu Pro Thr Gln Gln Val Lys Gln Leu Glu Gln Ala Leu Gln Asn
                85                  90                  95

Asn Thr Gln Trp Leu Lys Lys Leu Glu Arg Ala Ile Lys Thr Ile Leu
            100                 105                 110

Arg Ser Lys Leu Glu Gln Val Gln Gln Met Ala Gln Asn Gln Thr
        115                 120                 125

Ala Pro Met Leu Glu Leu Gly Thr Ser Leu Leu Asn Gln Thr Thr Ala
    130                 135                 140

Gln Ile Arg Lys Leu Thr Asp Met Glu Ala Gln Leu Leu Asn Gln Thr
145                 150                 155                 160

Ser Arg Met Asp Ala Gln Met Pro Glu Thr Phe Leu Ser Thr Asn Lys
                165                 170                 175

Leu Glu Asn Gln Leu Leu Leu Gln Arg Gln Lys Leu Gln Gln Leu Gln
            180                 185                 190

Gly Gln Asn Ser Ala Leu Glu Lys Arg Leu Gln Ala Leu Glu Thr Lys
        195                 200                 205
```

```
        Gln Gln Glu Glu Leu Ala Ser Ile Leu Ser Lys Lys Ala Lys Leu Leu
            210                 215                 220

Asn Thr Leu Ser Arg Gln Ser Ala Ala Leu Thr Asn Ile Glu Arg Gly
        225                 230                 235                 240

Leu Arg Gly Val Arg His Asn Ser Ser Leu Leu Gln Asp Gln Gln His
                        245                 250                 255

Ser Leu Arg Gln Leu Leu Val Leu Leu Arg His Leu Val Gln Glu Arg
                    260                 265                 270

Ala Asn Ala Ser Ala Pro Ala Phe Ile Met Ala Gly Glu Gln Val Phe
                275                 280                 285

Gln Asp Cys Ala Glu Ile Gln Arg Ser Gly Ala Ser Ala Ser Gly Val
            290                 295                 300

Tyr Thr Ile Gln Val Ser Asn Ala Thr Lys Pro Arg Lys Val Phe Cys
        305                 310                 315                 320

Asp Leu Gln Ser Ser Gly Gly Arg Trp Thr Leu Ile Gln Arg Arg Glu
                        325                 330                 335

Asn Gly Thr Val Asn Phe Gln Arg Asn Trp Lys Asp Tyr Lys Gln Gly
                    340                 345                 350

Phe Gly Asp Pro Ala Gly Glu His Trp Leu Gly Asn Glu Val Val His
                355                 360                 365

Gln Leu Thr Arg Arg Ala Ala Tyr Ser Leu Arg Val Glu Leu Gln Asp
            370                 375                 380

Trp Glu Gly His Glu Ala Tyr Ala Gln Tyr Glu His Phe His Leu Gly
        385                 390                 395                 400

Ser Glu Asn Gln Leu Tyr Arg Leu Ser Val Val Gly Tyr Ser Gly Ser
                        405                 410                 415

Ala Gly Arg Gln Ser Ser Leu Val Leu Gln Asn Thr Ser Phe Ser Thr
                    420                 425                 430

Leu Asp Ser Asp Asn Asp His Cys Leu Cys Lys Cys Ala Gln Val Met
                435                 440                 445

Ser Gly Gly Trp Trp Phe Asp Ala Cys Gly Leu Ser Asn Leu Asn Gly
            450                 455                 460

Val Tyr Tyr His Ala Pro Asp Asn Lys Tyr Lys Met Asp Gly Ile Arg
        465                 470                 475                 480

Trp His Tyr Phe Lys Gly Pro Ser Tyr Ser Leu Arg Ala Ser Arg Met
                        485                 490                 495

Met Ile Arg Pro Leu Asp Ile
                    500
```

COMPOSITION COMPRISING AN ANGIOPOIETIN-4 FRAGMENT

CROSS-REFERENCE TO RELATED APPLICATIONS

This application is a continuation of U.S. patent application Ser. No. 10/558,539, filed on Oct. 11, 2006, issued as U.S. Pat. No. 8,232,247 on Jul. 31, 2012, which claims priority to and is a national stage application under 35 U.S.C. §371 of PCT International Application Serial Number PCT/US2004/016808, filed May 28, 2004, which claims priority to U.S. Provisional Application Ser. No. 60/473,998, filed May 29, 2003 and U.S. Provisional Application Ser. No. 60/479,802, filed Jun. 19, 2003, each of which is incorporated herein by reference in its entirety.

GOVERNMENT SUPPORT

This invention was made with U.S. Government support (NIH Grant No. 5R01HL074117) and the U.S. Government may therefore have certain rights in the invention.

FIELD OF THE INVENTION

The present invention is directed to methods of inhibiting angiopoietin-3 (Ang-3) and/or angiopoietin-4 (Ang-4, a human homolog of Ang-3), methods of identifying modulators of Ang-3 and/or of Ang-4, and methods of treatment using the same. The present invention is also directed to methods of treatment comprising administering Ang-3 and/or Ang-4.

BACKGROUND

Angiogenesis plays important roles in tumor growth and metastasis (Folkman, 1971, 1995; Hanahan and Folkman, 1996; Hanahan, 1997), and numerous molecules regulate angiogenesis (Ingber and Folkman, 1989; Folkman and D'Amore, 1996; Risau, 1997). Angiopoietins are ligands of Tie-2 receptor kinase which is primarily expressed by endothelial cells (ECs) and their precursors (Sato et al., 1993; Schnurch and Risau, 1993; Dumont et al., 1994). Three Tie-2 ligands have been identified (Davis et al., 1996; Maisonpierre et al., 1997; Valenzuela et al., 1999): angiopoietin-1, -2, and -3 (Ang-1, -2, and -3). Angiopoietin has a similar protein structure, which consists of a signal peptide, an amino terminal coiled-coil domain, a short linker peptide region, and a carboxyl terminal fibrinogen homology domain (FHD). The coiled-coil domain is responsible for dimerization/mulimerization of angiopoietin, while the FHD binds to Tie-2 receptor (Maisonpierre et al., 1997; Procopio et al., 1999; Valenzuela et al., 1999).

Studies have shown that Ang-1-Tie-2 pathway plays an essential role at the late stage of vascular development. Targeted disruption of Ang-1 or Tie-2 or overexpression of Ang-2 results in embryonic death with similar vascular defects. These mice displayed normal vascular growth factor (VEGF)-dependent early vascular development, but with profound defects in remodeling, organization, and stabilization of the primitive vasculature (Dumont et al., 1994; Sato et al., 1995; Suri et al., 1996; Maisonpierre et al., 1997).

At least under some circumstances, Ang-2 and Ang-3 are considered as naturally occurring antagonists of Tie-2 (Maisonpierre et al., 1997; Valenzuela et al., 1999). Ang-1 activates Tie-2 receptor by inducing tyrosine phosphorylation of Tie-2 and promotes recruitment of pericytes and smooth muscle cells. Thus, Ang-1 plays an important role in establishing and maintaining vascular integrity. As antagonists of Tie-2, Ang-2 and Ang-3 are believed to compete with Ang-1 for binding of Tie-2 and to block Tie-2 phosphorylation induced by Ang-1 (Maisonpierre et al., 1997; Valenzuela et al., 1999; Yancopoulos et al., 2000). It is well documented that angiogenesis is regulated by balanced activities of pro- and anti-angiogenic factors (Hanahan and Folkman, 1996; Risau, 1997; Hanahan, 1997). The existence of these antagonists underscores importance for precise regulation of Tie-2 activity.

It has been shown that VEGF and angiopoietin-Tie-2 pathways are independent and essential for tumor angiogenesis (Lin et al., 1997, 1998; Siemeister et al., 1999). Recent data showed that Ang-1 and Ang-2 are expressed by tumor cells and involved in tumor angiogenesis (Stratmann et al., 1998; Yu and Stamenkovic, 2001; Ahmad et al., 2001; Etoh et al., 2001; Hawighorst et al., 2002). However, the function of Ang-3 in general and the role of Ang-3 in tumor angiogenesis and metastasis have not been established.

Angiogenesis has also been tied to other vascular disorders such as, diabetes and arthritis, for which there is a need for the development of better treatments.

Thus, there is a need to identify the function and role of Ang-3 in tumor angiogenesis and metastasis. There is also a need for methods of identifying modulators of Ang-3 activity. There is also a need in the art for methods of treating individuals with cancer and other diseases related to uncontrolled angiogenesis and caused by lacking of angiogenesis and poor vascular endothelial cell health. The present invention fulfills these needs and others.

SUMMARY OF THE INVENTION

The present invention relates to methods of identifying inhibitors of Ang-3 or Ang-4 activity. The methods comprise contacting, in the presence of a test compound, endothelial cells with cells comprising Ang-3 or Ang-4; determining the level of endothelial cell retraction, level of loss of integrity, level of proliferation or level of apoptosis; and comparing the determined level with the level observed when endothelial cells are contacted with cells comprising Ang-3 or Ang-4 tethered to HSPG in the absence of test compound; wherein the reduction in the level of endothelial cell retraction, reduction in the level of loss of integrity, increase in the level of proliferation or reduction in the level of apoptosis indicates the test compound inhibits Ang-3 or Ang-4.

The present invention further relates to methods of identifying modulators of Ang-3 or Ang-4 binding with HSPGs. The methods comprise contacting, in the presence of a test compound, Ang-3 or Ang-4 with HSPG; determining the level of Ang-3 or Ang-4 binding HSPG; and comparing the determined level with the level observed when Ang-3 or Ang-4 is contacted with HSPG in the absence of test compound; wherein the reduction in the level of Ang-3-HSPG or Ang-4-HSPG binding indicates the test compound is an inhibitor of Ang-3-HSPG or Ang-4-HSPG binding and the increase in the level of Ang-3-HSPG or Ang-4-HSPG binding indicates the test compound is an enhancer of Ang-3-HSPG or Ang-4-HSPG binding.

The present invention further relates to methods of treating an individual who has cancer comprising the step of administering to said individual an amount of Ang-3 or Ang-4 or a nucleic acid molecule encoding Ang-3 or Ang-4 in an expressible vector to inhibit angiogenesis, spontaneous metastasis or conversion from micrometastasis to macrometastsis.

The present invention further relates to methods of treating an individual who has arthritis or diabetes comprising the step of administering to said individual an amount of Ang-3 or Ang-4 or a nucleic acid molecule encoding Ang-3 or Ang-4 in an expressible vector to inhibit angiogenesis.

The present invention further relates to methods of blocking endothelial cell proliferation comprising the step of delivering to an endothelial cell an amount of Ang-3 or Ang-4 or nucleic acid encoding Ang-3 or Ang-4 in an expressible vector to inhibit cell proliferation.

The present invention further relates to methods of inhibiting endothelial cell retraction or loss of integrity comprising the step of delivering to an endothelial cell an amount of an Ang-3 or Ang-4 inhibitor to inhibit endothelial cell retraction or loss of integrity.

The present invention further relates to methods of treating an individual who has vascular disease comprising the step of administering to said individual an amount of Ang-3 or Ang-4 inhibitor effective to promote endothelial cell proliferation and/or inhibit endothelial cell retraction and/or loss of integrity.

The present invention further relates to methods of treating an individual who has had a stroke or angioplasty comprising the step of administering to said individual an amount of Ang-3 or Ang-4 inhibitor effective to promote endothelial cell proliferation and/or inhibit endothelial cell retraction and/or loss of integrity.

The present invention further relates to methods of anchoring a protein to a cell surface comprising producing a fusion protein that comprises Ang-3 or Ang-4 or an HSPG-binding fragment thereof.

The present invention further relates to methods of diagnosing restenosis, artherosclerosis, hemorrhage or stroke comprising measuring levels of Ang-3 or Ang-4 and/or Ang-1 in a sample from an individual and comparing the levels to the levels found in normal individuals wherein elevated levels of Ang-3 or Ang-4 and/or depressed levels of Ang-1 indicate the possibility of a condition associate with endothelial cells such as restenosis, artherosclerosis, hemorrhage heart attack, or stroke.

The present invention further relates to methods of developing a prognosis for an individual who has been diagnosed with restenosis, artherosclerosis, hemorrhage heart attack or stroke comprising measuring levels of Ang-3 or Ang-4 and/or Ang-1 in a sample from an individual and comparing the levels to the levels found in normal individuals and individuals with varying severity of disease.

BRIEF DESCRIPTION OF FIGURES

FIG. 4. The coiled-coil domain of Ang-3 mediates its binding to the cell surface. Several expression constructs containing full-length of Ang-3 (1, lane 1 in B) or deleted Ang-3 were made. The deleted Ang-3 constructs include the coiled-coil domain plus the linker peptide region (2, lane 2 in B), the coiled-coil domain (3, lane 3 in B), and the linker peptide region plus FHD (4, lane 4 in B) of Ang-3. These expression constructs were used to transfect Cos-7 cells. 72 hours after the transfection, the cells were treated with (B-c) or without (B-b) trypsin, washed, and lysed. 50 μg of proteins derived from the cell culture supernatants (B-a) and the cell lysates (B-b, c) were analyzed by Western blotting with anti-v5 mAb.

DETAILED DESCRIPTION

Figure 1A:
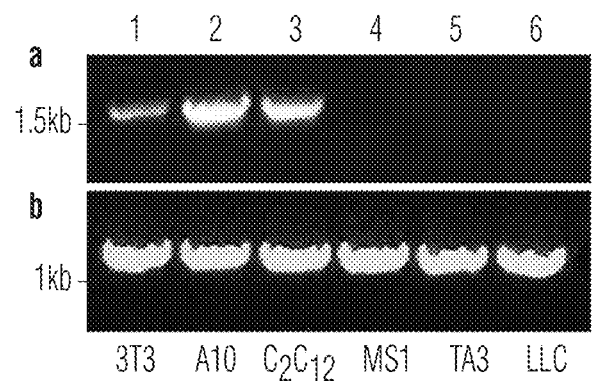
FIG. 1. Ang-3 is expressed by vascular smooth muscle cells and is associated to the cells. A. Expression of Ang-3 is assessed by RT-PCR using RNAs derived from 3T3 fibroblasts, A10 vascular smooth muscle cells, $C_2C_{12}$ myoblasts, MS1 ECs, and TA3 and LLC cells (A-a, lanes 1-6). Expression of β-actin by these cells was used as a control (A-b). B. Western blot was performed under non-reducing condition using anti-v5 mAb to determine the distribution patterns of v5-epitope tagged Ang-1, Ang-2, and Ang-3 proteins in the cell culture supernatants (B-a), the ECM (B-b), and the EDTA-lifted LLC transfectants (B-c) expressing Ang-1 (lanes 1-2), Ang-2 (lanes 3-4), or Ang-3 (lanes 5-6). KDa stands for kilodalton.

"Angiopoietin-3" or "Ang-3" has been previously described in mouse and human (see, for example, Venezuela et al., PNAS 1999 Mar. 2; 96(5):1904-9; Kim et al. FEBS Lett. 1999 Jan. 29; 443(3):353-6; and Nishimura et al. FEBS Lett. 1999 Apr. 9; 448(2-3):254-6; each of which is herein incorporated by reference). The nucleotide sequence encoding murine Ang-3 comprises SEQ ID NO:1. The amino acid sequence of murine Ang-3 comprises SEQ ID NO:2. A homolog of Ang-3 identified in humans is referred to as Angiopoietin-4 (Ang-4). The nucleic acid coding sequence of Ang-4 is disclosed in Genbank Accession Number NM 015985 and AF074332, which are both incorporated by reference, and Valenzuela et al. PNAS USA 96:1904-1909 (1999), which is incorporated herein by reference. The nucleic acid molecule sequence encoding human Ang-4 comprises SEQ ID NO:3. The amino acid sequence of human Ang-4 encoded by SEQ ID NO:3 is SEQ ID NO:13. The amino acid sequence of human Ang-4 comprises SEQ ID NO:4.

Ang-3 and Ang-4 have been found to be potent inhibitors of angiogenesis and vascularization. The findings described below demonstrate that Angiopoietins not only play different roles in regulating EC function and angiogenesis, but also the functions of angiopoietins are differentially regulated by the ECM and the cell surface HSPGs, which can provide the basis for modulating the activities of angiopoietins in vivo, therefore, regulating endothelial cell functions and angiogenesis in physiologic and pathologic situations. Ang-3 and Ang-4 have been found to have important roles in preventing tumor metastasis. The clinical applications of Ang-3 and Ang-4 can be used to treat diseases that involve angiogenesis or vascularization, such as cancer, diabetes, and arthritis.

The embodiments of the present invention include methods and compositions with Ang-3 and are equally applicable to the homolog Ang-4 and vice versa. For example, the present invention describes a method of identifying inhibitors of Ang-3. The same method can be used to identify inhibitors of the homolog of Ang-3, which is Ang-4. Thus, as set forth below, Ang-3 and Ag-4 may be used interchangeably.

The present invention arises from several novel findings which provide knowledge and targets to develop proteins, peptides, small molecules, inhibitors, and gene therapy approaches to regulate (inhibit or promote) activity and function of Angiopoietin-Tie-2 pathway, to treat patients with cancers by blocking angiogenesis, and with ischemia by inducing/promoting angiogenesis, with blood vessel blockage, stroke, hemorrhage, restenosis, and atherosclerosis as detailed below. Among the findings that the invention identified are:

1) Unlike angiopoietin-1 (Ang-1), which binds to the extracellular matrix (ECM), and angiopoietin-2 (Ang-2), which is primarily secreted, (Xu and Yu, 2001), angiopoietin-3 (Ang-3) is tethered on the surface of cells including non-endothelial cells via its coiled-coil domain.

2) The cell surface heparan sulfate proteoglycans (HSPGs) are a group of proteins that bind Ang-3 and Ang-4 on the cell surface.

3) The cell surface bound Ang-3 proteins but not soluble Ang-3 induces retraction and loss of integrity of endothelial monolayer, suggesting that the function of Ang-3 is regulated by its binding to the cell surface.

4) Like Ang-1, Ang-3 is primarily expressed by mesenchymal cells including vascular smooth muscle cells.

5) Overexpression of Ang-3 and Ang-4 blocks spontaneous pulmonary tumor metastasis by blocking angiogenesis in micrometastasis and progression of micrometastasis to life-threatening macrometastasis.

6) Ang-3 inhibits endothelial cell proliferation and promotes apoptosis of endothelial cells via blocking the activation of Erk1/2 and Akt kinases induced by Ang-1 and VEGF.

Several novel functions of Ang-3 and ANg-4 that may provide basis for modulating endothelial cells functions and angiogenesis in vivo in many pathologic situations.

Like Ang-1, Ang-3 is expressed by mesenchymal cells including vascular smooth muscle cells (FIG. 1A), and Ang-1 and Ang-3 displayed opposite effects on EC sprouting/retraction, proliferation, and survival (FIGS. 7-9). Loss of endothelial layer integrity is the root of many vascular diseases. Studies have shown that Ang-1 plays an important role in maintaining vascular integrity by promoting the interaction between endothelial cells and peri-endothelial mural cells and we have demonstrated that the cell surface tethered Ang-3 induces retraction a loss integrity of endothelial monolayer.

Thus, Ang-1 and Ang-3 represent two important factors produced by peri-endothelial cells and play antagonistic roles in maintaining health and integrity of functional blood vessels in adult tissues. The balanced activity of Ang-1 and Ang-3 is likely important for angiogenesis to establish functional blood vessels during embryogenesis and tissue repairing. Imbalanced up-regulation of Ang-3 expression and activity and/or down-regulation of Ang-1 expression and activity may contribute to vascular diseases such as atherosclerosis and restenosis. Our results predict that there may be up-regulation and/or down regulation of Ang-1 and/or Ang-3 at the early stages of restenosis, atherosclerosis, hemorrhage, and stroke, which may be used as diagnoses and prognosis tools and may also be used to treat these diseases and will be pursued in this laboratory.

The present invention can be used, therefore, to assist the recovery of the patients who had stroke and the angioplasty procedure by blocking activity of Ang-3 to promote the growth/survival of endothelial cells, and to block proliferation of vascular smooth muscle cells.

The present invention can also be used to treat patients with restenosis by inhibiting re-closure of blood vessel after inserting stents into blood vessels by blocking activity of Ang-3.

Ang-3 and Ang-4 inhibit spontaneous pulmonary tumor metastasis by blocking angiogenesis and promoting apoptosis of the tumor cells in micrometastasis. Ang-3 and Ang-4 can, thus, be used to achieve tumor dormancy and inhibit tumor metastasis. Ang-3 can also be used to effectively block angiogenesis in other pathologic situation, such as arthritis and complications caused by diabetes such as diabetic retinopathy.

Ang-3 proteins are tethered on the cell surface by the cell surface HSPGs including, for example, perlecan and the function of Ang-3 is regulated by the binding, which will allow us to modulate the availability and activity of Ang-3 proteins in the following potential ways. The present invention provides methods of modulating the binding of Ang-3 or Ang-4 to the cell surface HSPGs by administrating peptides or small molecules that block or enhance the binding or by administrating the coiled-coil fragment of Ang-3 or Ang-4.

Angiopoietin-3 (Ang-3) and Angiopoietin-3 (Ang-4) are involved in inhibiting angiogenesis and metastasis. Therefore, identifying modulators of Ang-3 activity would provide compounds that can be used to treat diseases, conditions, or disorders that require either an inhibition or activation of angiogenesis. Additionally, Ang-3 and/or Ang-4 can be supplied to an individual to treat metastasis.

The present invention provides methods of identifying inhibitors of Ang-3 and/or Ang-4 activity comprising contacting, in the presence of a test compound, endothelial cells with cells comprising Ang-3 and/or Ang-4; determining the level of endothelial cell retraction, level of loss of integrity, level of proliferation or level of apoptosis; and comparing the determined level with the observed level when endothelial cells are contacted with cells comprising Ang-3 and/or Ang-4 in the absence of the test compound, wherein a reduction in the level of endothelial cell retraction, reduction in the loss of integrity, increase in the level of proliferation or reduction in the level of apoptosis indicates that the test compound inhibits Ang-3 and/or Ang-4. In some embodiments, Ang-3 and/or Ang-4 is tethered to a heparan sulfate proteoglycan (HSPG). The HSPGs that tether Ang-3 and/or Ang-4 onto the cell surface include, for example, perlecan and/or syndecans including syndecan-1, -2, -3, and -4.

As used herein, "Ang-3 activity" or "Ang-4 activity" refers to any activity mediated by Ang-3 or Ang-4, respectively. In some embodiments, an Ang-3 or Ang-4 activity is endothelial cell retraction, level of loss of integrity, level of proliferation, or level of apoptosis (cell death), and the like. Ang-3 or Ang-4 activity can also be preventing angiogenesis or metastasis. In some embodiments, "Ang-3 activity" or "Ang-4 activity" refers to the binding of Ang-3 and/or Ang-4, respectively, to HSPGs. An Ang-3 or Ang-4 activity can also be the binding of another compound or protein to Ang-3 or Ang-4, respectively.

An "inhibitor of Ang-3 activity" or "inhibitor of Ang-4 activity" can refer to any molecule that inhibits an activity of Ang-3 or Ang-4, respectively. In some embodiments, an inhibitor of Ang-3 or Ang-4 activity is a small molecule, a nucleic acid molecule, a peptide, a polypeptide, a protein, an antibody, and the like.

In some embodiments, "a test compound" is a small molecule, a nucleic acid molecule, a peptide, a polypeptide, a protein, an antibody, and the like.

As used herein, "cells comprising Ang-3 tethered to a heparan sulfate proteoglycan" or "cells comprising Ang-4 tethered to a heparan sulfate proteoglycan" refers to cells that have Ang-3 or Ang-4 protein, respectively, tethered to a heparan sulfate proteoglycan (HSPG). HSPGs are cell surface molecules that can be used to tether and/or localize another protein to the surface. HSPGs are also involved in a wide array of signaling pathways. In some embodiments, the cell comprising Ang-3 or Ang-4 tethered to a heparan sulfate proteoglycan endogenously produced Ang-3 or Ang-4, respectively, and is normally tethered to a HSPG. However, the Ang-3 or Ang-4 can be exogenously be added to a cell by transfecting or transforming a cell with a nucleic acid molecule encoding Ang-3 or Ang-4, respectively. The nucleic acid molecule can express Ang-3 in the cell and allow it to be tethered to a HSPG. In some embodiments, HSPG is also exogenously added to the cell so that a cell that does not normally comprise Ang-3 or Ang-4 tethered to HSPG can express and comprise Ang-3 or Ang-4 tethered to HSPG.

As used herein, the term "tether" refers to molecules interacting with one another either through covalent or non-covalent interactions. In some embodiments, the interaction is reversible or irreversible.

Ang-3 or Ang-4 can be exogenously be added to a cell by transfecting or transforming a cell with a nucleic acid molecule encoding Ang-3 or Ang-4, respectively. The nucleic acid molecule can express Ang-3 or Ang-4. Isolated or purified Ang-3 or Ang-4 protein can also be added to a cell or a solution of cells so that the Ang-3 or Ang-4 protein is contacted with the cell or cell population. In some embodiments, the Ang-3 or Ang-4 is produced recombinantly. In some embodiments, the protein is produced in a bacterial cell or a eukaryotic cell. In some embodiments, Ang-3 or Ang-4 is tethered to HSPG.

One of skill in the art can readily determine the level of endothelial cell retraction, level of loss of integrity, level of proliferation or level of apoptosis using routine experimentation and methods that are known to one of skill in the art. For example, the level of apoptosis or cell death can be determined using a TUNEL assay or other assays that measure cell viability. Level of proliferation can be determined, for example, by counting the number of cells in a sample and seeing at what rate the cell number increases, decreases or remains constant. Loss of integrity can be determined, for example, by visualizing the cells or using markers to test blood vessel integrity (e.g. dyes that can leak out from a blood vessel that has lost integrity). The level of endothelial cell retraction can also be determined by routine experimentation.

A test compound is considered to be an inhibitor of Ang-3 or Ang-4 activity if it reduces the activity of the Ang-3 or Ang-4 protein, which can include, but is not limited to, a reduction in the level of endothelial cell retraction, level of loss of integrity, level of proliferation or level of apoptosis. In some embodiments, a test compound is considered to be an inhibitor of Ang-3 or Ang-4 activity if it reduces Ang-3 or Ang-4 activity by at least 10%, by at least 20%, by at least 30%, by at least 40%, by at least 50%, by at least 60%, by at least 70%, by at least 80%, by at least 90%, by at least 95%, or by at least 100%.

Ang-3 or Ang-4 is secreted and found to be bound at the cell surface by binding to HSPGs. Therefore, another way to modulate the activity of Ang-3 or Ang-4 is to identify modulators of Ang-3 or Ang-4 binding with HSPGs. Accordingly, the present invention provides methods of identifying modulators of Ang-3 or Ang-4 binding with HSPGs. In some embodiments, the method comprises contacting, in the presence of a test compound, Ang-3 or Ang-4 with HSPG; determining the level of Ang-3 or Ang-4 binding HSPG; and comparing the determined level with the level observed when Ang-3 or Ang-4 is contacted with HSPG in the absence of the test compound. If the level of Ang-3-HSPG or Ang-4-HSPG binding is reduced in the presence of the test compound, then the reduction in binding indicates that the test compound is an inhibitor of Ang-3-HSPG or Ang-4-HSPG binding, respectively. If the level of Ang-3-HSPG or Ang-4-HSPG binding is increased in the presence of the test compound, then the increase in binding indicates that the test compound is an enhancer or activator of Ang-3-HSPG or Ang-4-HSPG binding, respectively.

In some embodiments, the binding of Ang-3 or Ang-4 and HSPG is measured in vitro or in vivo. In some embodiments, the Ang-3 or Ang-4 is produced recombinantly, isolated from a cell (e.g. bacterial or eukaryotic), or isolated from an animal.

In some embodiments, a test compound is considered to a be a modulator of Ang-3-HSPG or Ang-4-HSPG binding if the test compound increases or decreases Ang-3-HSPG or Ang-4-HSPG binding by at least 10%, at least 20%, at least 30%, at least 40%, at least 50%, at least 60%, at least 70%, at least 80%, at least 90%, at least 95%, or at least 100%.

Ang-3 and Ang-4 have also been found to be able to inhibit the spread of cancer by inhibiting angiogenesis, metastasis, or conversion from micrometastasis to macrometastasis. Accordingly, the present invention provides methods of treating an individual who has cancer comprising administering to the individual an amount of Ang-3 or Ang-4 protein or a nucleic acid molecule encoding Ang-3 or Ang-4 in an expressible vector to inhibit angiogenesis, spontaneous metastasis, or conversion from micrometastasis to macrometastasis.

In some embodiments, the amount that is administered is a therapeutically effective amount. As used herein, the term "therapeutically effective amount" is meant to refer to an amount of Ang-3 or Ang-4 protein or a nucleic acid encoding Ang-3 or Ang-4 which produces a clinical effect observed as inhibiting angiogenesis, spontaneous metastasis, or conversion from micrometastasis to macrometastasis in an individual when a therapeutically effective amount of an Ang-3 or Ang-4 protein or a nucleic acid molecule encoding Ang-3 or Ang-4 is administered to an individual or to a cell. Therapeutically effective amounts are typically determined by the effect they have compared to the effect observed when a composition which includes no active ingredient is administered to a similarly situated individual. The precise effective amount for a subject will depend upon the subject's size and health, the nature and extent of the condition, and the therapeutics or combination of therapeutics selected for administration. However, the effective amount for a given situation is determined by routine experimentation and is within the judgment of the clinician.

An "Ang-3 protein" can also refer to a fragment of Ang-3 protein. A "fragment" can refer to a protein that is either less than the complete Ang-3 protein or the complete Ang-3 protein. In some embodiments, a fragment of Ang-3 comprises at least 5, at least 10, at least 20, at least 30, at least 40, at least 50, at least 60, at least 70, at least 80, at least 90, at least 100, at least 150, at least 200, or at least 300 amino acid residues.

An "Ang-4 protein" can also refer to a fragment of Ang-4 protein. A "fragment" can refer to a protein that is either less than the complete Ang-3 protein or the complete Ang-4 protein. In some embodiments, a fragment of Ang-4 comprises at least 5, at least 10, at least 20, at least 30, at least 40, at least 50, at least 60, at least 70, at least 80, at least 90, at least 100, at least 150, at least 200, or at least 300 amino acid residues.

As used herein, "an expressible vector" refers to a composition comprising a nucleic acid molecule that is able to express a gene or protein of interest. In some embodiments, the expressible vector is a DNA molecule, or a RNA molecule. A "DNA molecule" or a "RNA molecule" can refer to the genetic component of a virus. The virus can be, for example, a DNA virus, a RNA virus. examples of viruses include a retrovirus, adenovirus, adeno-associated virus, and the like. In some embodiments, the DNA molecule is a plasmid or linear DNA. In some embodiments, the expressible vector is free of infectious agents.

According to the present invention, DNA or RNA that encodes Ang-3 or Ang-4 is introduced into the cells of an individual where it is expressed, thus producing Ang-3 or Ang-4. The DNA or RNA can be linked to regulatory elements necessary for expression in the cells of the individual. Regulatory elements for DNA include a promoter and a polyadenylation signal. In addition, other elements, such as a Kozak region, may also be included in the nucleic acid molecule.

As used herein, the term "nucleic acid molecule" refers to the DNA or RNA molecule that comprises a nucleotide sequence which encodes Ang-3, Ang-4 or fragment thereof and which includes initiation and termination signals operably linked to regulatory elements including a promoter and polyadenylation signal capable of directing expression in the cells of the vaccinated individual. As used herein, the term "expressible form" refers to nucleic acid molecules which contain the necessary regulatory elements operable linked to a coding sequence that encodes Ang-3, Ang-4 or a fragment thereof, such that when present in the cell of the individual, the coding sequence will be expressed.

The nucleic acid molecules comprise a nucleotide sequence that encodes a target protein operably linked to regulatory elements needed for gene expression. Accordingly, incorporation of the DNA or RNA molecule into a living cell results in the expression of the DNA or RNA encoding the target protein and thus, production of the target protein.

When taken up by a cell, the nucleic acid molecule, which includes the nucleotide sequence encoding the target protein operably linked to the regulatory elements, may remain present in the cell as a functioning extrachromosomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the nucleic acid molecule. Alternatively, RNA may be administered to the cell or individual.

The elements of a nucleic acid molecule include a nucleotide sequence that encodes a Ang-3 or Ang-4 and the regulatory elements necessary for expression of that sequence in the cells of the individual. The regulatory elements are operably linked to the DNA sequence that encodes the Ang-3 or Ang-4 protein to enable expression.

The molecule that encodes Ang-3, Ang-4 or fragment thereof is a protein-encoding molecule which is translated into protein. Such molecules include DNA or RNA which comprise a nucleotide sequence that encodes the target protein. These molecules may be cDNA, genomic DNA, synthesized DNA or a hybrid thereof or an RNA molecule such as mRNA.

The regulatory elements necessary for gene expression of a DNA molecule include: a promoter, an initiation codon, a stop codon, and a polyadenylation signal. In addition, enhancers are often required for gene expression. It is necessary that these elements be operable in the treated individual. Moreover, it is necessary that these elements be operably linked to the nucleotide sequence that encodes Ang-3 or Ang-4 such that the nucleotide sequence can be expressed in the cells of an individual and thus Ang-3 or Ang-4 can be produced.

Initiation codons and stop codon are generally considered to be part of a nucleotide sequence that encodes the Ang-3 or Ang-4 protein.

Similarly, promoters and polyadenylation signals used must be functional within the cells of the individual.

Examples of promoters useful to practice the present invention include, but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human elongation factor (pEF), human Actin, human Myosin, human Hemoglobin, human muscle creatine and human metalothionein.

Examples of polyadenylation signals useful to practice the present invention include, but are not limited to, SV40 polyadenylation signals and LTR polyadenylation signals.

In addition to the regulatory elements required for DNA expression, other elements may also be included in the DNA molecule. Such additional elements include enhancers. The enhancer may be selected from the group including but not limited to: human elongation factor, human Actin, human Myosin, human Hemoglobin, human muscle creatine and viral enhancers such as those from CMV, RSV and EBV.

Nucleic acid molecules can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

In order to maximize protein production, regulatory sequences may be selected which are well suited for gene expression in the treated cells or individual. Moreover, codons may be selected which are most efficiently transcribed in the treated cell or individual. One having ordinary skill in the art can produce DNA constructs which are functional in treated cells or individuals.

In order to test expression, nucleic acid molecules can be tested for expression levels in vitro using tissue culture of cells of the same type as those to be vaccinated. For example, if the nucleic acid molecule is to be administered into human breast or lung cells, breast or lung cells grown in culture may be used as an in vitro model to measure expression level.

"Angiogenesis" refers to the growth of blood vessels. In some embodiments, "angiogenesis" refers to the growing of blood vessels in terms of cancer or stroke.

As used herein, the term "conversion from micrometastasis to macrometastasis" refers to a cancer that has metastasized, but which the tumor size at the various points of spreading is small and does not affect the function of the organs. When the metastasized cancer grows in size this is referred to as the conversion of the micrometastasis to macrometastasis.

In some embodiments, the individual being treated has lung cancer or breast cancer.

The present invention also provides methods of treating an individual who has arthritis or diabetes comprising the step of administering to the individual an amount of Ang-3 or Ang-4 or a nucleic acid molecule encoding Ang-3 or Ang-4 in an expressible vector to inhibit angiogenesis.

In some embodiments, "an amount of Ang-3 or Ang-4 or a nucleic acid molecule encoding Ang-3 or Ang-4 in an expressible vector" refers to a HSPG binding fragment of Ang-3 or Ang-4 or a nucleic acid molecule encoding a HSPG binding fragment of Ang-3 or Ang-4.

In some embodiments, inhibitors of Ang-3 or Ang-4 are combined with modified Ang-1 molecules which are described in U.S. application Ser. No. 10/375,765 and U.S. application Ser. No. 10/789,222, each of which is incorporated herein by reference.

The present invention also provides methods of blocking endothelial cell proliferation comprising the step of delivering to an endothelial cell an amount of Ang-3 or Ang-4 or a nucleic acid molecule encoding Ang-3 or Ang-4 in an expressible vector to inhibit cell proliferation.

As used herein, the term "blocking" can mean reducing or inhibiting an event by 100% or less than 100%. In some embodiments, a process is blocked if it is reduced or inhibited by 100%, at least 95%, at least 90%, at least 80%, at least 70%, at least 60%, at least 50%, at least 40%, at least 30%, at least 20%, or at least 10%.

The present invention also provides methods of inhibiting endothelial cell retraction or loss of integrity comprising the step of delivering to an endothelial cell an amount of Ang-3 or Ang-4 inhibitor to inhibit endothelial cell retraction or loss of integrity.

In some embodiments, the Ang-3 or Ang-4 inhibitor of the present invention is an anti-Ang3 or Ang-4 antibody. The term "antibody" encompasses polyclonal and monoclonal antibody preparations, as well as preparations including hybrid antibodies, altered antibodies, chimeric antibodies, and humanized antibodies. Examples of anti-Ang3 or Ang-4 antibodies include, but are not limited to, monoclonal antibodies, polyclonal antibodies, chimeric antibodies, humanized antibodies, and the like. A "chimeric antibody" combines DNA encoding regions from more than one type of species. For example, a chimeric antibody may derive the variable region from a mouse and the constant region from a human. A "humanized antibody" comes predominantly from a human, even though it contains nonhuman portions. Like a chimeric antibody, a humanized antibody may contain a completely human constant region. But unlike a chimeric antibody, the variable region may be partially derived from a human. The nonhuman, synthetic portions of a humanized antibody often come from CDRs in murine antibodies. As used herein the term "monoclonal antibody" means an antibody composition having a homogeneous antibody population. It is not intended to be limited as regards the source of the antibody or the manner in which it is made.

The present invention also provides methods of treating an individual who has vascular disease comprising the step of administering to the individual an amount of an Ang-3 or Ang-4 inhibitor effective to promote endothelial cell proliferation and/or inhibit endothelial cell retraction and/or loss of integrity.

As used herein "loss of integrity of endothelial monolayer" refers to a monolayer of endothelial cells that is no longer structurally as a monolayer. lost EC monolayer integrity may, for example, have endothelial cell-cell junction broken, has holes between endothelial cells, which allows leakage of the contents in blood vessels.

Examples of vascular disease that can be treated include, but are not limited to, artherosclerosis, restenosis, and the like. Examples of restenosis, include but are not limited to, restenosis associated with angioplasty, stent implantation, and the like.

The present invention also includes methods of treating an individual who has had a stroke or angioplasty comprising the step of administering to the individual an amount of an Ang-3 or Ang-4 inhibitor effective to promote endothelial cell proliferation and/or inhibit endothelial cell retraction and/or loss of integrity.

The present invention also provides methods of anchoring proteins to a cell surface comprising producing a fusion protein that comprises Ang-3, Ang-4 or an HSPG-binding fragment thereof. As used herein, a "fusion protein" refers to a protein comprising regions from two different proteins. This fusion protein can, for example, serve as an anchoring or localizing protein of proteins that are not normally anchored or localized to the cell membrane.

"An HSPG-binding fragment" of Ang-3 or Ang-4 refers to a portion of Ang-3 or Ang-4 that is necessary to bind to an HSPG. One of skill in the art can determine what is an HSPG-binding fragment using routine experimentation. For example, an HSPG-binding fragment can be identified by measuring the binding of Ang-3 or Ang-4 to an HSPG using different fragments of Ang-3 or Ang-4. In some embodiments, the HSPG-binding fragment of Ang-3 or Ang-4 comprises about 5, about 10, about 20, about 30, about 40, about 50, about 60, about 70, about 80, about 90, about 100, about 150, about 200, about 300, or about 400 amino acid residues. In some embodiments, an HSPG-binding fragment of Ang-3 or Ang-4 comprises the coiled-coil region of Ang-3 or Ang-4. In some embodiments, the HSPG-binding fragment comprises of Ang-3 or Ang-4 comprises SEQ ID NO:5 or SEQ ID NO:6, respectively. In some embodiments, a nucleotide sequence encoding a HSPG-binding fragment of Ang-3 or Ang-4 comprises SEQ ID NO: 7 or SEQ ID NO:8, respectively. In some embodiments, the HSPG-binding fragment of Ang-3 or Ang-4 comprises the linker peptide plus the coiled-coil region. In some embodiments, the HSPG-binding fragment comprising the linker peptide plus the coiled-coil region of Ang-3 or Ang-4 comprises SEQ ID NO: 9 or SEQ ID NO: 10, respectively. In some embodiments a nucleotide sequence encoding the HSPG-binding fragment comprising the linker peptide plus the coiled-coil region of Ang-3 or Ang-4 comprises SEQ ID NO: 11 or SEQ ID NO: 12, respectively.

As used herein, the term "coiled-coil region" refers to a region of a protein having a structure that one of ordinary skill in the art refers to as a coiled-coil region. In some embodiments, the "SP region" in human and mouse Ang-3/Ang-4 refers to the first 20 amino acids. In some embodiments, the coiled-coil region in human is residues 62-263 of Ang-4, and in mouse is 65-272 of Ang-3. In some embodiments, the linker domain in human Ang-4 is 264-287 and in mouse Ang-3 is 273-293. In some embodiments, the FHD in human Ang-4 is 288-503 and in mouse Ang-3 is 294-509. In some embodiments, the HSPG binding fragment of Ang-3 comprises amino acids 1-272 of Ang-3. In some embodiments, the HSPG binding fragment of Ang-4 comprises amino acids 1-263 of Ang-4.

As used herein, the term "about" refers to +/−30%, +/−20%, +/−10%, or +/−5% of a value.

The present invention also provides methods of diagnosing restenosis, artheroscherosis, hemorrhage or stroke comprising measuring levels of Ang-3 and/or Ang-4 in a sample from an individual and comparing the levels to the levels found in normal individuals wherein elevated levels of Ang-3 or Ang-4 and/or depressed levels of Ang-1 indicate the possibility of a condition associated with endothelial cells such as restenosis, artheroscherosis, hemorrhage, heart attack or stroke.

In some embodiments, the levels of Ang-3 or Ang-4 are elevated about 10%, about 20%, about 30%, about 40%, about 50%, about 60%, about 70%, about 80%, about 90%, or about 100%. In some embodiments, the levels of Ang-3 are elevated at least 10%, at least 30%, at least 50%, at least 60%, at least 70%, at least 80%, at least 90%, or at least 100%.

In some embodiments, the levels of Ang-1 are depressed by at least 10%, at least 20%, at least 30%, at least 40%, at least 50%, at least 60%, at least 70%, at least 80%, at least 90%, or at least 100%. In some embodiments, the levels of Ang-1 are depressed by about 10%, about 20%, about 30%, about 40%, about 50%, about 60%, about 70%, about 80%, about 90%, or about 100%.

The present invention also provides methods of developing a prognosis for an individual who has been diagnosed with restenosis, artheroscherosis, hemorrhage, heart attack, or stroke comprising measuring levels of Ang-3, Ang-4 and/or Ang-1 in a sample from an individual and comparing the levels found in normal individuals and individuals with varying severity of disease.

As used herein, the term "contacting" refers to the bringing together of indicated moieties in an in vitro system or an in vivo system.

As used herein, the term "individual" or "patient," used interchangeably, refers to any animal, including mammals, for example, mice, rats, other rodents, rabbits, dogs, cats, swine, cattle, sheep, horses, or primates, (e.g. humans).

As used herein, the term "cell" refers to a cell that is either in vivo, in vitro, or ex vivo.

Pharmaceutical Formulations and Dosage Forms Pharmaceutical Formulations and Dosage Forms When employed as pharmaceuticals, the modulators, activators, inhibitors, enhancers of Ang-3 or Ang-4 activity, nucleic acid molecules encoding Ang-3, Ang-4 or a fragment thereof, polypeptides comprising Ang-3 or a fragment thereof of the present invention can be administered in the form of pharmaceutical compositions. These compositions can be administered by a variety of routes including oral, rectal, transdermal, subcutaneous, intravenous, intramuscular, and intranasal, and can be prepared in a manner well known in the pharmaceutical art.

This invention also includes pharmaceutical compositions which contain, as the active ingredient, one or more of modulators, activators, inhibitors, enhancers of Ang-3 activity, nucleic acid molecules encoding Ang-3, Ang-4 or a fragment thereof, polypeptides comprising Ang-3, Ang-4 or a fragment thereof above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, or about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as a chemotherapeutic or other biologic used to treat cancer, anti-viral agents, antibiotics, antibodies, immune suppressants, anti-inflammatory agents, and the like. In some embodiments, the compounds of the invention are formulated in combination with one or more chemotherapeutics and other agents used for treating cancer, diabetes, stroke, arthritis, restenosis, and the like.

In order that the invention disclosed herein may be more efficiently understood, examples are provided below. It should be understood that these examples are for illustrative purposes only and are not to be construed as limiting the invention in any manner.

EXAMPLES

Example 1: Function and Activity of Ang-3

The role of Ang-3 in tumor angiogenesis and metastasis, and the mechanism underlying its function was investigated. We demonstrated that like Ang-1, Ang-3 is expressed by vascular smooth muscle cells (FIG. 1A); and that unlike Ang-1, which binds to the extracellular matrix (ECM), and Ang-2, which is secreted, Ang-3 is tethered on the cell surface by cell surface heparan sulfate proteoglycans (HSPGs) via its coiled-coil domain. Furthermore, we have demonstrated that overexpression of Ang-3 inhibits pulmonary metastasis of Lewis lung carcinoma (LLC) and TA3 mammary carcinoma (TA3) cells by inhibiting tumor angiogenesis and progression of pulmonary micrometastases to life-threatening macrometastases. In addition, we demonstrated that cell surface binding of Ang-3 is required for effective inhibition of pulmonary metastasis of LLC and TA3 cells mediated by Ang-3. We demonstrated that cell-surface bound but not soluble Ang-3 induces retraction and loss of integrity of endothelial monolayer, and Ang-3 inhibits EC proliferation and survival and blocks Ang-1- and VEGF-induced activation of Erk1/2 and Akt kinase, which likely underlie the Ang-3-mediated inhibition of tumor angiogenesis and metastasis.

Results

Unlike Ang-1 and Ang-2, Ang-3 is Retained on the Surface of Various Cells

To determine which cell types express Ang-3, we performed RT-PCR using RNAs derived from several different cell lines. Our result showed that like Ang-1, Ang-3 is expressed primarily by mesenchymal cells including vascular smooth muscle cells (FIG. 1A). It was noted previously that it was difficult to produce and purify Ang-1 and Ang-3 proteins (Maisonpierre et al., 1997; Valenzuela et al., 1999).

Figure 1B:
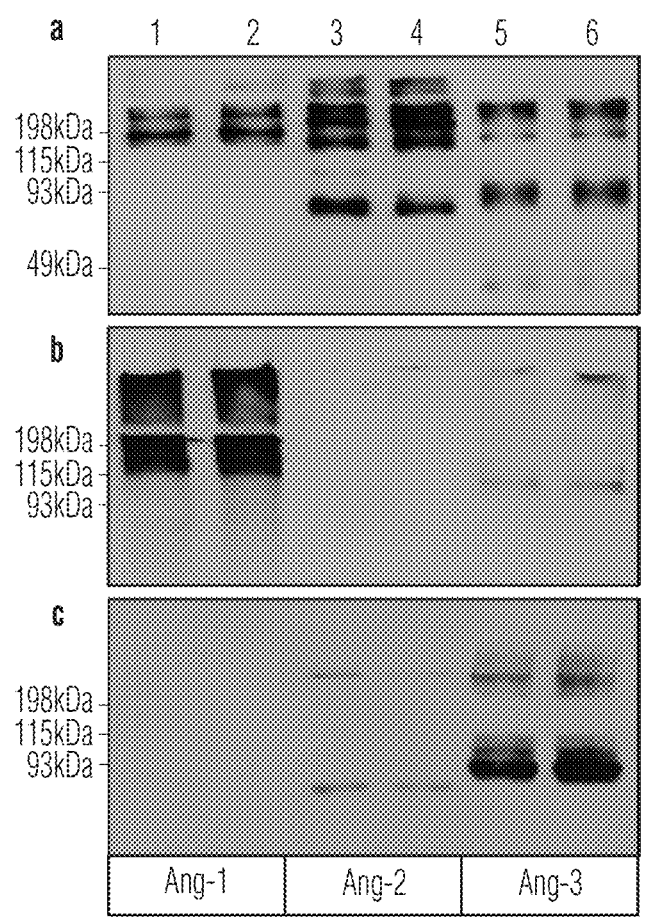

We have shown recently that Ang-1 is secreted and incorporated into the ECM (Xu and Yu, 2001). To determine whether Ang-3 binds to the ECM as well, we investigated the distribution of Ang-3 protein in the established LLC transfectants expressing the v5 epitope tagged Ang-3 (Ang-3v5). v5 epitope is a 14 amino acid epitope derived from P and V proteins of the paramyxovirus, SV5 (Southern et al., 1991, Invitrogen). The proteins analyzed by Western blotting with anti-v5 monoclonal antibody (mAb) were derived from the culture supernatants, the ECM materials deposited on the cell culture dishes, and the EDTA-lifted LLC transfectants expressing v5-tagged Ang-1 (LLCAng-1), -2 (LLCAng-2), or -3 (LLCAng-3). The results showed that Ang-2 is largely secreted, Ang-1 binds to the ECM, and Ang-3 is associated with the transfected cells (FIG. 1B). The similar result was obtained in several other cell lines tested including Cos-7, 293, and TA3 mammary carcinoma cells (data not shown). Our results showed that the cell-associated Ang-3 exists in monomeric, dimeric, and oligomeric forms (FIG. 1B-c, and FIG. 2).

Figure 2A:
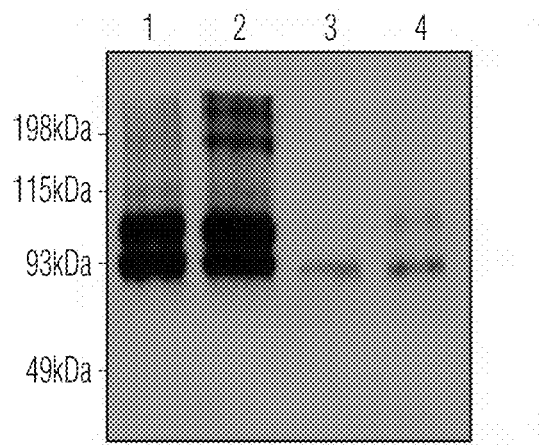
FIG. 2. Ang-3 binds to the surface of various cells. A. Tethering of Ang-3v5 protein to LLC cells is sensitive to trypsin. Two independent clonal LLCAng-3 transfectants were treated and lifted with trypsin (lanes 3-4) or EDTA solution (lanes 1-2), and the cells were washed, lysed, and analyzed by Western blotting with anti-v5 mAb. B. Ang-3v5 protein is present in the cell membrane fraction. LLCAng3 cells were fractionated into crude cell membrane (lanes 1-2) and soluble cytosolic fractions (lanes 3-4). 30 μg of proteins from each fraction were analyzed by Western blotting with anti-v5 mAb. C. A cell based binding assay was performed by incubating purified Ang-3v5 (2 μg, lanes 1-4) or Ang-1v5 (2 μg, lanes 5-8) proteins with $1\times10^6$ of $C_2C_{12}$ (lanes 1 and 5), A10, (lanes 2 and 6), Cos-7 (lanes 3 and 7), and LLC (lanes 4 and 8) cells at 4° C. for 2 hours. After washing with PBS, the cells were lysed and the cell-bound v5-tagged angiopoietins were detected by Western blotting with anti-v5 mAb.
Figure 2B:
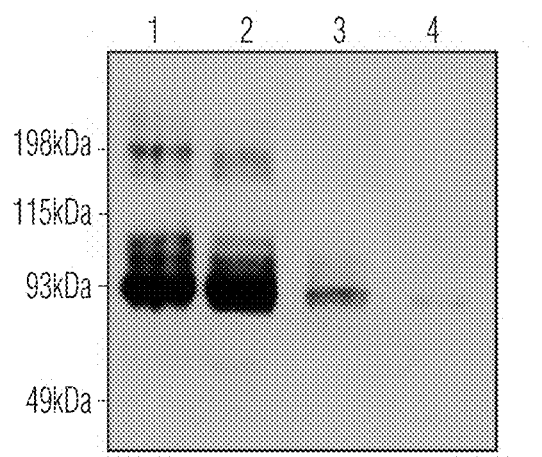

To determine whether endogenous Ang-3 behaves in the same way, we performed Western blot analysis of the proteins derived from C2C12 myoblasts and A10 aortic smooth muscle cells, both of which express endogenous Ang-3 (FIG. 1A). The result showed that Ang-3 expressed by these cells is associated with the cells (data not shown). To further determine whether the association of Ang-3 with LLCAng-3 cells reflects the presence of Ang-3 in intracellular secretory pathway or the binding of Ang-3 to the cell surface, we performed the following experiments. First, LLCAng-3 cells were treated with trypsin or EDTA solution for 10 min at room temperature (RT), washed, lysed, and analyzed by Western blotting with anti-v5 mAb. The result showed that the treatment with trypsin, but not EDTA, dislodges Ang-3v5 from the cells, suggesting that Ang-3v5 is localized on the cell surface where it is accessible to trypsin (FIG. 2A). To confirm this result, we performed Western blot analysis of the proteins derived the cell membrane and soluble cytosolic fractions of LLCAng-3 cells, and found that Ang-3v5 presents in the cell membrane fraction (FIG. 2B, lanes 1-2).

Figure 2C:
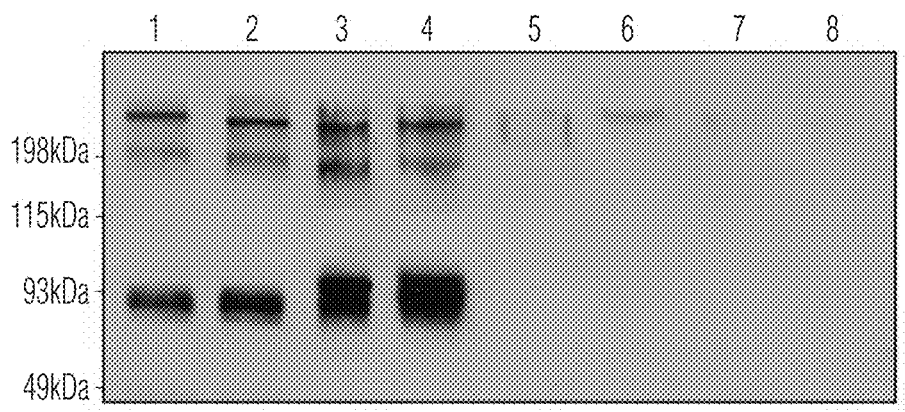

Finally, a cell based binding assay was performed by incubating the EDTA-lifted C2C12, A10, Cos-7, and LLC cells ($1 \times 10^6$) with purified Ang-3v5 or Ang-1v5 (2 µg) at 4° C. for 2 hours. The cells were washed with cold PBS, lysed, and analyzed by Western blotting with anti-v5 mAb. The result showed that Ang-3v5 but not Ang-1v5 binds to all the cells tested (FIG. 2C).

The Cell-Surface Bound Ang-3 is Capable of Binding to Tie-2-Fc Proteins

Figure 3A:
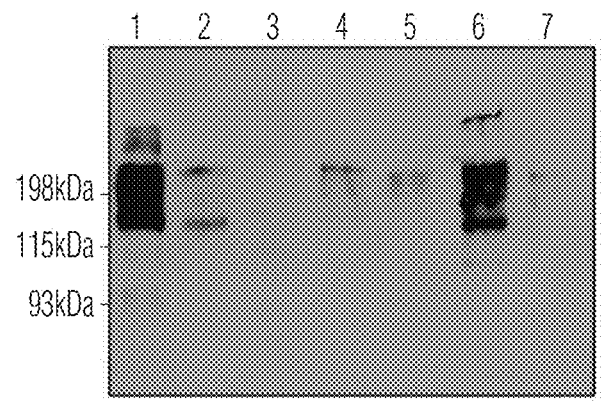
FIG. 3. The cell-surface bound Ang-3 is capable of binding to Tie-2-Fc. A. A cell-based binding assay was performed by incubating 2 μg of Tie-2-Fc (lanes 2, 4, and 6) or CD8-Fc (lanes 3, 5, and 7) with $1\times10^6$ of EDTA-lifted LLCAng-1 (lanes 2-3), LLCAng-2 (lanes 4-5), or LLCAng-3 (lanes 6-7) cells at 4° C. for 2 hours. The cell bound Tie-2-Fc was visualized by Western blotting with anti-human IgG antibody. 100 ng of Tie-2-Fc fusion proteins was loaded in lane 1. B. Tie-2-Fc binds to the cell-surface bound Ang-3. 2 μg/ml of Tie-2-Fc (B-b) or CD8-Fc (B-c) was applied to the methanol fixed LLCAng-3 cells with (B-d) or without (B-b) pre-incubation of the Fc fusion proteins with 204 ml soluble Ang-3. The cell surface bound Tie-2-Fc was revealed by FITC-conjugated anti-human Fc antibody. The distribution of Ang-3v5 was revealed by anti-v5 mAb (B-a). Bar: 30 μm.

To determine whether the cell surface-bound Ang-3 is capable of binding to Tie-2-Fc fusion protein, $1 \times 10^6$ of the EDTA-lifted LLC transfectants (LLCAng-1, -2, and -3) were incubated with 2 µg of Tie-2-Fc or CD8-Fc (as a negative control) at 4° C. for 2 hours. After washing, the cells were lysed and Western blotting was performed using anti-human IgG antibody to detect cell surface bound Tie-2-Fc or CD8-Fc. The result showed that Tie-2-Fc but not CD8-Fc binds to LLCAng-3 cells but not to LLCAng-1 and LLCAng-2 cells (FIG. 3A).

Figure 3B:
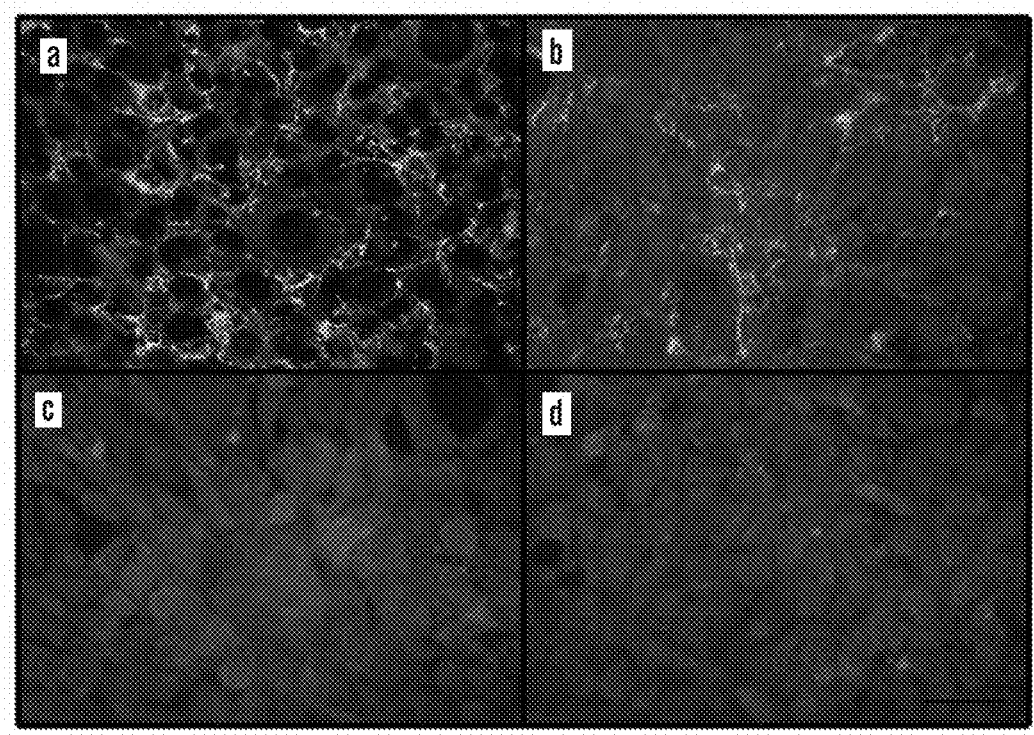

To confirm this result, 2 µg/ml of Tie-2-Fc or CD8-Fc was applied to the fixed LLCAng-3 cells with or without pre-incubation with 20 µg/ml soluble Ang-3. The cell surface bound Tie-2-Fc was revealed by FITC-conjugated anti-human Fc antibody. The result showed that Tie-2-Fc but not CD8-Fc binds to LLCAng-3 cells in a similar fashion to Ang-3, and the binding can be blocked by the excess amount of soluble Ang-3 (FIG. 3B). Together, these results suggest that tethering Ang-3 on the cell surface likely provides a mechanism to localize, concentrate, and present Ang-3 to its receptor rather than to sequester Ang-3, and that the domains of Ang-3 that bind to Tie-2 and its putative cell surface binding partner(s) are different.

The Coiled-Coil Domain of Ang-3 Mediates the Cell Surface Binding of Ang-3.

To determine which domain of Ang-3 mediating the binding of Ang-3 to cell surface, we made several deletion constructs of Ang-3, which contain the coiled-coil (C-C) domain plus the linker peptide region, the C-C domain, or the linker peptide region plus the FHD (FIG. 4A). The cDNA sequence encoding the signal peptide (SP) of Ang-3 was constructed to the N-terminal of all the deletion fragments, so that they can be expressed and secreted properly (Xu and Yu, 2001). In addition, v5-epitope was tagged on the C-termini of these fragments for easy identification. These expression constructs were used to transfect Cos-7 cells in triplicate. 72 hours after the transfection, one set of the transfected Cos-7 cells were treated with trypsin for 10 min at RT, which was known to release the cell-surface bound Ang-3 (FIG. 2A). Equal amount of proteins derived from culture supernatants (FIG. 4B-a) or cell lysates (FIG. 4B-b and c) of the transfected Cos-7 cells, which were treated with (B-c) or without (B-b) trypsin, were analyzed by Western blotting with anti-v5 mAb. The results showed that like full-length Ang-3, the coiled-coiled fragments of Ang-3 bind to the cells and the binding is sensitive to trypsin. On the contrary, the FHD fragments of Ang-3 are either secreted or reside inside of the transfected cells, and is insensitive to the treatment of trypsin (FIG. 4B-b, c, lane 4). Furthermore, our immunocytochemistry results showed that the coiled-coil fragments of Ang-3 displayed a similar cell surface distribution pattern to that of full-length Ang-3, while the FHD fragments are indeed localized in the intracellular compartments (data not shown). Thus, we conclude that the coiled-coil region of Ang-3 is responsible for the cell surface binding of Ang-3.

The Cell Surface Heparan Sulfate Proteoglycans (HSPGs) Bind to Ang-3.

Our RT-PCR results indicated that the cells displayed binding affinity to Ang-3 (FIG. 2C) do not express Tie-2 (data not shown), suggesting that Ang-3 binds to cell surface via protein(s) other than Tie-2. To determine which cell surface protein(s) bind(s) to Ang-3, we first investigated localization of Ang-3 in LLCAng-3 cells by immunocytochemistry. We found that the localization of Ang-3 resembles that of heparan sulfate (HS) glycosaminoglycans (GAGs) observed previously (not shown). To determine whether Ang-3 is tethered on cell surface via HS, we performed the solid phase binding assay to assess binding affinity of purified Ang-3v5 to heparin, an analog of HS; chondroitin sulfate (CS) and hyaluronan (HA), both of which are negative charged GAGs and used as controls of heparin. The result showed that Ang-3v5 not Ang-1v5 binds to heparin but not to CS and HA (FIG. 5A), suggesting that Ang-3 likely binds to the cell surface via cell surface HSPGs.

Figure 5A:
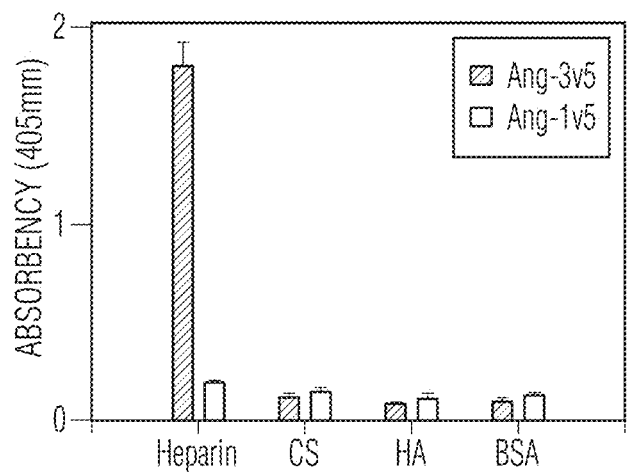
FIG. 5. Ang-3 binds to cell surface HSPGs. A. Ang-3 specifically binds to heparin in a solid phase binding assay. Heparin, chondroitin sulfate (CS), hyaluronan (HA), and BSA (1 mg/ml) were coated onto 96-well Elisa plates in triplicate. Ang-3v5 or Ang-1v5 (500 ng/ml) was incubated with the plates at 4° for overnight. After washing, the Elisa plate-bound Ang-3v5 or Ang-1v5 was detected and measured. B. Binding of Ang-3 to a heparin affinity column. 20 μg of Ang-3v5 was applied into a heparin column. The flow through (FT) was collected (B, lane 2), and the column was washed with non-continuous gradient of NaCl from 0.15N (lanes 3-5), 0.3N (lanes 6-8), 0.6N (lane 9-11), to 1.2N (lanes 12-14), and collected for Western blot analysis using anti-v5 mAb. 100 ng of Ang-3v5 was loaded into lane 1. C. Binding of Ang-3 to the cell surface is sensitive to heparinase treatment. $1\times10^6$ of LLCAng-3 cells were incubated with 50 mM Tris-HCl buffer alone (150 mM NaCl, 0.1% BSA, and 3.5 mM $CaCl_2$, lane 1), or containing heparinase I (5 units/ml) plus heparinase III (0.5 unit/ml, lane 2), or Str. hyaluronidase (lane 3, 5 units/ml) at 37° C. for 2 hours, washed, and lysed. The remaining cell-bound Ang-3v5 was detected by Western blotting with anti-v5 mAb. D. Ang-3v5 binds to syndecan-Fc fusion proteins. Protein-A beads bound with 500 ng of human IgG (lane 1), syndecan-1-Fc (lane 2), syndecan-2-Fc (lane 3), or syndecan-4-Fc (lane 4) were incubated with 1 µg of Ang-3v5 at 4° for two hours. After washing, the bead bound Ang-3 was eluted and subjected to Western blot analysis using anti-v5 mAb. E. Ang-3 colocalizes with heparan sulfate on the cell surface. Confluent LLCAng-3 (E, a-c, and f), LLCAng-1 (E-d), and LLCAng-2 (E-e) cells were fixed and the localization of Ang-3v5 and HS were detected with anti-v5 mAb and TRITC-conjugated secondary antibody (E-a, red fluorescence) or anti-HS antibody and FITC-conjugated secondary antibody (E-b, green fluorescence), respectively. Panels E-a and -b were merged to show the co-localization of Ang-3v5 and HS in yellow color (E-c). Ang-1v5 (E-d) and Ang-2v5 (E-e) were detected by anti-v5 mAb. In panel E-f, only secondary antibody was used. Bar; 32 µm. F. Ang-3 colocalizes with cell surface perlecan and the HS side chains on perlecan are required for the colocalization. Confluent LLCAng-3 cells cultured in the presence (F-e, f, g, and h) or absence of 100 mM sodium chlorate (F-a, b, c, d) were fixed. The localization of perlecan on these cells was detected with anti-perlecan antibody and FITC-conjugated secondary antibody (F-a, green fluorescence); and Ang-3v5 was detected with anti-v5 mAb and TRITC-conjugated secondary antibody (F-b, red fluorescence). HS produced by these cells was detected by anti-HS antibody and FITC-conjugated secondary antibody (F-d and h), which shows that HS is produced by LLCAng-3 cells (F-d) and the production is effectively blocked by sodium chlorate (F-h), indicating perlecan expressed under this condition does not contain HS side chains. Panels F-a and -b were merged to show the co-localization of Ang-3v5 and perlecan in yellow color when perlecan was made as HSPG (F-c). Panels F-e and -f were merged to show there is no colocalization between Ang-3v5 and perlecan in the absence of HS side chains on perlecan. After lift LLCAng-3 cells by EDTA, the ECM deposited on the cell culture plates were fixed and distribution of Ang-3v5 and perlecan was revealed by anti-v5 mAb (F-j) and anti-perlecan antibody (F-i), respective. Panels F-i and -j were merged to show the co-localization of Ang-3v5 and perlecan in the ECM in yellow color (F-k). In panel F-1, only secondary antibody was used. Bar; 28 µm.
Figure 5B:
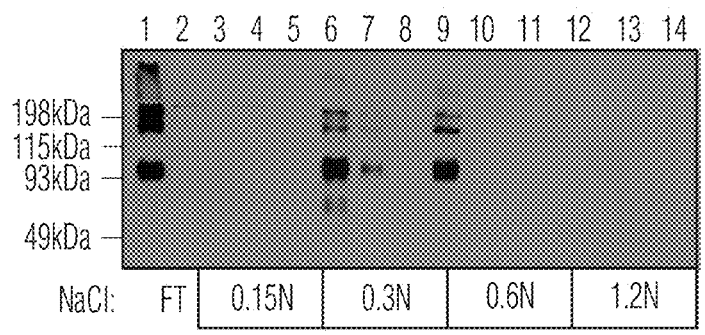
Figure 5C:
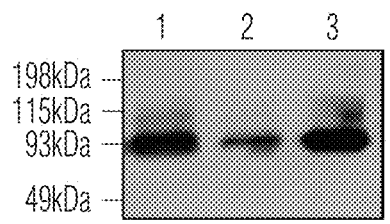
Figure 5D:
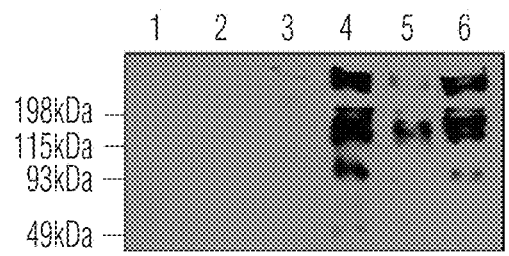
Figure 5E:
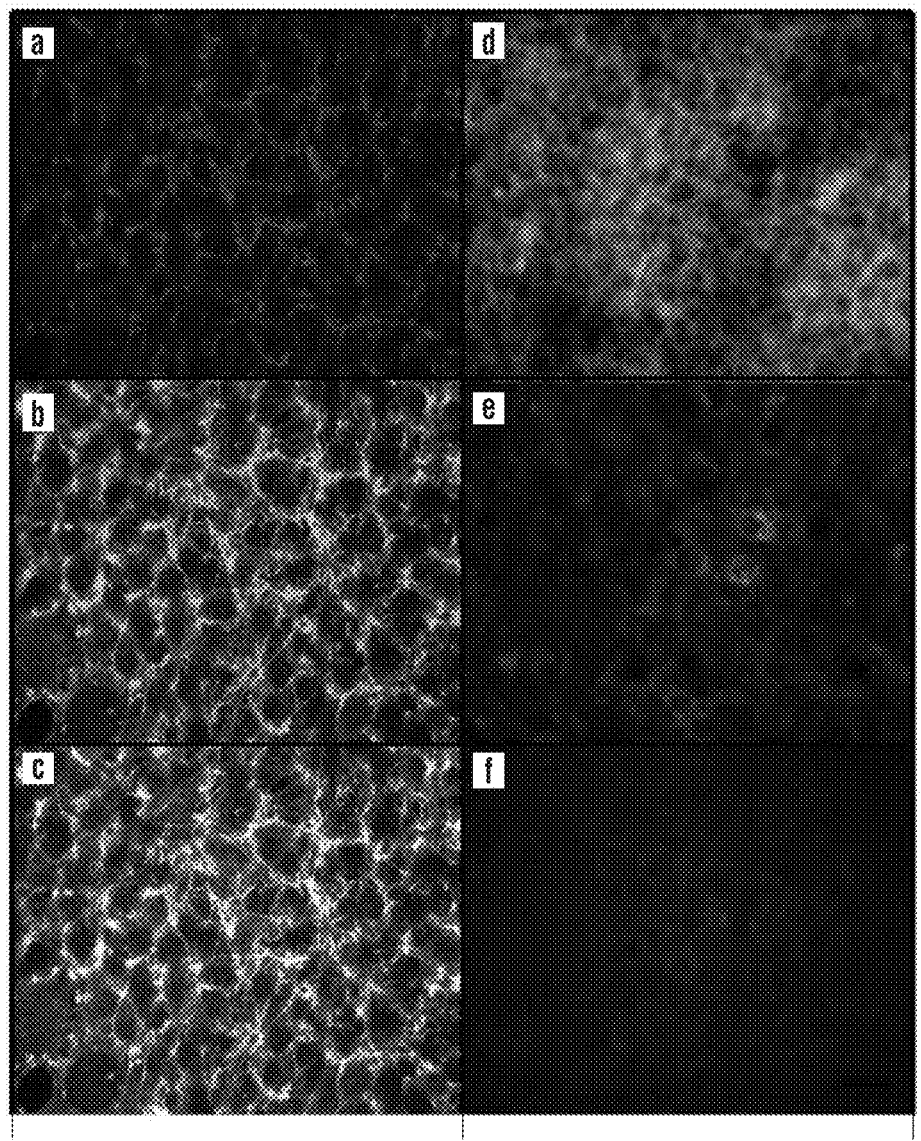

To determine the binding profile of Ang-3 to heparin, we applied purified Ang-3 to a heparin column. Ang-3 was eluted using non-continuous gradient of NaCl (0.15, 0.3, 0.6, and 1.2N). The result showed that Ang-3 proteins were eluted at two different salt concentrations, 0.3N and 0.6N NaCl, implying the presence two subsets of Ang-3 proteins which bind to heparin with different affinities (low and high, FIG. 5B). To confirm that Ang-3 colocalizes with HS on cell surface, we performed immunocolocalization experiment using anti-v5 mAb and TRITC-conjugated secondary antibody to detect Ang-3v5 and anti-heparan sulfate antibody and FITC-conjugated secondary antibody to detect HS, respectively. Our results showed that Ang-3v5 is colocalized with HS on the surface of LLCAng-3 cells (FIG. 5E-a-c).

HS can covalently attach to protein core structures to form HSPGs, which present in the ECM and on cell surface (Sanderson, 2001; Bernfield et al., 1999; Iozzo and San Antonio, 2001). To confirm that cell surface HSPGs bind to Ang-3, the EDTA-lifted LLCAng-3 cells were treated with heparinase or hyaluronidase (as a control) at 37° C. for two hours, washed, lysed, and analyzed by Western blotting with anti-v5 mAb. The result showed that the treatment of LLCAng-3 cells with heparinase but not hyaluronidase releases Ang-3v5 from the cell surface (FIG. 5C); suggesting that cell surface HSPGs tether Ang-3 on the cell surface.

Figure 5F:
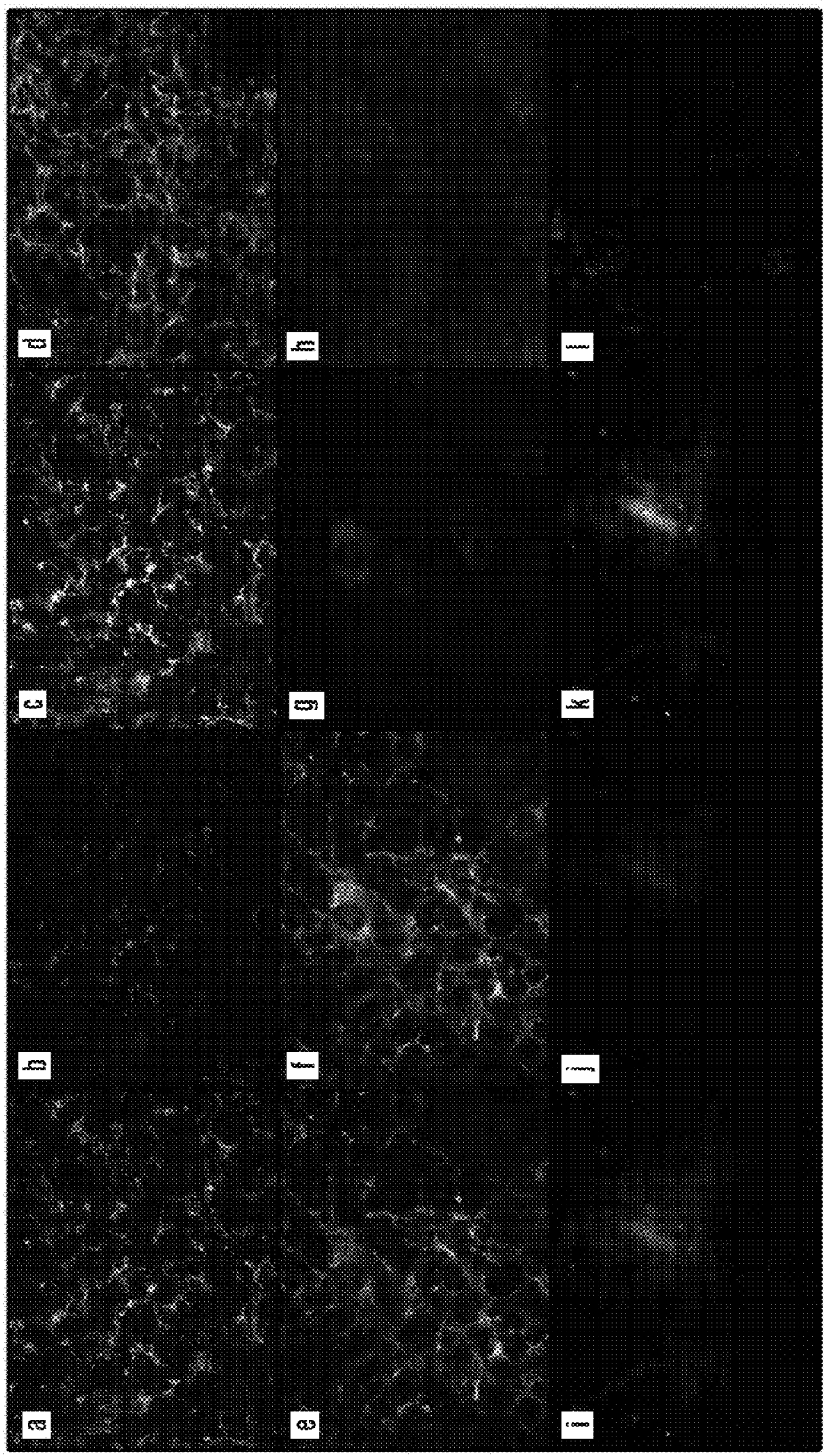

There are three major types of transmembrane HSPGs: syndecans, glypicans and CD44 variants containing v3 exon (CD44v3, Bennett et al., 1995; Jackson et al., 1995). In addition, perlecan is a HSPG that is present in basement membrane and on cell surface (Iozzo, 2001). Perlecan binds to the cell surface through integrin (Battaglia et al., 1993; Chakravarti et al., 1995; Brown et al., 1997), and plays important roles in vascularogenesis, angiogenesis, and tumorigenesis (Iozzo, 2001; Iozzo and San Antonio et al., 2001). Our result showed that the treatment of LLCAng-3 cells with phosphatidyl-inositol-specific phospholipase C (PI-PLC), which releases glycosylphosphotidylinositol (GPI)-anchored proteins including glypicans from cell surface, has no effect on the cell surface binding of Ang-3, suggesting that glypicans are not the primary cell surface HSPGs that bind to Ang-3 in LLC cells (data not shown). RT-PCR result indicated that LLC cells express little CD44v3 (not shown). Thus, CD44 proteins are not likely involved in the binding of Ang-3 in LLC cells. RT-PCR results showed that LLC cells express perlecan and syndecan-1, -2, and -4 (not shown). To investigate whether syndecans bind to Ang-3, Ang-3v5 was immunoprecipitated with the protein-A beads bound with syndecan-1-Fc, syndecan-2-Fc, syndecan-4-Fc proteins, or human IgG (as a control). The results showed that syndecan-1-Fc, to a lesser extent syndecan-4-Fc and syndecan-2-Fc but not human-IgG, bind to Ang-3v5 FIG. 5D), indicating that syndecans binds to Ang-3. Because the distribution pattern of Ang-3 is very similar to that of perlecan, to determine whether perlecan is a major HSPG that tethers Ang-3 onto the cell surface, we performed immunolocalization experiments. Our results showed that Ang-3 is colocalized with perlecan on surface of LLCAng-3, and HS side chains on perlecan are required for the colocalization (FIG. 5F). There are patches of Ang-3 protein deposited into the ECM, which are localized with the ECM deposited perlecan as well (FIG. 5Fi-k). Thus, perlecan is one of the major HSPGs that tether Ang-3 on the surface of LLC cells.

Ang-3 Inhibits Pulmonary Metastasis of LLC and TA3 Cells

Angiogenesis plays an essential role in tumor metastases, and insufficient angiogenesis is thought to be a major reason for maintaining dormancy of micrometastases (Folkman, 1971, 1995; Fidler and Ellis, 1994; Hanahan and Folkman, 1996). It has been established that blocking Tie-2 pathway inhibits tumor growth and metastasis by blocking tumor angiogenesis (Lin et al., 1997, 1998). However, the role of Ang-3 in tumor angiogenesis and metastasis is unknown. To determine that, we established a spontaneous pulmonary metastasis model using a subline of LLC cell that develops pulmonary metastasis after removal of the subcutaneous (s.c.) solid tumor. Using this subline, we have established LLC transfectants expressing Ang-3 (LLCAng-3, FIG. 1B) or transfected with the empty expression vectors alone (LLCwt). Five independent clonal transfectants for each type of transfection were used in the spontaneous pulmonary metastasis experiments. These clonal transfectants displayed no significant difference in morphology and proliferation rate in cell culture condition (not shown).

Figures 6A, 6B, 6C:
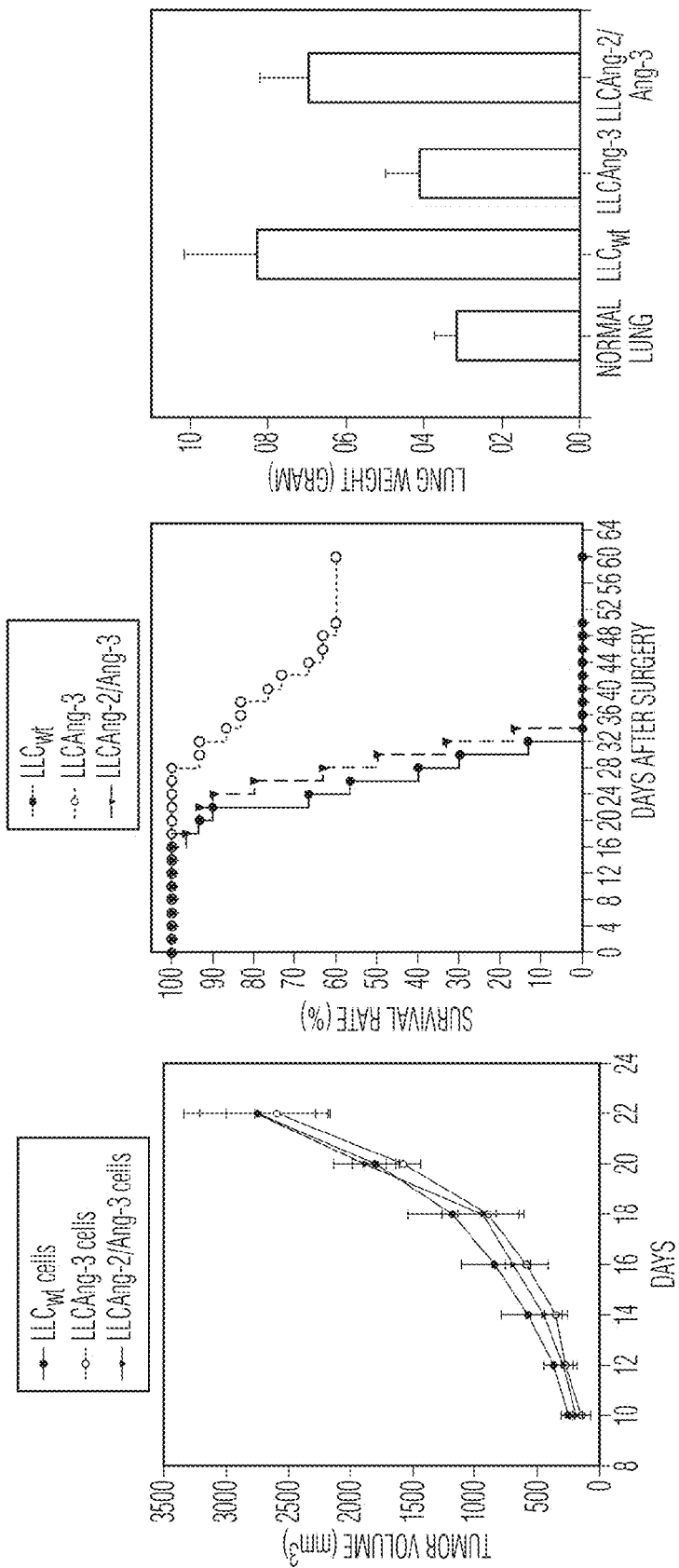
FIG. 6. Ang-3 retards subcutaneous growth of LLC cells and inhibits spontaneous pulmonary metastasis of the cells. The subcutaneous growth and spontaneous pulmonary metastasis assays were performed using LLC transfectants expressing Ang-3 (LLCAng-3) or Ang-2/Ang-3 hybrid (LLCAng-2/Ang-3), or transfected with the empty expression vector alone (LLC$_{wt}$). A. Growth of the s.c. tumors derived from LLCAng-3, LLCAng-2/Ang-3, or LLC$_{wt}$ cells. The means of tumors volumes +/−SD are shown. B. Survival rate of the experimental mice after surgical removal of the s.c. tumors. Total of thirty mice were used for each type transfectant. C. Extent of pulmonary metastasis is expressed by weight of the lungs derived from the experimental mice three weeks after removal the s.c. tumors. D. Histologic and immunologic analysis of the lung sections. Immediately after removal of the s.c. tumors, the CD44-positive micrometastases derived from LLC$_{wt}$ (D-b) and LLCAng-3 (D-c) cells are localized around the preexisted pulmonary vessels (arrows). D-a: evenly distributed CD44-positive macrophages in lung parenchyma. H&E staining of normal lung section (D-d) and the sections derived from the experimental mice three weeks after removal of the s.c tumors derived from LLC$_{wt}$ (D-e) or LLCAng-3 (D-f) cells are shown. Bar: 200 µm. E. Overexpression of Ang-3 blocks tumor angiogenesis. The lung sections derived from normal mouse (E, a-c), or from the experimental mice three weeks after removal of the s.c. tumors derived from LLC$_{wt}$ (E, d-f) or LLCAng-3 (E, g-i) cells. These sections were reacted with anti-vWF antibody to reveal blood vessels (E-a, d, g), with anti-smooth muscle actin antibody to show smooth muscle cells around blood vessels and bronchi (E-b, e, h), and with Apoptag to detect apoptotic cells in situ (E, c, f, i). Bar: 200 µm.

Expression of Ang-3 retarded subcutaneous growth of LLCAng-3 cells comparing to that of LLCwt cells; however, approximate three weeks after implantation of the tumor cells, the solid tumors derived from LLCAng-3 cells reached the size similar to that of the tumors derived from LLCwt cells (FIG. 6A).

Figure 6D:
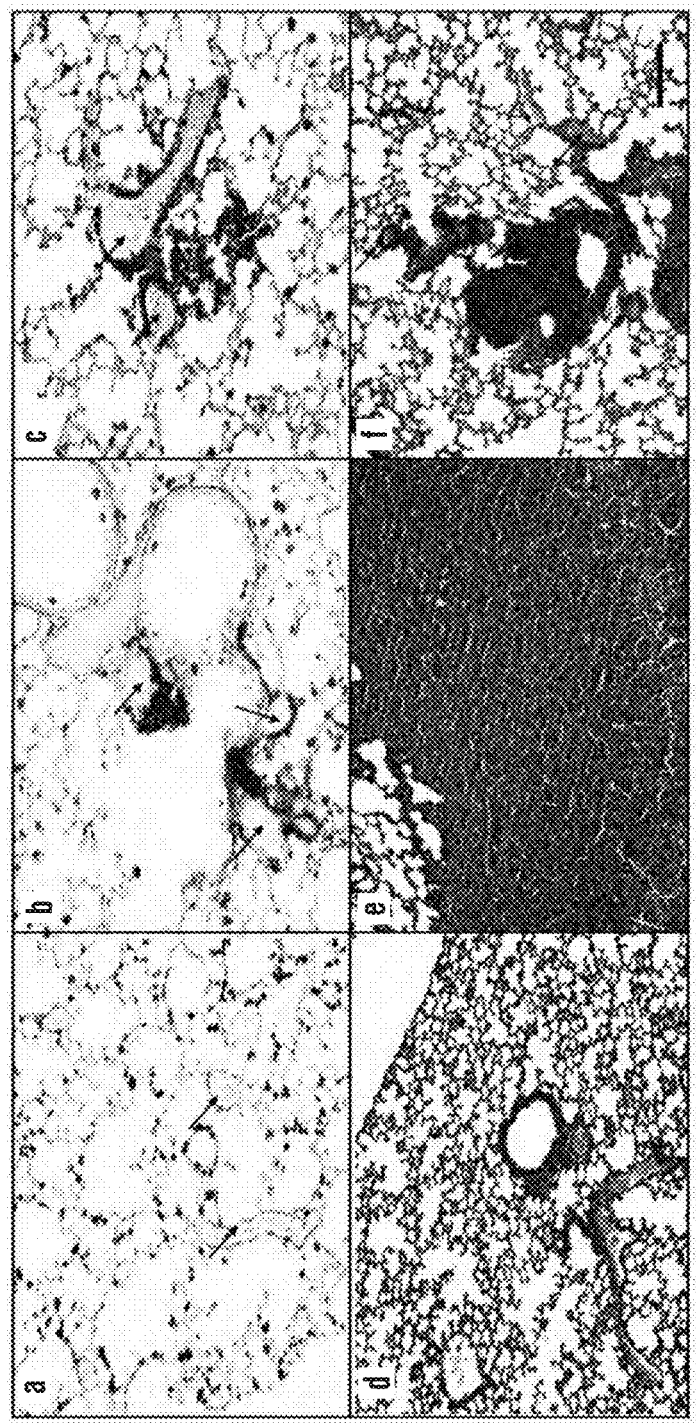
Figure 6E:
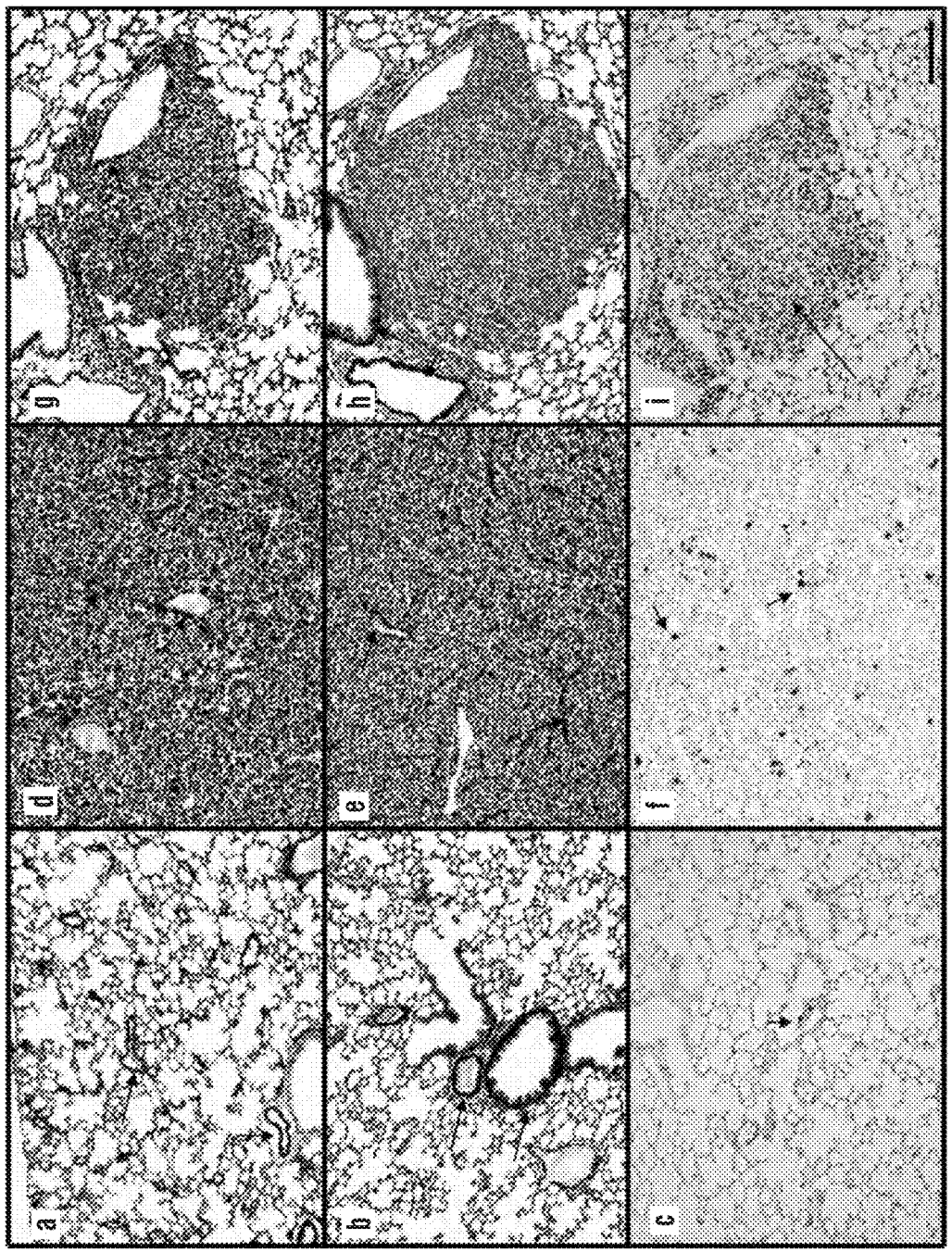

Our results showed that expression of Ang-3 inhibited spontaneous pulmonary metastasis of LLCAng-3 cells and significantly extended the survival time of the mice implanted with LLCAng-3 cells compared to that of the mice received LLCwt cells (FIG. 6B-C). The pulmonary metastatic burden was expressed by average weight of the lungs derived from the experimental mice (FIG. 6C), and average number and size of macro- and micro-metastatic lesions per lung (Table 1). Our results demonstrated that comparing to average weight of health lung, metastatic tumor burden caused by LLCwt cells increased more than 160% of lung weight; while there is only approximate 29% increase in lung weight of the mice received LLCAng-3 cells. In addition, three weeks after removal of the s.c. tumors derived from LLCwt cells, there are about 30 visible metastatic lesions per lung with average diameter of 4.44 mm (Table 1). Hemotoxylin & eosin (H&E) staining of the lung sections indicated that these metastatic tumors are fused together and occupied most of the lung parenchyma (FIG. 6D-e). On the contrary, there are only 3.3 visible metastatic nodules per lung with average diameter of 1.927 mm in the mice received LLCAng-3 cells; however, 125.6 micrometastatic lesions (0.288 mm in diameter) per lung were detected in these lung sections (Table 1). These results suggest that expression of Ang-3 inhibits transformation of pulmonary micrometastasis to macrometastasis.

H&E staining of these lung sections indicated that at the early stage of pulmonary metastasis—immediately after removal of the s.c. tumors, many of the micrometastasis are attached to the preexisted pulmonary blood vessels (not shown). Because LLC cells express high level of CD44 (Xu and Yu, 2003), anti-CD44 antibody was used to highlight these micrometastasis (FIGS. 6D-b and D-c). CD44 is a principal cell surface receptor for hyaluronan. In health mouse lung, evenly distributed macrophages are the major CD44-positive cells (Underhill, 1993; FIG. 6D-a). Our result showed that the CD44-positive micrometastases derived from LLCAng-3 (FIG. 6D-c) and LLCwt (FIG. 6D-b) cells frequently aggregate around the preexisted pulmonary blood vessels (arrows in FIG. 6D-b, c); and that the pulmonary micrometastases derived from LLCwt cells were able to progress to form large metastatic lesions three weeks after removal of the s.c. tumors (FIG. 6D-e). On the contrary, overexpression of Ang-3 inhibited progression of the micrometastases derived from LLCAng-3 cells, which are still small and attached to pulmonary blood vessels (FIG. 6D-f, arrows), implying that adequate angiogenesis was not established in these lesions.

Figure 7A:
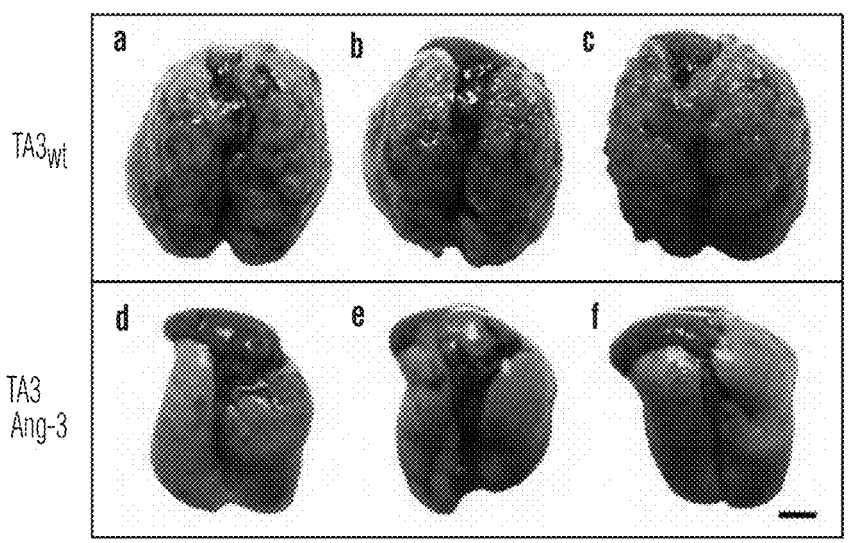
FIG. 7. Ang-3 inhibits pulmonary metastasis of TA3 cells by inhibiting tumor angiogenesis. Five independent clonal TA3$_{wt}$ and TA3Ang-3 cells were used in pulmonary metastasis experiments. Six A/Jax mice were used to inject each transfectant intravenously (i.v.). A. Representative gross pictures of the mouse lungs three weeks after i.v. injection of TA3$_{wt}$ (A, a-c) or TA3Ang-3 (A, d-f) cells. Bar: 3 mm. B. Survival rate of the experimental mice. Total of thirty mice were used for each type of transfectants. C. Pulmonary metastatic burden is expressed by weight of the lungs derived from experimental mice three weeks after the i.v. injection. D. Histologic and immunologic analysis of the lung sections. Panels D-a to f are the representative lung sections that were stained with H&E (D, a-b), anti-vWF antibody (D, c-d), or Apoptag (D, e-f). These sections were derived from the mice received TA3$_{wt}$ cells (D-a, c, e) or TA3Ang-3 cells (D-b, d, f). Bar in a-d: 200 µm and in e-f: 50 µm. The quantitative data of the effect of Ang-3 on tumor angiogenesis and tumor cell apoptosis in vivo are shown in panels E and F, respectively.
Figure 7B:
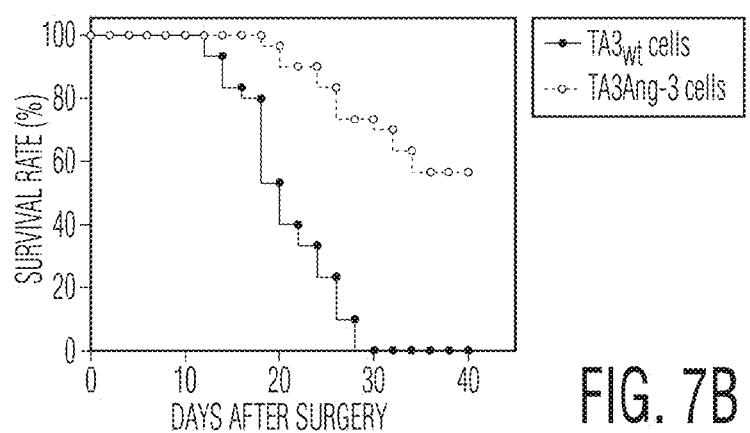
Figure 7C:
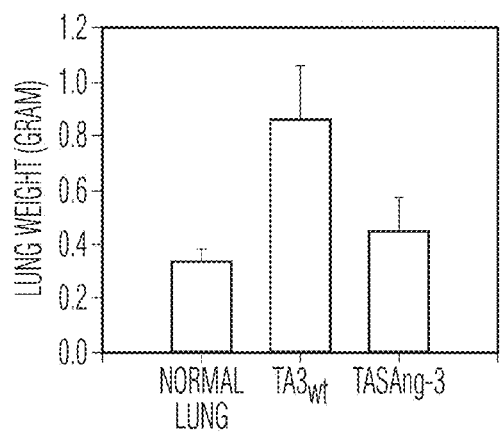
Figure 7D:
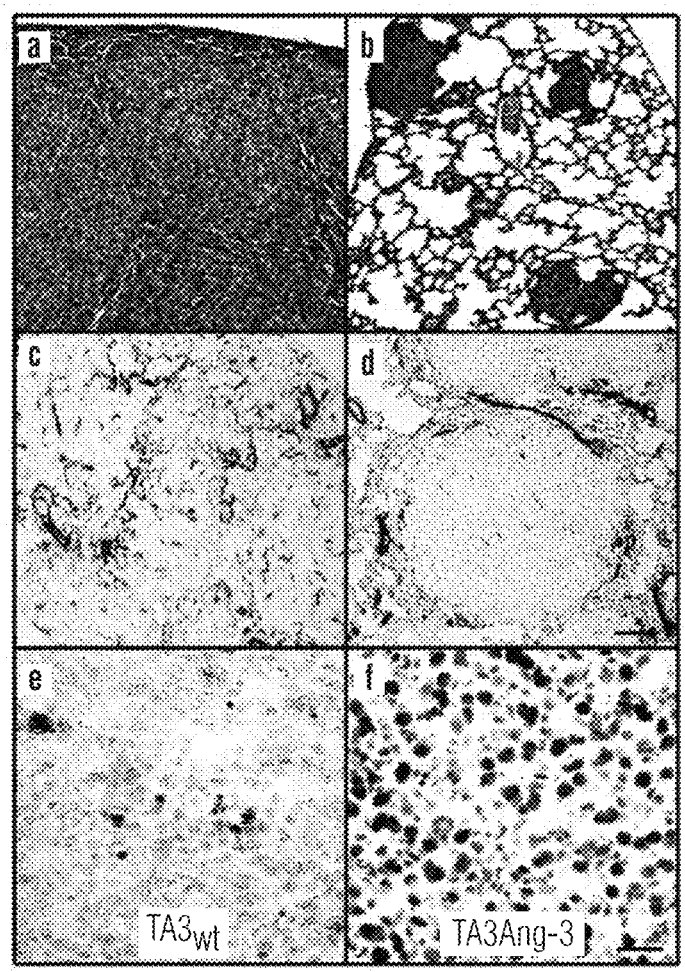
Figure 7E:
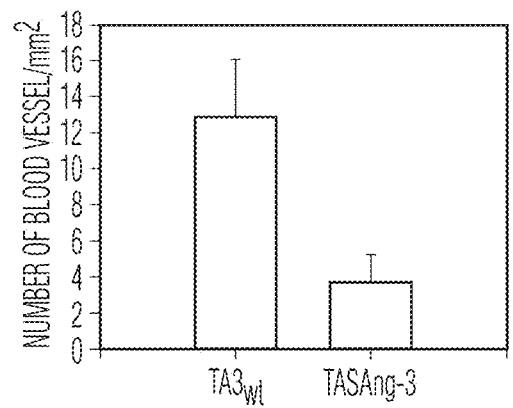
Figure 7F:
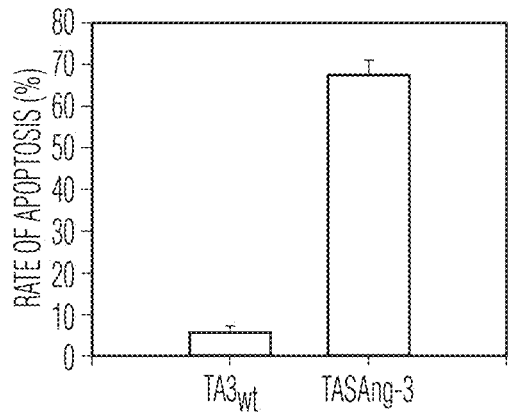

To confirm that the inhibitory effect of Ang-3 on tumor metastasis is not limited to LLC cells, we investigated the effect of Ang-3 on pulmonary metastasis of TA3 mammary carcinoma (TA3) cells. A clonal TA3 cell line that undergoes aggressive pulmonary metastasis after intravenous (i.v.) injection of the cells (Yu and Stamenkovic, 2001) was used to be transfected with the expression constructs. Five independent clonal TA3 transfectants transfected with the empty expression vector (TA3 wt) or expressing Ang-3 (TA3Ang-3) were identified and used in the metastasis experiments. Our result showed that massive pulmonary metastases were formed three weeks after the i.v. injection of TA3 wt cells and expression of Ang-3 inhibits pulmonary metastasis of TA3Ang-3 cells (FIG. 7 A-D). As shown in the representative gross pictures and H&E stained sections (FIG. 7A, D), many metastatic tumors derived from TA3 wt cells are invasive and fused together, which make it difficult to determine accurate number of the metastatic lesions. Thus, metastatic burden was quantified by average weight of the mouse lungs received TA3 wt or TA3Ang-3 cells. Our results demonstrated that expression of Ang-3 in TA3 cells dramatically reduce metastatic burden (FIG. 7C) and significantly extended survival time of the mice (FIG. 7B).

Overexpression of Ang-3 Inhibits Angiogenesis in the Pulmonary Micrometastasis

To investigate whether adequate angiogenesis was not established in the pulmonary micrometastases derived from LLCAng-3 and TA3Ang-3 cells, the lung sections were analyzed for the presence of blood vessels using anti-von Willebrand factor (vWF) antibody which specifically reacts with ECs, and anti-smooth muscle actin (SMA) antibody which highlights smooth muscle cells including peri-vascular smooth muscle cells. Our results showed that there are abundant blood vessels in the pulmonary metastases derived from LLCwt and TA3 wt cells (FIG. 6E-d, arrows, Table 1, FIG. 7D-c) and these blood vessels are surrounded by smooth muscle cells (FIG. 6E-e, arrows, and data not shown). On the contrary, fewer blood vessels were detected in the small pulmonary metastases and micrometastases derived from LLCAng-3 and TA3Ang-3 cells (FIG. 6E-g, h, Table 1, and FIG. 7D-d), and many micrometastases still grow around the preexisted pulmonary vessels (FIG. 6E-g, arrow).

Extent of angiogenesis in the pulmonary metastases was expresses as blood vessel density (BVD). BVD was determined by counting blood vessels in ten randomly selected 100× microscopic fields containing the pulmonary macro- or micro-metastases and expressed as average number of blood vessels/mm$^2$ of the pulmonary tumors. The statistic data indicated that there are approximate four times more blood vessels per mm$^2$ in the metastatic lesions derived from LLCwt or TA3wt cells than that in micrometastatic lesions derived from LLCAng-3 or TA3Ang-3 cells (Table 1, and FIG. 7E). These results suggested that overexpression of Ang-3 inhibits tumor angiogenesis, therefore the progression of micrometastases to full-blown metastatic lesions.

To determine whether inadequate angiogenesis in these micrometastases affects survival of the tumor cells, we performed in situ diction of apoptotic cells on these lung sections. The results showed that less than 10% of the tumor cells are undergoing apoptosis in the metastatic lesions derived from LLCwt or TA3wt cells (FIG. 6E-f, 7D-e, 7F, Table 1), while approximate 67-70% of tumor cells are apoptotic in the micrometastases/small metastases derived from TA3Ang-3 or LLCAng-3 cells (FIG. 6E-i, 7D-f, 7F, Table 1). Together, these results suggest that Ang-3 inhibits pulmonary metastasis of LLC and TA3 cells by inhibiting tumor angiogenesis and promoting apoptosis of the tumor cells.

Binding of Ang-3 to Cell Surface HSPGs is Required for its Effective Inhibition of Pulmonary Metastasis To determine how binding to cell surface HSPGs affects the anti-metastatic activity of Ang-3, we needed to establish an Ang-3 mutant that is incapable of binding to cell surface HSPGs. The HSPG-binding domain of Ang-3 was located in the coiled-coiled region of Ang-3 (FIG. 4), thus we first made eight sequential deletions in this region. Approximate 70 amino acids were deleted in each deletion. These deletional constructs were transiently transfected into Cos-7 cells, and expression and cell-surface binding capacity of the deleted proteins were assessed. Our results showed that all the deletions caused dramatic reduction in expression and secretion of the deleted proteins (data not shown); suggesting that an alternative approach is needed to establish the Ang-3 mutant.

It has been shown previously that bioactivity of Ang-3 is determined by the FHD of Ang-3, and that the hybrid between the coiled-coil region of Ang-2 and the FHD of Ang-3 and wild type Ang-3 evoke a similar response from Tir-2 receptor (Valenzuela et al., 1999). In addition, we have shown that Ang-2 does not bind to cell surface. Based on these data, we generated a hybrid construct between the coiled-coil domain of Ang-2 and the FHD of Ang-3 (Ang-2/Ang-3). Expression and localization of the hybrid protein showed that Ang-2/Ang-3 hybrid is secreted with very limited binding to the cell surface (data not shown). This Ang2/Ang3 expression construct was then used to transfect LLC cells and five independent clonal transfectants expressing Ang-2/Ang-3 hybrid (LLCAng-2/Ang-3) were identified and used in the spontaneous metastasis experiments together with LLCwt and LLCAng-3 cells. The results showed that Ang-2/Ang-3 inhibits pulmonary metastasis much less effectively comparing to that of wild type Ang-3 (FIG. 6B-C); suggesting binding of Ang-3 to cell surface HSPGs enhances its anti-metastasis activity.

The Cell-Surface Bound Ang-3 Induces Retraction and Loss of Integrity of the Endothelial Monolayer.

Figure 8A:
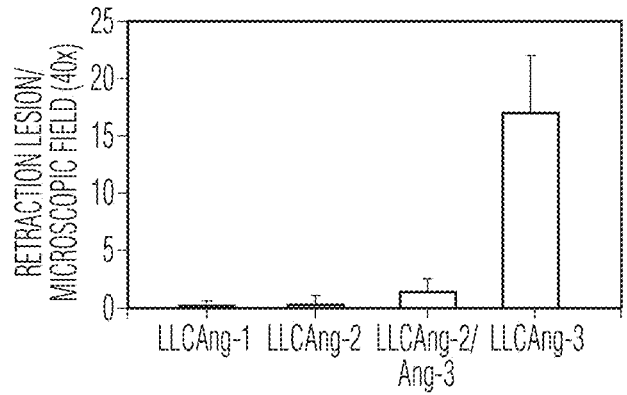
FIG. 8. The cell surface bound Ang-3 induces retraction and loss of integrity of the endothelial monolayers. $5\times10^5$ of green fluorescein labeled LLCAng-3 (B-g, h, i), LLCAng-1 (B-a, b, c), LLCAng-2 (B-d, e, f), or LLCAng-2/Ang-3 (B-j, k, l) cells were seeded to the monolayers of CAPEs for four hours at 37° C. The cells were fixed and observed under light (B-a, d, g, j) and fluorescence microscope (B-b, e, h, k). The images under the same microscopic fields of light or fluorescence were overlaid on top of each other to show the relative locations of the green fluorescein labeled tumor cells and the unlabeled CAPEs (B-c, f, i, l). Bar: 150 µm. The endothelial retraction lesions were counted in ten randomly selected microscopic (40x) fields and the extent of endothelial monolayer retraction per microscopic field is expressed as mean+/−S.D. (A).
Figure 8B:
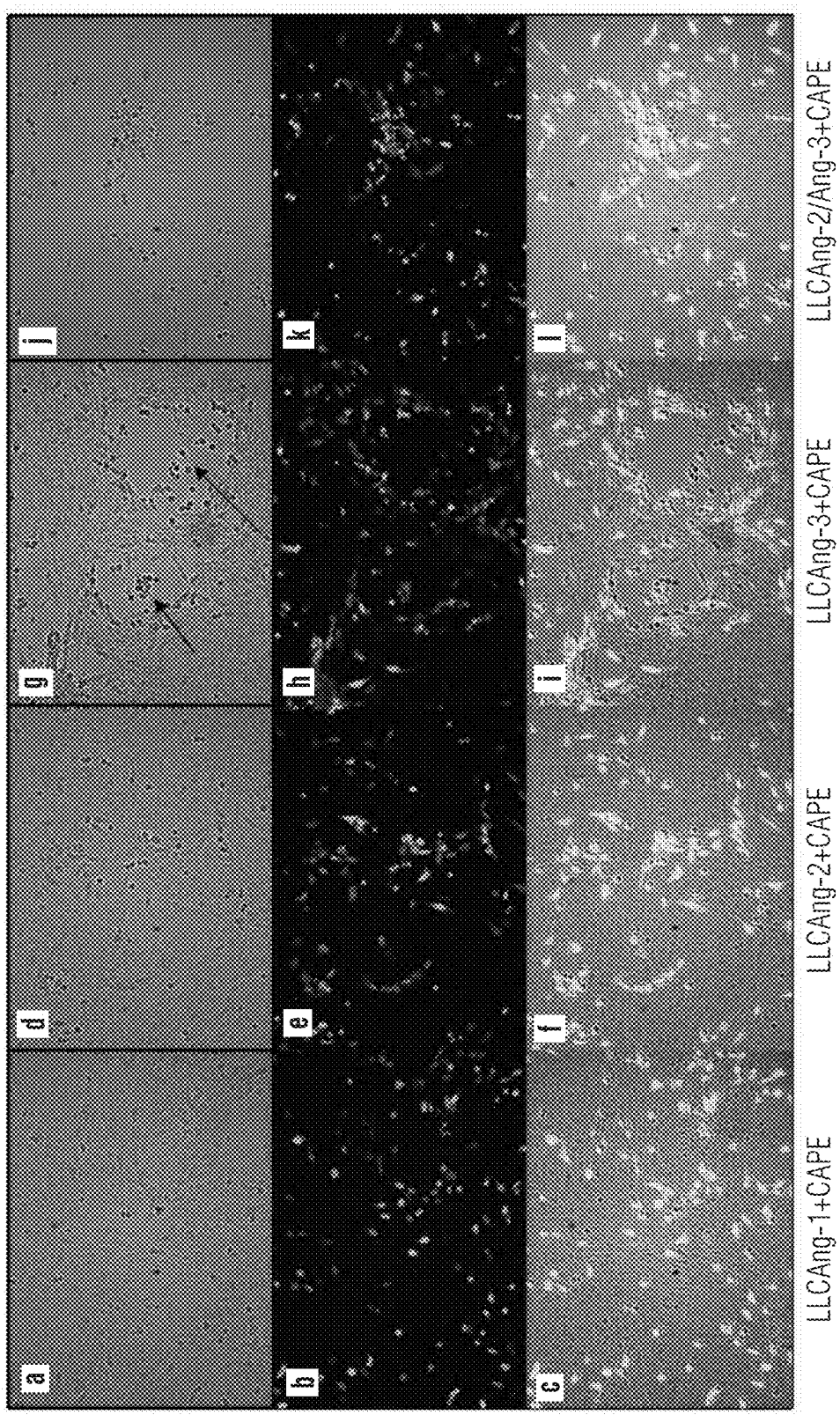

EC sprouting is an important step in angiogenesis and Ang-1 plays an important role in promoting EC sprouting (Koblizek et al., 1998; Hayes et al., 1999). To understand the mechanism by which Ang-3 inhibits tumor angiogenesis and metastasis, we investigated the effect of Ang-3 on integrity of endothelial monolayer by performing the tumor cell-EC co-culture assay. In this assay, green-fluorescein labeled LLCAng-3, LLCAng-2/Ang-3, LLCAng-2, or LLCAng-1 cells were seeded onto the monolayers of CAPEs. Soluble angiopoietins (200 ng/ml) alone were added in to the monolayers as well. The cells were cultured for four hours at 37° C., fixed and observed under microscope. Our result showed that LLCAng-3 cells which retain Ang-3 proteins on the cell surface, but not LLCAng-2/Ang-3 cells or soluble Ang-3 proteins, induce retraction and loss of integrity of the CAPE monolayers (FIG. 8B, data not shown). The extent of EC retraction was determined by counting the endothelial monolayer retraction lesions in ten randomly selected 40× microscopic fields (FIG. 8A). This result implies that cell surface HSPGs facilitate Ang-3 function and Ang-3 inhibits angiogenesis by inducing retraction of ECs which antagonizes the promotive effect of Ang-1 on EC sprouting.

Ang-3 Inhibits EC Proliferation and Survival by Blocking the Activation of Erk and Akt Kinases Induced by Ang-1 and VEGF.

To further elucidate the cellular and molecular mechanism underlying the anti-angiogenic activity of Ang-3, we investigated the effect of Ang-3 on EC proliferation and survival. Our results showed that unlike Ang-1 which has weak effect on EC proliferation (FIGS. 9A and B) and prevents apoptosis of the serum starved ECs (FIG. 9C), Ang-3 inhibits EC proliferation in serum-free and low serum conditions (FIGS. 9A and B) and promotes apoptosis of the serum starved ECs (FIG. 9C).

Figure 9D:
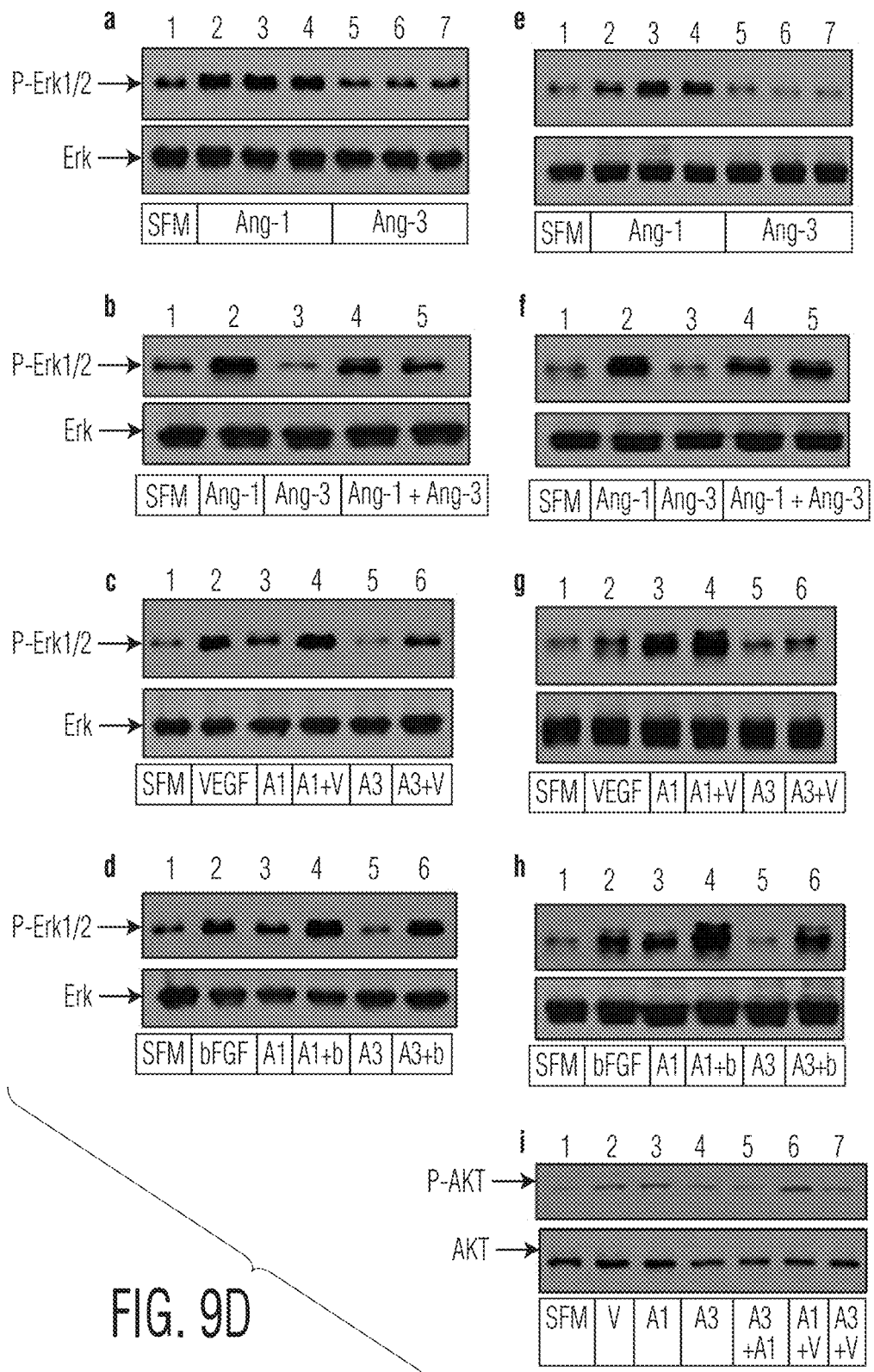
FIG. 9. Ang-3 inhibits EC proliferation and survival and blocks activation of Erk and Akt kinases. A. Serum-starved HUVECs, HMVECs, and UASMCs were switch to serum free medium (SFM, A), 2% FBS medium (B), or SFM/2% FBS medium containing bFGF (15 ng/ml) or 200 ng/ml of angiopoietins and cultured for 48 hours. 10 µl of WST1 reagent was applied into each well and color was allowed to develop for 2 hours and measured at wavelength of 450 nm. B. Apoptosis assay: Brdu-labeled HUVECs were seeded into 24-well plates in triplicate ($5\times10^4$ cells/well) and cultured for 4 hours and switched to SFM for 8 hours. Fresh SFM or SFM containing 15 ng/ml of bFGF or 200 ng/ml of angiopoietins were applied and the cells were cultured for additional 24 hours. The cells (floating and adherent) were collected and apoptotic cells were determined using cellular DNA fragmentation Elisa kit (Roche). D. Ang-3 blocks activation of Erk1/2 and Akt kinases induced by Ang-1 or VEGF$_{165}$. HUVECs were cultured until subconfluence, and switched into SFM and cultured for overnight. Different amount of Ang-1, Ang-3, VEGF, and bFGF in different combinations were applied to the serum-starved HUVECs for 25 minutes (a, b, c, d) or 24 hours (e, f, g, h, i). The cells were lysed and the protein samples were analyzed by Western blotting with anti-phospho-Erk1/2 (upper panels in a-h) or anti-phospho-Akt antibody (upper panel in i) to detect phospho-Erk1/2 (p-Erk1/2) or phospho-Akt (p-Akt), respectively. The membranes were then stripped to apply anti-Erk (bottom panels in a-h) or anti-Akt (bottom panel in i) antibody to detect total Erk or Akt protein, respectively. In panels a and e, 50, 100, 200 ng of Ang-1 (lanes 2-4) or Ang-3 (lanes 5-6) were used. In panels b and f, 100 ng Ang-1 or 200 ng of Ang-3 were used separately (lanes 2-3) or in combination as indicated in the panels (lanes, 4-5). In panels c-i, 15 ng of $VEGF_{165}$ or bFGF, 100 ng of Ang-1 or 200 ng of Ang-3 were used alone or in combination as indicated in the panels. A1 stands for Ang-1; A3 stands for Ang-3; V stands $VEFG_{165}$, and b stands for bFGF.

To determine the molecular mechanism underlying these effects of Ang-3, we investigated how Ang-3 affects two major signal transduction pathways that were known to be activated by Ang-1 (Papapetropoulos et al., 2000; Kim et al., 2000, 2002), the Erk and Akt signaling pathways, which play important roles in cell proliferation and survival. Activation of these two pathways was revealed by the presence of increased amount of phosphorylated Erk1/2 and Akt kinases, respectively. Our results showed that like VEGF165, Ang-1 induces phosphorylation of Erk1/2 in the serum starved HUVECs (FIG. 9D-a, e), and Ang-3 blocks phosphorylation of Erk1/2 induced by Ang-1 or VEGF165 (FIG. 9D-b, c, f, g) but not Erk1/2 phosphorylation induced by bFGF (FIG. 9D-d, h). In addition, Ang-1 induces a sustained Erk1/2 phosphorylation which lasts much longer than that induced by VEGF165 (FIG. 9D-g); and Ang-1 and VEGF165 or Ang-1 and bFGF displayed a synergistic stimulatory effect on Erk1/2 activation (FIG. 9D-c, g, d, h, lane 4). Furthermore, we showed that activation of Akt induced by Ang-1 or VEGF165 is inhibited by Ang-3 as well (FIG. 9D-i, lanes 5, 7). These results suggest that Ang-3 blocks the proliferation and survival signals derived from Ang-1 and/or VEGF165 (FIG. 9D). Together with its effect on EC retraction, these inhibitory effects of Ang-3 likely underlie the inhibitory activity of Ang-3 on tumor angiogenesis and metastasis.

Discussion

Ang-3 Inhibits Pulmonary Tumor Metastasis by Inhibiting Tumor Angiogenesis.

Angiogenesis is essential for tumor growth and metastasis. Different factors produced by tumor cells and surrounding stromal cells play important roles in regulating tumor angiogenesis by activating different pathways that can be overlapped/redundant or independent (Hanahan and Folkman, 1996; Yancopoulos et al., 2000). Studies have shown that blockage of Tie-2 pathway inhibits tumor growth and metastasis (Lin et al., 1997, 1998) and Ang-1 and Ang-2 are involved in tumor angiogenesis (Yu and Stamenkovic, 1999; Ahmad et al., 2001; Etoh et al., 2001; Hawighorst et al., 2002). In our current study, we investigated how Ang-3 affects pulmonary metastasis of LLC and TA3 cells.

Our results showed that Ang-3 retards growth of the s.c. tumors (FIG. 6A), and inhibits pulmonary metastasis by inhibiting angiogenesis and promoting apoptosis of the tumor cells in the micrometastases (FIGS. 6-7, Table 1). Ang-3 displayed much more significant inhibitory effect on pulmonary metastasis than that on s.c. growth of the tumor cells, which is likely caused by different predominant mechanism used by the tumor cells to induce angiogenesis in different microenvironment. During s.c. tumor growth, many tumor cells ($1 \times 10^6$) were implanted into s.c. microenvironment, and initial growth of these tumor cells quickly induce hypoxia in the microenvironment, which up-regulates expression of many factors including VEGF. These factors in turn induce angiogenesis via their corresponding pathways, and angiopoietin-Tie-2 pathway might be expendable in this microenvironment. On the contrary, pulmonary metastasis is a relevant pathologic situation for both lung and mammary carcinomas, which starts with growth of small number of metastatic tumor cells inside of lung parenchyma. Our results showed that pulmonary micrometastases derived from LLC and TA3 cells are often formed around preexisted pulmonary blood vessels which provide necessary nutrition and oxygen to these micrometastases to support their initial growth without evoking hypoxia—vessel cooption (Holash et al., 1999; Yancopoulos et al., 2000; FIG. 6D-b, c, f). In this microenvironment, angiopoietin-Tie-2 pathway likely plays a predominant and essential role, and is required to induce EC sprouting and angiogenesis, and overexpression of Ang-3 disrupts this process.

It is likely that in different physiologic and pathologic conditions and in different micro-environment, the predominant pathway used to induce adequate angiogenesis by different tumor cells is different. Thus, in some instances such as pulmonary metastasis, angiopoietin-Tie-2 pathway is essential; while in others such as s.c. tumor growth, it is replaceable. Our results underscored the importance of identifying the angiogenic pathways that are essential for progression of certain tumors in order to develop effective therapeutic strategies.

Ang-3 and Ang-1 Play Opposite Roles in Regulating EC Behavior and Angiogenesis

It is well established that the interaction between ECs and peri-endothelial cells is important for maintaining vascular integrity and functional blood vessels. It has been shown that Ang-3 blocks Tie-2 receptor phosphorylation induced by Ang-1. Thus, Ang-3 is considered as an antagonist of Tie-2 (Valenzuela et al., 1999). In our current study, we have shown that like Ang-1, Ang-3 is expressed by mesenchymal cells including vascular smooth muscle cells (FIG. 1A), and that Ang-1 and Ang-3 displayed opposite effects on EC proliferation, and survival (FIG. 9). Furthermore, we have demonstrated that the cell surface tethered Ang-3 induces retraction and loss integrity of endothelial monolayer (FIG. 8). On the contrary, studies have shown that Ang-1 plays an important role in maintaining vascular integrity by promoting the interactions between EC and peri-endothelial mural cells (Suri et al., 1996; Thurston et al., 1999, 2000), and Ang-1 enhances the interaction between ECs by regulating localization of PECAM-1 to EC junctions and reducing VE-cadherin and PECAM-1 phosphorylation (Gamble et al., 2000). As an antagonist of Tie-2, it is conceivable that Ang-3 induces EC retraction by weakening the interaction between VE-cadherin and/or PECAM-1.

Loss of endothelial layer integrity is the root of many vascular diseases (Cines et al., 1998; Pober, 1999; Ross, 1993). Our results suggest that Ang-1 and Ang-3 may represent two important factors produced by peri-endothelial cells that play antagonistic roles in maintaining health and integrity of ECs in adult tissues; and the balanced activity of Ang-1 and Ang-3 may be important for initiation of angiogenesis during embryogenesis and tissue repairing and imbalanced up-regulation of Ang-3 activity and/or down-regulation of Ang-1 activity may contribute to vascular diseases such as atherosclerosis and restenosis.

Insufficient formation of neovessels in the micrometastasis derived from LLCAng-3 and TA3Ang-3 cells is likely caused by the ability of Ang-3 to inhibit EC proliferation and survival and to induce retraction of ECs which antagonizes the promotive effect of Ang-1 on EC sprouting. Previous studies have shown that Ang-1 induces activation of Erk1/2 (Kim et al., 2002) and promotes EC survival through PI-3 kinase/Akt pathway (Papapetropoulos et al., 2000; Kim et al., 2000). We have shown that Ang-3 blocks the activation of Erk1/2 and Akt kinases induced by Ang-1 or VEGF (FIG. 9D), which likely underlies anti-angiogenic activity of Ang-3. Additional study is required to determine whether the inhibitory effect of Ang-3 on activation of Erk1/2 and Akt kinases is mediated directly by blocking stimulatory signal derived from Ang-1 or indirectly by modulating activities of other HS-binding angiogenic factors, such as VEGF165.

Ang-3 is Tethered on the Cell Surface Via Cell Surface HSPGs which Enhances its Anti-Angiogenic and Anti-Metastasis Activity Cell surface HSPGs often serve as co-receptors for growth factors and play important roles in modulating their activities (Sanderson et al., 2001; Bernfield et al., 1999; Iozzo and San Antonio, 2001). We have demonstrated that unlike Ang-1 and Ang-2, Ang-3 is tethered on the cell surface via HSPGs (FIG. 1-5), and that soluble Ang-3 proteins tend to form multimers/oligomers, whereas the cell surface bound Ang-3 proteins tend to form monomers, dimers, and some oligomers (FIG. 1-2). Thus, tethering Ang-3 on cell surface concentrates and localizes the proteins in certain aggregated forms which likely provide a specific local signal that may be different from the one derived from soluble Ang-3. Our results showed that at least in LLC cells, syndecans are the primary transmembrane HSPGs that bind to Ang-3 (FIG. 5). Additional studies are required to determine whether Ang-3 binds to different cell surface HSPGs in different cells and whether these HSPGs modulate Ang-3 function differently. Furthermore, the interaction between Ang-3 and cell surface HSPGs implies that Ang-3 may cross-talk with other HSPG-binding growth factors including bFGF and VEGFs, and vice versa.

Studies have shown that cell surface HSPGs can positively or negatively modulate bioactivities of many growth factors by promoting dimerization and oligomerization of growth factors which enhances their affinity to their receptors; or by sequestering the factors from binding to their receptors (Rapraeger et al., 1991; Yayon et al., 1991). Although it is well understood how cell surface HSPGs regulate activity of some growth factors, such as that of bFGF, it remains unclear how cell surface HSPGs regulate activity of other factors including angiogenic activity of VEGF. In current study, we have demonstrated that cell surface HSPGs enhance the anti-angiogenic and anti-metastatasis activity of Ang-3. This is a first clear example that HSPGs enhance anti-metastatasis activity of an anti-angiogenic factor.

Cell surface HSPGs may enhance the anti-metastatic activity of Ang-3 by the following mechanisms. Unlike growth/angiogenic factors, which often have short half-lives and exist in low concentrations, HSPGs are relative stable and abundant (Iozzo and San Antonio, 2001). We found that Ang-3 protein is cleaved (data not shown), and tethering Ang-3 on cell surface HSPGs likely protects Ang-3 from proteolytic cleavage, therefore extends its half-life. In addition, binding to HSPGs can concentrate Ang-3 on tumor cell and EC surface which may be critical for achieving effective blockage of the pro-angiogenic activity of Ang-1 and tumor angiogenesis. Finally, Ang-3 and cell surface HSPGs complexes may generate signals that are different from the ones derived from soluble Ang-3 and cell surface HSPGs alone.

Materials and Methods

Cell Lines and Reagents

LLC, A10, C2C12 myoblast, 3T3 fibroblast, and Cos-7 cells were obtained from the Cell Center Service Facility of University of Pennsylvania. Human umbilical vein endothelial cells (HUVECs), human dermal microvascular endothelial cells (HMVECs), and human umbilical artery smooth muscle cells (UASMCs) were obtained from Cambrex. MS1 endothelial cells and 293 cells were obtained from ATCC and Invitrogen, respectively. Anti-CD44 (ATCC), -v5 epitope (Invitrogen), -Tie2, -Ang-1, -2, and -3 (Santa Cruz), -vWF, -smooth muscle actin (Dako), -phosphorylated tyrosine (BD Transduction Lab), -heparan sulfate (CalBiochem), -Erk1/2, -phospho-Erk1/2 (Santa Cruz), -Akt, and -phospho-Akt (Cell Signal) antibodies, heparinase I and III (Sigma), Str. hyaluronidase (ICN), Tie-2-Fc (R&D), and Apoptag kit (Chemicon) were used in the experiments.

Reverse Transcriptase-Polymerase Chain Reaction (RT-PCR), Mutagenesis, and Expression Constructs Total RNAs were isolated from mouse placenta, LLC, TA3, A10, 3T3, C2C12 and MS1 cells using TRIzol reagent (Invitrogen). RT-PCR was performed as described (Yu et al., 1997) using the primer pairs corresponding to the 5' and 3' extremity of 24 nucleotides of the coding sequence of mouse Ang-3 or β-actin under the accession numbers AF113707 and X03672, respectively.

Full-length Ang-1, -2, and -3 cDNAs were amplified by PCR using mouse placenta cDNAs as templates, together with Pfu DNA polymerase (Stratagene) and the pairs of primers corresponding to the 5' and 3' extremity of 24 nucleotides of the coding sequence of the each molecule (the accession numbers U83509, AF004326, and AF113707). The stop codons were omitted from the reverse primers in order to fuse angiopoietins to the C-terminal v5 epitope tag existed in the expression vector (pEF6/v5-HisTOPO, Invitrogen). The resulting PCR fragments were inserted into pEF6/v5-HisTOPO expression vectors. Authenticity of the inserts was confirmed by DNA sequencing.

The various deletion fragments of Ang-3 were generated as detailed in the FIG. 4 using the full-length Ang-3 as a template and the ExSite PCR-based site-directed mutagenesis kit (Stratagene). The accuracy of the deletions was confirmed by DNA sequencing.

Transient and Stable Transfection

A subline of LLC and TA3 or Cos-7 cells were transfected using Lipofectamine (Invitrogen) and with the expression constructs containing cDNA inserts encoding mouse Ang-1, -2, -3, Ang-2/Ang-3 hybrid, or Ang-4 or with the empty expression vector alone. The transfected LLC and TA3 were selected for their resistance to blasticidin and the expression level of v5-epitope tagged angiopoietins or Ang2/Ang-3 hybrid by clonal LLC and TA3 transfectants was determined by Western blotting with anti-v5 mAb.

Production and Purification of Angiopoietins

Five liters of cell culture supernatants derived from LLC transfectants expressing mouse or human Ang-1, Ang-2, or mouse Ang-3 proteins were collected and purified through Ni+-Probond affinity columns (Invitrogen) and the affinity columns conjugated with anti-v5 antibodies (Sigma). Purity of the purified angiopoietins was determined by silver staining of SDS-10% PAGE gel loaded with the purified proteins under reducing condition. Concentration of the purified proteins was determined by Bio-Rad Bradford protein assay.

Protein Sample Preparation, Western Blot Analysis, and Immunoprecipitation

To determine the distribution patterns of angiopoietins, the cell culture supernatants derived from LLC and TA3 transfectants or the transiently transfected Cos-7 cells were collected, and the cells were either treated with trypsin for 10 min at RT and washed once with 10% FBS DMEM, or released from the culture dishes by phosphate-buffered saline solution (PBS) containing 5 mM EDTA. The trypsin- or EDTA-lifted cells were lysed in 2×SDS sample buffer. The ECM materials remained on the cell culture dishes were washed and extracted with 2×SDS sample buffer. These proteins were subjected to Western blot analysis as described (Xu and Yu, 2001).

To determine the binding between cell surface heparan sulfate (HS) and Ang-3, the EDTA-lifted LLCAng-3 cells were treated with heparinase I (5 units/ml) and heparinase III (0.5 unit/ml) or Str. hyaluronidase (5 unit/ml, as a control) at 37° C. for two hours, washed, lysed with 2×SDS sample buffer and analyzed by Western blotting with anti-v5 mAb.

To determine interaction between Ang-3 and syndecans, syndecan-Fc fusion proteins were produced by transiently transfection of the expression constructs containing syndecan-1-Fc (syn1-Fc), syndecan-2-Fc (syn2-FC), or syndecan-4-Fc (syn-4-Fc) into 293 cells. The serum-free cell culture supernatants derived from these transfected cells were purified through protein-A affinity columns. Protein A bead bound human IgG, syn1-Fc, syn2-Fc, or syn-4-Fc (500 ng) were incubated with Ang-3v5 (1 µg) at 40 for two hours. After washing, the bound proteins were eluted and subjected to Western blot analysis.

Erk and Akt Phosphorylation Assay

HUVECs were cultured until subconfluence, and switched to serum-free medium (SFM) for overnight. Different amount Ang-1, Ang-3, VEGF, and bFGF in different combinations were applied to the serum-starved HUVECs for 25 minutes or 24 hours as detailed in the figure legend (FIG. 9D). The cells were then lysed and equal amount of the proteins were analyzed Western blotting with anti-phospho-Erk1/2 or anti-phospho-Akt antibody to detect phosphor-Erk1/2 and phosphor-Akt proteins, respectively. The membranes were then stripped and applied with anti-Erk or anti-Akt antibody to detect total amount of Erk and Akt proteins, respectively.

Solid Phase and Cell-Based Ligand Binding Assay 96-well Elisa plates were coated overnight at 4° C. with heparin, chondroitin sulfate, or hyaluronan or BSA (1 mg/ml, Sigma) in triplicate. The coated plates were washed and blocked with 0.5% BSA. Purified Ang-1v5 or Ang-3v5 (500 ng/ml) was incubated with the coated plates for overnight at 4° C. After washing with phosphate buffer containing 300 mM NaCl, the bound Ang-1v5 or Ang-3v5 was detected and measured.

The cell-based ligand binding assays were performed by incubating purified Ang-3v5 or Ang-1v5 (2 µg) with the EDTA-lifted 1×10$^6$ of C2C12, A10, Cos-7, and LLC cells; or by incubating Tie-2-Fc (2 µg) or CD-8-Fc (2 µg, as a control) with the EDTA-lifted LLCAng-1, LLCAng-2, or LLCAng-3 cells (Xu and Yu, 2001) at 4° C. for 2 hours. The cells were washed with PBS and lysed in 2×SDS sample buffer. The cell surface bound v5-tagged angiopoietins or Tie-2-Fc was detected by Western blotting with anti-v5 mAb or anti-human IgG, respectively.

Heparin Affinity Column

To determine the binding profile of Ang-3 to heparin, □□g of purified Ang-3v5 proteins were applied into a heparin affinity column (Sigma). The column was eluted using non-continuous gradient of NaCl (0.15, 0.3, 0.6, and 1.2N). Three fractions (2 ml/each) were collected for each NaCl concentration, and 20 µl of the samples from each fraction was analyzed on Western blot with anti-v5 mAb.

Tumor and Endothelial Cell Co-Culture Assay

Subconfluent LLCAng-3, LLCAng-2/Ang-3, LLCAng-2, and LLCAng-1 cells were labeled with CellTracker Green CMFDA fluorescein (Molecular Probes) as described (Yu et al., 1997) and lifted with EDTA solution and washed. The EDTA-lifted cells or soluble angiopoietin (200 ng/ml) were added to the monolayers of bovine pulmonary artery endothelial cells (CAPEs) in triplicate for four hours at 37° C., the cells were fixed and observed under microscope and photographed. The endothelial retraction lesions were counted in ten randomly selected microscopic (40×) fields.

Immuocytochemistry

LLC transfectants expressing Ang-1, Ang-2 or Ang-3, or transfected with the empty expression vector alone were cultured in 35 mm dishes until confluence and fixed. The antibodies against v5 epitope, Ang-1, -2, and -3 were used to detected the corresponding proteins in the fixed cells as described (Xu and Yu, 2001). To investigate the relative localization of Ang-3 and heparan sulfate (HS) on LLCAng-3 cell surface, immunocolocalization experiment was performed using anti-v5 antibody and TRITC-conjugated secondary antibody to detect Ang-3v5 and anti-heparan sulfate antibody and FITC-conjugated secondary antibody to detect HS. To determine the relative localization of Ang-3 and perlecan, and determine whether heparan sulfate (HS) side chains are required for the binding of Ang-3 to the cell surface, LLCAng-3 cells were cultured in the absence or presence of 100 mM of sodium chlorate and fixed. Immunocolocalization experiments were performed using anti-v5 antibody with TRITC-conjugated secondary antibody to detect Ang-3v5 protein, and anti-perlecan (NeoMarkers) antibody with FITC-conjugated secondary antibody to detect perlecan, respectively. The inhibitory effect of sodium chlorate on synthesis of HS in these LLCAng-3 cells was revealed by anti-HS antibody.

To determine whether the cell surface-bound Ang-3 binds to Tie-2-Fc fusion protein, the methanol fixed LLCAng-3 cells were washed, blocked, and incubated with Tie-2-Fc or CD8-Fc (2 μg/ml). The cell-surface bound Tie-2-Fc was revealed by FITC-conjugated anti-human Fc antibody.

Cell Proliferation and Apoptosis Assay

The proliferation assay was performed by seeding HUVECs, HMVECs, and UASMCs at 5×103 cells/well of 96-well plates in triplicate. After one day, the cells were switch to serum free medium (SFM) and cultured for additional 8 hours. Fresh SFM or 2% FBS medium alone, SFM or 2% FBS medium containing bFGF (15 ng/ml) or 200 ng/ml of purified angiopoietins was added to the cells, and the cells were cultured for additional 48 hour. 10 μl of WST1 reagent (Roche) was applied into each well of the 96-well plates and color was allowed to develop for 2 hours and measured at wavelength of 450 nm.

Apoptosis assay was performed by seeding 5-Bromo-2'-deoxy-uridine (Brdu)-labeled HUVECs into 24-well plates in triplicate (5×$10^4$ cells/well) and cultured in EGM-2 complete medium (Cambrex) for four hours, switched to SFM for 8 hours and replaced with fresh SFM alone or SFM containing 15 ng/ml of bFGF or 200 ng/ml of purified angiopoietins, and cultured for additional 24 hours. The floating and adherent cells were collected and extent of apoptosis was determined by the cellular DNA fragmentation Elisa kit (Roche).

Subcutaneous Tumor Growth and Pulmonary Tumor Metastasis

Five independent clonal LLCAng-3 or LLCwt cells were injected subcutaneously into the left flank of C57BL/6 mice (Jackson Laboratory, 1×$10^6$ cells/mouse), and six mice were injected with each clonal transfectant. After solid tumors became visible, which usually occurs between 10-15 days after the injection, and tumor size is approximately 4-5 mm in diameter, the tumors were measured by a digital caliper every other day for the next two weeks. The largest and shortest diameters of the solid tumors were measured. The tumor volume was calculated by using the following formula: tumor volume=½×(shortest diameter)2×longest diameter (mm3, Hamid et al., 2000).

In the spontaneous pulmonary metastasis experiments, these s.c. solid tumors were removed surgically approximate three weeks after the tumor implantation when size of the tumors reaches approximately 1.5-2.0 cm in the longest diameter. Two types of the experiments were performed using these mice. In one set of the experiments, the experimental mice were observed daily after surgery and duration of mouse survival was recorded. The survival rate of these mice was calculated as following: survival rate (%)=(number of mice are still alive/total number of the experimental mice)×100%. The mice that are free of symptom 60 days after the surgery were sacrificed. In the second set of experiments, three weeks after the surgical removal of the s.c. tumors, pulmonary metastatic burden was assessed by counting surface pulmonary tumors under dissection microscope and measuring weight of the mouse lungs. Gross pictures of the mouse lungs were taken and the digital images were analysis by Image-Pro Plus software 4.5.1. (MediaCybernetics). One hundred randomly selected pulmonary metastases were measured to obtain average diameter of the metastases.

To determine number and diameter of the micrometastasis derived from LLCAng-3 cells, ten mouse lungs received LLCAng-3 cells were fixed and sectioned into 15 □m sections. These sections were stained with H&E, and micrometastasis in these sections were counted. Average diameter of these micrometastasis was determined by measuring the diameters of one hundred randomly selected micrometastasis using Image-Pro Plus software.

Experimental pulmonary metastasis was carried out as detailed previously (Yu and Stamenkovic, 2001) using five independent clonal TA3Ang-3 or TA3 wt cells. The survival rate and pulmonary metastatic burden of these experimental mice were determined as described.

Histology and Immunohistochemistry

Lungs of the experimental mice were fixed, sectioned, and stained with H&E as described (Yu and Stamenkovic, 1999). The sections were reacted with anti-von Willebrand factor or anti-smooth muscle actin (Dako) antibody to assess tumor angiogenesis, with anti-CD44 antibody (mAb IM7.8) to highlight the localization of CD44-positive micrometastasis, or with Apoptag to detect apoptotic cells in situ. Total number of cells and number of apoptotic cells in five randomly selected 400× microscopic fields within the pulmonary metastases or micrometastasis were counted using Image-Pro Plus software, and more than 2,000 cells were counted for each type of transfectants. The apoptosis rate was calculated as the following: apoptosis rate=(number of apoptotic cells per microscopic field/total number of cells per microscopic field)×100%.

To determine blood vessel density, ten randomly selected 100× microscopic fields that contain pulmonary macro- or micro-metastases were photographed. The numbers of blood vessels within the pulmonary metastases or micrometastasis were counted and area value of these pulmonary tumors was measured using Image-Pro Plus software. The blood vessel density was expressed as average number of blood vessels per $mm^2$ of pulmonary tumors.

Example 2: Human Ang-4 Binds to HSPGs and Inhibits Pulmonary Metastasis

To demonstrate that human Ang-4 is equivalent to mouse. Ang-3, experiments were performed to demonstrate that Ang-3 and Ang-4 have similar properties in vitro and in vivo.

Figure 10:
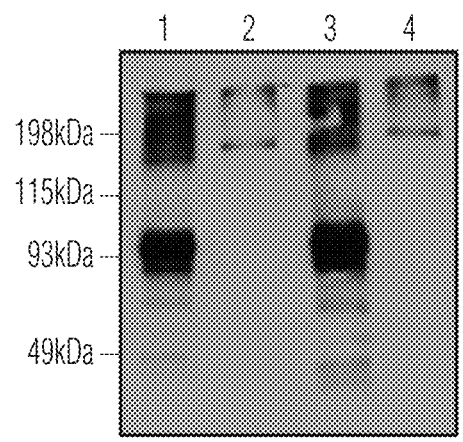
FIG. 10. Human Ang-3/Ang-4 is tethered to the cell surface. Human Ang-3/Ang-4 was transfected into Cos-7 cells. 72 hours after the transfection, proteins derived from the cell culture supernatants (lanes 2 and 4) and cell lysates (lanes 1 and 3) were analyzed by Western blot using anti-v5 mAb to determine the distribution patterns of v5-epitope human Ang-3/Ang-4. KDa stands for kilodalton.

Human Ang-4 was transfected into Cos-7 cells using general transfection (Lipofectamine, Invitrogen) methods as described above. 72 hours after transfection, 40 µg of proteins derived from the cell culture supernatants (FIG. 10, lanes 2 and 4) and cell lysates (FIG. 10, lanes 1 and 3) were analyzed by Western blot using anti-v5 mAb to determine the distribution patterns of v5-epitope human Ang-4. Ang-4 was found to be tethered to the cell surface just like mouse Ang-3.

Figure 11A:
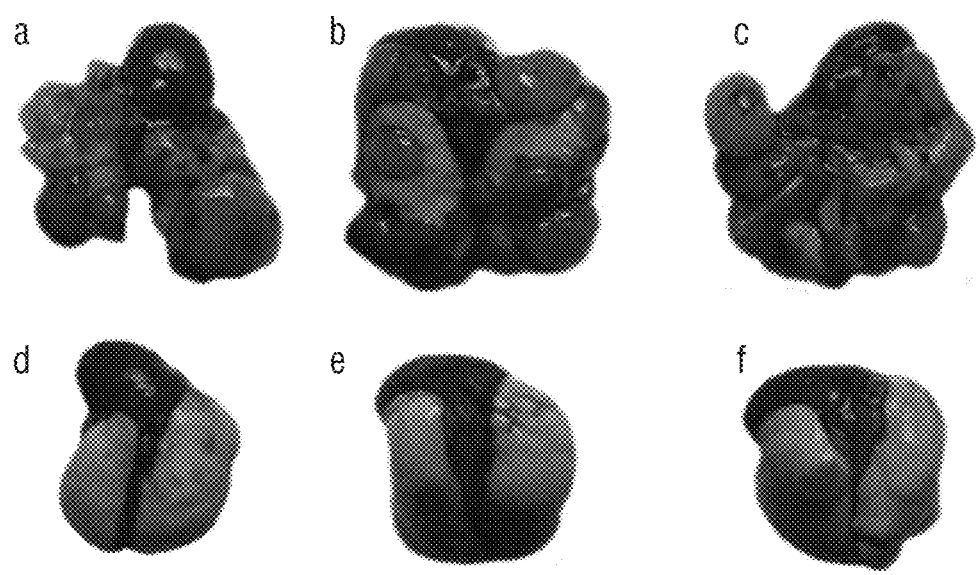
FIG. 11. Human Ang-3/Ang-4 inhibits spontaneous pulmonary metastasis of Lewis lung carcinoma cells. A. Gross pictures of the mouse (C57BL/6) lungs three weeks after removal of subcutaneous tumors derived from $LLC_{wt}$ cells (A, a-c) or LLC transfectants expressing human Ang-3/Ang-4 (LLChumanAng-3/Ang-4, A, d-f). B. Survival rate of the experimental mice after the surgical removal of the s.c. tumors. Total of 15 mice were used for each type of transfectant. C. Extent of pulmonary metastasis is expressed by weight of the lungs derived from experimental mice three weeks after removal the s.c. tumors.
Figure 11B:
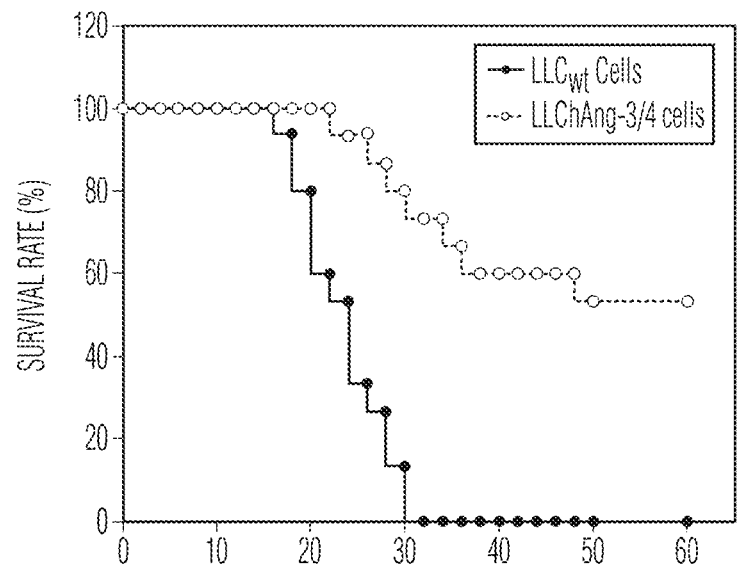
Figure 11C:
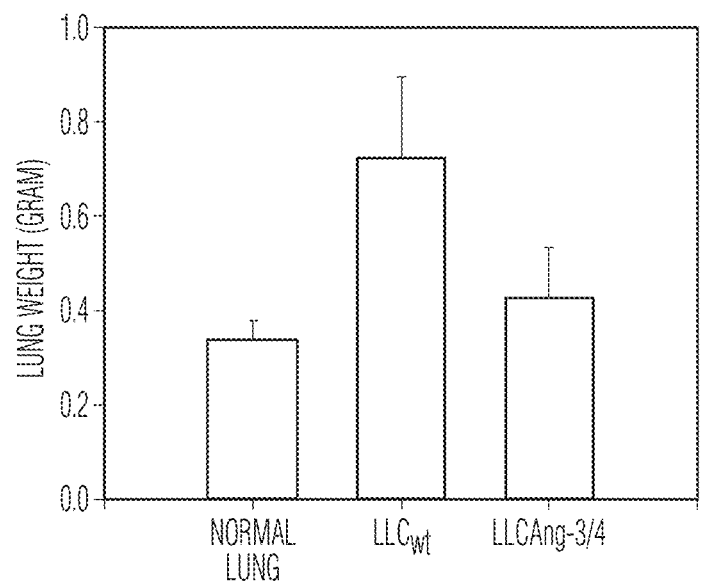

To determine if human Ang-4 inhibits spontaneous pulmonary metastasis of Lewis Lung Carcinoma cells, $1 \times 10^{6-}$ of LLCwt or LLC cells expressing human Ang-4 (LLCAng-3/Ang-4) were implanted subcutaneously. The s.c. tumors were allowed to grow and were removed as described above. The experimental mice were observed daily after surgery and duration of mouse survival was recorded. The survival rate of these mice was calculated as described above. Three weeks after removal of the subcutaneous tumors, the lungs of the experimental mice (C57BL/6) were removed, weighted, and analyzed. Ang-4 was able to inhibit spontaneous pulmonary metastasis of Lewis Lung Carcinoma cells and increase survival of the mice (FIG. 11) just like mouse Ang-3. Therefore, Ang-4 and Ang-3 appear to be homologs of one another not only structurally, but also functionally.

REFERENCES

Ahmad, S. A., Liu, W., Jung, Y. D., Fan, F., Wilson, M., Reinmuth, N., Shaheen, R. M., Bucana, C. D., and Ellis, L. M. 2001. The effects of angiopoietin-1 and -2 on tumor growth and angiogenesis in human colon cancer. *Cancer Res.* 61: 1255-1259.

Bennett, K. L., Jackson, D. G., Simon, J. C., Tanczos, E., Peach, R., Modrell, B., Stamenkovic, I., Plowman, G., and Aruffo, A. 1995. CD44 isoforms containing exon V3 are responsible for the presentation of heparin-binding growth factor. *J. Cell Biol.* 128: 687-698.

Bernfield, M., Gotte, M., Park, P. W., Reizes, O., Fitzgerald, M. L., Lincecum, J., and Zako, M. 1999. Functions of cell surface heparan sulfate proteoglycans. *Annu. Rev. Biochem.* 68: 729-777.

Cines, D. B., Pollak, E. S., Buck, C. A., Loscalzo, J., Zimmerman, G. A., McEver, R. P., Pober, J. S., Wick, T. M., Konkle, B. A., Schwartz, B. S., Barnathan, E. S., McCrae, K. R., Hug, B. A., Schmidt, A. M., and Stern, D. M. 1998. Endothelial cells in physiology and in the pathophysiology of vascular disorders. *Blood* 91: 3527-3561.

Davis, S., Aldrich, T. H., Jones, P. F., Acheson, A., Compton, D. L., Jain, V., Ryan, T. E., Bruno, J., Radziejewski, C., Maisonpierre, P. C., and Yancopoulos, G. D. 1996. Isolation of angiopoietin-1, a ligand for the TIE2 receptor, by secretion-Trap expression cloning. *Cell* 87: 1161-1169.

Dumont, D. J., Gradwohl, G., Fong, G. H., Puri, M. C., Gertsenstein, M., Auerbach, A., and Breitman, M. L. 1994. Dominant-negative and targeted null mutations in the endothelial receptor tyrosinekinase, tek, reveal a critical tole in vasculogenesis of the embryo. *Genes Dev.* 8: 1897-1909.

Etoh, T., Inoue, H., Tanaka, S., Barnard, G. F., Kitano, S., and Mori, M. 2001. Angiopoietin-2 is related to tumor angiogenesis in gastric carcinoma: possible in vivo regulation via induction of proteases. *Cancer Res.* 61: 2145-2153.

Fidler, I. J., and Ellis, L. M. 1994. The implications of angiogenesis for the biology and therapy of cancer metastasis. *Cell* 79: 185-188.

Folkman, J. 1971. Tumor angiogenesis: therapeutic implications. *N. Engl. J. Med.* 285: 1182-1186.

Folkman, J. 1995. Angiogenesis in cancer, vascular, rheumatoid and other disease. *Nat. Med.* 1: 27-31.

Folkman, J., and D'Amore, P. 1996. Blood vessel formation: what is its molecular basis? *Cell* 87: 1153-1155.

Gamble, J. R., Drew, J., Trezise, L., Underwood, A., Parsons, M., Kasminkas, L., Rudge, J., Yancopoulos, G., Vadas, M. A. 2000. Angiopoietin-1 is an antipermeability and anti-inflammatory agent in vitro and targets cell junctions. Circ Res. 87:603-7.

Hamid, Ali, S., O'Donnell, A. L., Balu, D., Pohl, M. B., Seyler, M. J., Mohamed, S., Mousa, S., and Dadona, P. 2000. Estrogen receptor-☐ in the inhibition of cancer growth and angiogenesis. *Cancer Res.* 60: 7094-7098.

Hanahan, D., and Folkman, J. 1996. Patterns and emerging mechanisms of the angiogenic switch during tumorigenesis. *Cell* 86: 353-364.

Hanahan, D. 1997. Signaling vascular morphogenesis and maintenance. *Science* 277: 48-50.

Hanahan, D., and Weinberg, R. A. 2000. The hallmarks of cancer. *Cell* 100: 57-70.

Hawighorst, T., Skobe, M., Streit, M., Hong, Y.-K., Velasco, P., Brown, L. F., Riccardi, L., Lange-Asschenfeldt, B., and Detmar, M. 2002. Activation of the Tie2 receptor by angiopoietin-1 enhances tumor vessel maturation and impairs squamous cell carcinoma growth. *Am. J. Pathol.* 160: 1381-1392.

Hayes, A. J., Huang, W.-Q., Mallah, J., Yang, D., Lippman, M. E. and Li, L.-Y. 1999. Angiopoietin-1 and its receptor Tie-2 participate in the regulation of capillary-like tubule formation and survival of endothelial cells. *Microvasc. Res.* 58: 224-237.

Holash, J., Maisonpierre, D., Compton, D., Boland, P., Alexander, C. R., Zagzag, D., Alexander, C. R., Zagzag, D., Yancopoulos, G. D., and Wiegland, S. J. 1999. Vessel cooption, regression, and growth in tumors mediated by angiopoietins and VEGF. *Science* 284: 1994-1998.

Ingber, D. E., and Folkman, J. 1989. How does extracellular matrix control capillary morphogenesis? *Cell* 58: 803-805.

Iozzo, R. V., and San Antonio, J. D. 2001. Heparan sulfate proteoglycans: heavy hitters in the angiogenesis arena. *J. Clin. Invest.* 108: 349-355.

Jackson, D. G., Bell, J. I., Dickinson, R., Timans, J., Shields, J., and Whittle, N. 1995. Proteoglycan forms of the lymphocyte homing receptor CD44 are alternatively spliced variants containing the v3 exon. *J. Cell Biol.* 128: 673-685.

Kim, I., Kim, H. G., So, J.-N., Kim, J. H., Kwak, H. J., and Koh, G. Y. 2000. Angiopoietin-1 regulates endothelial cell survival through the phosphatidylinositol 3'-kinase/Akt signal transduction pathway. *Circ. Res.* 86: 24-29.

Kim, I., Rya, Y. S., Kwak, H. J., Ahn, S. Y., Oh, J.-L., Yancopoulos, G. D., Gale, N. W., and Koh, G. Y. 2002. EphB ligand, ephrinB2, suppresses the VEGF- and angiopoietin 1-induced Ras/mitogen activated protein kinase pathway in venous endothelial cells. *FASEB J.* 16: 1126-1128.

Koblizek, T. I., Weiss, C., Yancopoulos, G. D., Deutsch, U., and Risau, W. 1998. Angiopoietin-1 induces sprouting angiogenesis in vitro. *Curr. Biol.* 8: 529-532.

Lin, P., Polyerini, P., Dewhirst, M., Shan, S., Rao, P. S., and Peter, K. G. 1997. Inhibition of tumor angiogenesis using a soluble receptor establishes a role for Tie-2 in pathologic vascular growth. *J. Clin. Invest.* 100: 2072-2078.

Lin, P., Buxton, J. A., Acheson, A., Radziejewski, C., Maisonpierre, P. C., Yancopoulos, G. D., Channon, K. M., Hale, L. P., Dewhirst, M. W., George, S. E., and Peters, K. G. 1998. Antiangiogenic gene therapy targeting the endothelium-specific receptor tyrosine kinase Tie2. *Proc. Natl. Acad. Sci. USA* 95: 8829-8834.

Maisonpierre, P. C., Suri, C., Jones, P. F., Bartunkova, S., Wiegand, S. J., Radziejewski, C., Compton, D., McClain, J., Aldrich, T. H., Papadopoulos, N., Daly, T. J., Davis, S., Sato, T. N., and Yancopoulos, G, D. 1997. Angiopoietin-2, a natural antagonist for Tie2 that disrupts in vivo angiogenesis. *Science* 277: 55-60.

Papapetropoulos, A., Fulton, D., Mahboubi, K., Kalb, R. G., O'Connor, D. S., Li, F., Altieri, D. C., and Sessa, W. C. 2000. Angiopoietin-1 inhibits endothelial cell apoptosis via the Akt/surviving pathway. *J. Biol. Chem.* 275: 9102-9105.

Pober, J. S. 1999 Immunobiology of human vascular endothelium. *Immunol. Res.* 19: 225-232.

Procopio, W. N., Pelavin, P. I., Lee, W. M. F., and Yeilding, N. M. 1999. Angiopoietin-1 and -2 coiled coil domains mediate distinct homo-oligomerization patterns, but fibrinogen-like domains mediate ligand activity. *J. Biol. Chem.* 274: 30196-30201.

Rapraeger, A. C., Krufka, A., and Olwin, B. B. 1991. Requirement of heparan sulfate for bFGF mediated fibroblast growth and myoblast differentiation. *Science* 252: 1705-1708.

Risau, W. 1997. Mechanisms of angiogenesis. *Nature* 386: 671-674.

Ross, R. 1993. The pathogenesis of atherosclerosis: a perspective for the 1990s. *Nature* 362: 801-809.

Sanderson, R. D. 2001. Heparan sulfate proteoglycans in invasion and metastasis. *Cell Dev. Biol.* 12:89-98.

Sato, T. N., Quin, Y., Kozak, C. A., and Audus, K. L. 1993. Tie-1 and Tie-2 define another class of putative receptor tyrosine kinase genes expressed in early embryonic vascular system. *Proc. Natl. Acad. Sci. USA* 90: 9355-9358.

Sato, T. N., Tozawa, Y., Deutsch, U., Wolburg-Burcholz, K., Fujiwara, Y., Gendron-Maguire, M., Gridley, T., Wolburg, H., Risau, W., and Qin, Y. 1995. Distinct roles of the receptor tyrosine kinases Tie-1 and Tie-2 in blood vessel formation. *Nature* 376: 70-74.

Schnurch, H., and Risau, W. 1993. Expression of Tie-2, a member of a novel family of receptor tyrosine kinases, in the endothelial cell lineage. *Development* 119: 957-968.

Siemeister, G., Schirner, M., Weindel, K., Reusch, P., Menrad, A., Marme, D., and Martiny-Baron, G. 1999. Two independent mechanisms essential for tumor angiogenesis: inhibition of human melanoma xenograft growth by interfering with either the vascular endothelial growth factor receptor pathway of the Tie-2 pathway. *Cancer Res.* 59: 3185-3191.

Southern, J. A., Young, D. F., Heaney, F., Gaumgartner, W., and Randall, R. E. 1991. Identification of an epitope on the P and V proteins of Simian virus 5 that distinguishes between two isolates with different biological characteristics. *J. Gen. Virol.* 72: 1551-1557.

Stratmann, A., Risau, W., and Plate, K. H. 1998. Cell type-specific expression of angiopoietin-1 and angiopoietin-2 suggests a role in glioblastoma angiogenesis. *Am. J. Pathol.* 153: 1459-1466.

Suri, C., Jones, P. F., Patan, S., Bartunkova, S., Maisonpierre, P. C., Davis, S., Sato, T. N., and Yancopoulos, G. D. 1996. Requisite role of angiopoietin-1, a ligand for the TIE2 receptor, during embryonic angiogenesis. *Cell* 87: 1171-1180.

Thurston, G., Suri, C., Smith, K., McClain, J., Sato, T. N., Yancopoulos, G. D., and McDonald, D. M. 1999. Leakage-resistant blood vessels in mice transgenically overexpressing angiopoietin-1. *Science* 286: 2511-2514.

Thurston, G., Rudge, J. S., Ioffe, E., Zhou, H., Ross, L., Croll, S. D, Glazer, N., Holash, J., McDonald, D. M., and Yancopoulos, G. D. 2000. Angiopoietin-1 protects the adult vasculature against plasma leakage. *Nat. Med.* 6: 460-463.

Underhill C. B., Nguyen, H. A., Shizari, M., and Culty, M. 1993. CD44 positive macrophages take up hyaluronan during lung development. *Dev. Biol.* 155:324-336.

Valenzuela, D. M., Griffiths, J. A., Rojas, J., Aldrich, T. H., Jones, P. F., Zhou, H., McClain, J., Copeland, N. G., Gilbert, D. J., Jenkins, N. A., Huang, T., Papadopoulos, N., Maisonpierre, P. C., Davis, S., and Yancopoulos, G. D. 1999. Angiopoietins 3 and 4: diverging gene counterparts in mice and humans. *Proc. Natl. Acad. Sci. USA* 96: 1904-1909.

Xu, Y., and Yu, Q. 2001. Angiopoietin-1, unlike angiopoietin-2, is incorporated into the extracellular matrix via its linker peptide region. *J. Biol. Chem.* 276: 34990-34998.

Xu, Y., and Yu, Q. 2003. E-cadherin negatively regulates CD44-hyaluronan interaction and CD44-mediated tumor invasion and branching morphogenesis. *J. Biol. Chem.* 278: 8661-8668.

Yancopoulos, G. D., Davis, S., Gale, N. W., Rudge, J. S., Wiegand, S. J., Holash, J. 2000. Vascular-Specific growth factors and blood vessel formation. *Nature* 407: 242-248.

Yayon, A., Klagsbrun, M., Esko, J. D., Leder, P., and Ornitz, D. M. 1991. Cell surface, heparin-like molecules are required for binding of basic fibroblast growth factor to its high affinity receptor. *Cell* 64: 841-848.

Yu, Q., Toole, B. P., and Stamenkovic, I. 1997. Induction of apoptosis of metastatic mammary carcinoma cells in vivo by disruption of tumor cell surface CD44 function. *J. Exp. Med,* 186: 1985-1996.

Yu, Q., and Stamenkovic, I. 1999. Localization of matrix metalloproteinase 9 (MMP-9) to the cell surface provides a mechanism for CD44-mediated tumor invasion. *Genes & Dev.* 13: 35-48.

Yu, Q., and Stamenkovic, I. 2001. Angiopoietin-2 is implicated in the regulation of tumor angiogenesis. *Am. J. Pathol.* 158: 563-570.

Iozzo R V. 2001. Heparan sulfate proteoglycans: intricate molecules with intriguing functions. *J Clin Invest.* 108: 165-167.

Battaglia C, Aumailley M, Mann K, Mayer U, Timpl R. 1993. Structural basis of beta 1 integrin-mediated cell adhesion to a large heparan sulfate proteoglycan from basement membranes. *Eur J Cell Biol.* 61:92-99.

Chakravarti S, Horchar T, Jefferson B, Laurie G W, Hassell J R. 1995. Recombinant domain III of perlecan promotes cell attachment through its RGDS sequence. *J Biol Chem.* 270:404-409.

Brown J C, Sasaki T, Gohring W, Yamada Y, Timpl R. 1997. The C-terminal domain V of perlecan promotes beta1 integrin-mediated cell adhesion, binds heparin, nidogen and fibulin-2 and can be modified by glycosaminoglycans. *Eur J Biochem.* 250:39-46.

Kleeff J, Ishiwata T, Kumbasar A, Friess H, Buchler M W, Lander A D, Korc M. 1998. The cell-surface heparan sulfate proteoglycan glypican-1 regulates growth factor action in pancreatic carcinoma cells and is overexpressed in human pancreatic cancer. *J Clin Invest.* 102:1662-1673.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety. Each accession numbers cited in the present application and the sequence associated with the accession number is incorporated herein by reference in its entirety.

What is claimed is:

1. A polypeptide comprising a signal peptide linked to an Angiopoietin-4 (Ang-4) fragment; wherein:
   the Angiopoietin-4 fragment comprises Angiopoietin-4 fibrinogen homology domain;
   the Angiopoietin-4 fragment is free of Angiopoietin-4 coiled-coiled domain;
   the Angiopoietin-4 fragment is effective to treat cancer; and
   Angiopoietin-4 is encoded by SEQ ID NO:3.

2. The polypeptide of claim 1, wherein the signal peptide is an Angiopoietin-4 signal peptide.

3. The polypeptide of claim 2, wherein the polypeptide further comprises an Angiopoietin-4 linker domain.

4. The polypeptide of claim 3, wherein the polypeptide consists of the Angiopoietin-4 signal peptide, the Angiopoietin-4 linker domain and the Angiopoietin-4 fibrinogen homology domain.

* * * * *